US007105471B2

(12) United States Patent
Lieb et al.

(10) Patent No.: US 7,105,471 B2
(45) Date of Patent: Sep. 12, 2006

(54) ARYLPHENYL-SUBSTITUTED CYCLIC KETOENOLS

(75) Inventors: Folker Lieb, Leverkusen (DE); Reiner Fischer, Monheim (DE); Alan Graff, Köln (DE); Udo Schneider, Leverkusen (DE); Thomas Bretschneider, Lohmar (DE); Christoph Erdelen, Leichlingen (DE); Wolfram Andersch, Bergisch Gladbach (DE); Mark-Wilhelm Drewes, Langenfeld (DE); Markus Dollinger, Overland Park, KS (US); Ingo Wetcholowsky, Estancia Marambaia (BR); Randy Allen Myers, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 205 days.

(21) Appl. No.: 10/777,528

(22) Filed: Feb. 12, 2004

(65) Prior Publication Data

US 2004/0167031 A1    Aug. 26, 2004

Related U.S. Application Data

(62) Division of application No. 10/137,763, filed on May 2, 2002, now Pat. No. 6,716,832, which is a division of application No. 09/623,016, filed as application No. PCT/EP99/01029 on Feb. 17, 1999, now Pat. No. 6,417,370.

(30) Foreign Application Priority Data

Feb. 27, 1998 (DE) ................. 198 08 261

(51) Int. Cl.
*C07D 401/04* (2006.01)
*A01N 43/56* (2006.01)

(52) U.S. Cl. ............ 504/239; 504/253; 504/261; 504/265; 504/266; 504/282; 544/333; 546/275.4; 548/128; 548/131; 548/146; 548/366.4

(58) Field of Classification Search ............. 544/333; 546/275.4; 548/128, 131, 146, 366.4; 504/239, 504/253, 261, 265, 266, 282
See application file for complete search history.

(56) References Cited

U.S. PATENT DOCUMENTS

| | | | |
|---|---|---|---|
| 4,104,043 A | 8/1978 | Durden, Jr. et al. .......... 71/107 |
| 4,175,135 A | 11/1979 | Haines ....................... 424/311 |
| 4,209,432 A | 6/1980 | Roth ..................... 260/29.2 M |
| 4,256,657 A | 3/1981 | Wheeler ................ 260/465 D |
| 4,256,658 A | 3/1981 | Wheeler ................ 260/465 D |
| 4,256,659 A | 3/1981 | Wheeler ................ 204/465 D |
| 4,257,858 A | 3/1981 | Wheeler ................ 204/158 R |
| 4,283,348 A | 8/1981 | Wheeler ................ 260/465 D |
| 4,303,669 A | 12/1981 | D'Silva ..................... 424/282 |
| 4,338,122 A | 7/1982 | Wheeler ..................... 71/122 |
| 4,351,666 A | 9/1982 | Koerwer ..................... 71/106 |
| 4,409,153 A | 10/1983 | Hodakowski ............... 260/946 |
| 4,422,870 A | 12/1983 | Wheeler ..................... 71/106 |
| 4,436,666 A | 3/1984 | Wheeler ................. 260/455 B |
| 4,526,723 A | 7/1985 | Wheeler et al. .......... 260/410.5 |
| 4,551,547 A | 11/1985 | Wheeler ..................... 560/255 |
| 4,613,617 A | 9/1986 | Sousa ........................ 514/521 |
| 4,632,698 A | 12/1986 | Wheeler ..................... 71/106 |
| 4,659,372 A | 4/1987 | Wheeler ..................... 71/106 |
| 4,925,868 A | 5/1990 | Terao et al. ................. 514/425 |
| 4,985,063 A | 1/1991 | Fischer et al. ............... 71/88 |
| 5,045,560 A | 9/1991 | Fischer et al. .............. 514/425 |
| 5,091,537 A | 2/1992 | Fischer et al. .............. 546/226 |
| 5,094,681 A | 3/1992 | Krämer et al. ................ 71/88 |
| 5,116,836 A | 5/1992 | Fischer et al. ............ 514/224.2 |
| 5,142,065 A | 8/1992 | Fischer et al. .............. 548/533 |
| 5,186,737 A | 2/1993 | Fischer et al. .............. 504/283 |
| 5,207,817 A | 5/1993 | Krämer et al. .............. 504/299 |
| 5,225,434 A | 7/1993 | Bertram et al. .............. 514/411 |
| 5,258,527 A | 11/1993 | Krauskoph et al. ......... 548/543 |
| 5,262,383 A | 11/1993 | Fischer et al. .............. 504/195 |
| 5,332,720 A | 7/1994 | Krüger et al. .............. 504/281 |
| 5,358,924 A | 10/1994 | Krüger et al. .............. 504/197 |
| 5,462,913 A | 10/1995 | Fischer et al. .............. 504/138 |
| 5,494,890 A | 2/1996 | Cederbaum et al. ........ 504/281 |
| 5,504,057 A | 4/1996 | Fischer et al. .............. 504/283 |
| 5,506,193 A | 4/1996 | Cederbaum et al. ........ 504/282 |
| 5,565,450 A | 10/1996 | Fischer et al. ............ 514/227.2 |
| 5,567,671 A | 10/1996 | Fischer et al. .............. 504/283 |
| 5,602,078 A | 2/1997 | Fischer et al. .............. 504/283 |
| 5,610,122 A | 3/1997 | Fischer et al. .............. 504/251 |
| 5,622,917 A | 4/1997 | Fischer et al. .............. 504/283 |
| 5,661,110 A | 8/1997 | Krüger et al. .............. 504/281 |
| 5,677,449 A | 10/1997 | Fischer et al. .............. 544/165 |
| 5,719,310 A | 2/1998 | Fischer et al. ................ 560/83 |
| 5,739,389 A | 4/1998 | Krüger et al. .............. 562/489 |
| 5,780,394 A | 7/1998 | Krüger et al. .............. 504/281 |
| 5,808,135 A | 9/1998 | Fischer et al. .............. 560/129 |
| 5,830,826 A | 11/1998 | Fischer et al. .............. 504/195 |
| 5,840,661 A | 11/1998 | Fischer et al. .............. 504/348 |
| 5,945,444 A | 8/1999 | Fischer et al. .............. 514/445 |
| 5,977,029 A | 11/1999 | Fischer et al. .............. 504/292 |
| 5,994,274 A | 11/1999 | Fischer et al. .............. 504/282 |
| 6,057,352 A | 5/2000 | Brown et al. ............... 514/384 |
| 6,071,937 A | 6/2000 | Bretschneider et al. ..... 514/336 |
| 6,096,895 A | 8/2000 | Brown et al. .............. 548/110 |
| 6,110,872 A | 8/2000 | Lieb et al. .................. 504/284 |
| 6,114,374 A | 9/2000 | Lieb et al. .................. 514/424 |
| 6,140,358 A | 10/2000 | Lieb et al. .................. 514/425 |
| 6,150,304 A | 11/2000 | Fischer et al. .............. 504/309 |
| 6,358,887 B1 | 3/2002 | Fischer et al. .............. 504/284 |

FOREIGN PATENT DOCUMENTS

| | | |
|---|---|---|
| DE | 521334 | 1/1993 |
| DE | 44 31 730 | 8/1995 |
| DE | 195 43 864 | 8/1996 |
| DE | 196 49 665 | 10/1997 |
| EP | 442077 | 8/1991 |
| GB | 2266888 | 5/1993 |
| WO | 95/20572 | 8/1995 |
| WO | 96/02539 | 2/1996 |
| WO | 96/20196 | 7/1996 |
| WO | 96/21652 | 7/1996 |
| WO | 96/25395 | 8/1996 |
| WO | 96/35664 | 11/1996 |
| WO | 96/36229 | 11/1996 |

| WO | 96/36615 | 11/1996 |
| WO | 97/14667 | 4/1997 |

OTHER PUBLICATIONS

Merck Index, 11th ed., Merck & Co. Rahway, p. 3312, Compound No. 3314, (month unavailable) 1989.
Chem. Pharm Bull., 15, (month unavailable), 1967, pp. 1120-1122, Seikichi Suzuki, et al, "Studies on Antiviral Agents. $M^1$ Biological Activity of Tenuazonic Acid Derivatives".
Liebigs Ann. Chem. (month unavailable), 1985, pp. 1095-1098, Roland Schmierer et al, "Cyclisierung von N-Acylalanin- und N-Acylglycinestern".
J. Chem. Soc. Perkin Trans. 1, (month unavailable), 1985, pp. 1567-1576, A. C. Campbell et al, "Synthesis of (E)- and (Z)-Pulvinones".
J. Heterocycl. Chem., 25 (5), Sep.-Oct., 1988, pp. 1301-1305, G. Zvilichovsky, "Crystal Structure, Dissociation and Zwitterion Formation in 2,6-Diaryl-1(3)-oxo-3(1)-hydroxy-5(7)-imino-7(5)-amino-1H,5H-(3H,7H)-pyrazolo[1,2-a]pyrazoles".
J. Heterocycl. Chem, 25 (5), Sep.-Oct., 1988, pp. 1307-1310, G. Zvilichovsky, "Acidity and Alkylation of 4-Phenyl-3,5-dihydroxy-pyrazole and Its Derivatives. C versus O and N Alkylation".
Zh. Obshch. Khem., 34 (7), (month unavailable), 1964, pp. 239-240, Z. I. Miroshnichenko et al, "Cyanine Dyes, Derivatives of 2-Methyl 4,5-(2',3'-Thionaphtheno)Thiazole".
Farmakol Toksikol (Moscow), 38 (2), (month unavailable), 1976, pp. 180-186, K. M. Lakin et al, "The Effect of Some Pyrazolone Derivatives on the Aggregation of Thrombocytes" (Abstract on p. 186).
Arch. Pharm. 309, (month unavailable) 1976, pp. 558-564, A. M. Chirazi et al, "Zur Synthese von Kawalactonderivaten".
Chem. Bec., 91 (date unavailable), p. 2849, K.-H. Boltze et al, "Ringschlüsse mit Malonsäure-dichloriden".
Monatsh, 95 (month unavailable) 1964, pp. 147-155, E. Ziegler et al, "Synthesen von Heterocyclen, 52. Mitt.: Über Derivate des 2-Phenyl-4-hydroxy-[1,3-thiazinons-(6)]".
Heterocycl. Chem., Apr. 10, 1973, pp. 223-224, Roger Ketcham et al, "Synthesis of Heterocycles. 174 (1,2) Substituted Thiazines and Bisthiazinyls from Dithiooxamide and Trichlorophenyl Malonates".
Tetrahedron, vol. 48, (month unavailable), 1992, pp. 7519-7526, J. Micklefield et al, "Alkylation and Acylation of 5-Phenylsulphonyl- and 5-Cyanobutyrolactones".
J. Chem. Soc. (C), (month unavailable), 1967, pp. 405-409, R. L. Edwards et al, "Constituents of the Higher Fungi, Part IV. Involutin, A Diphenylcyclopenteneone from *Paxillus involutis* (Oeder ex Fries)".
J. Economic Entomology, vol. 66, (month unavailable), 1973, pp. 584-586, A. A. Sousa et al, "Esters of 3-Hydroxy-2-Arylindones, A New Class Of Acaricide".
J. Org. Chem., vol. 44, (month unavailable), 1979, pp. 4906-4912, T. N. Wheeler, "Novel Photochemical Synthesis of 2-Aryl-1,3-Cyclohexanediones".

*Primary Examiner*—Zinna Northington Davis
(74) *Attorney, Agent, or Firm*—Richard E. L. Henderson; Raymond J. Harmuth

(57) ABSTRACT

The present invention relates to novel arylphenyl-substituted cyclic ketoenols of the formula (I)

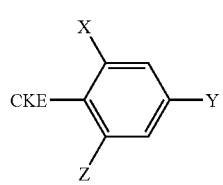

(I)

in which

X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or in each case optionally substituted phenyl, phenoxy, phenylthio, phenylalkoxy or phenylalkylthio, Y represents in each case optionally substituted cycloalkyl, aryl or hetaryl, Z represents hydrogen, halogen, alkyl, alkoxy, alkenyloxy, halogenoalkyl, halogenoalkoxy, halogenoalkenyloxy, nitro or cyano, CKE represents one of the groups

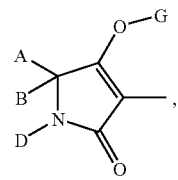

(1)

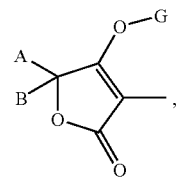

(2)

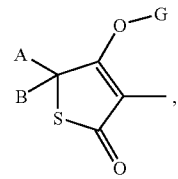

(3)

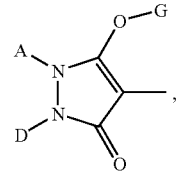

(4)

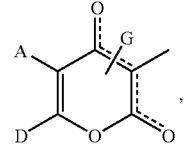

(5)

-continued
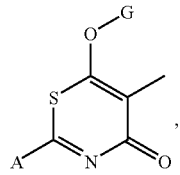
(6)
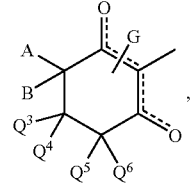
(8)
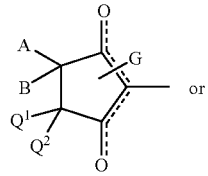
or
(7)
in which
A, B, D, G and $Q^1$ to $Q^6$ are each as defined in the description,
to a plurality of processes for their preparation and to their use as pesticides and herbicides.
8 Claims, No Drawings

ARYLPHENYL-SUBSTITUTED CYCLIC KETOENOLS

This application is a divisional application of U.S. patent application Ser. No. 10/137,763 filed May 2, 2002, now U.S. Pat. No. 6,716,832 for which a Notice of Allowance was issued Nov. 20, 2003, which in turn was a divisional application of U.S. patent application Ser. No. 09/623,016 filed Oct. 23, 2000, now U.S. Pat. No. 6,417,370 issued Jul. 9, 2002, which was the national stage of PCT/EP99/01029 filed Feb. 17, 1999, claiming priority of German Patent DE 198 08 261.4, filed Feb. 27, 1998.

The present invention relates to novel arylphenyl-substituted cyclic ketoenols, to a plurality of processes for their preparation and to their use as pesticides and herbicides.

Pharmaceutical properties of 3-acyl-pyrrolidine-2,4-diones have already been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-aryl-pyrrolidine-2,4-diones) of which, however, no herbicidal, insecticidal or acaricidal activity has become known. Unsubstituted bicyclic 3-aryl-pyrrolidine-2,4-dione derivatives (EP-A-355 599 and EP415 211) and substituted monocyclic 3-aryl-pyrrolidine-2,4-dione derivatives (EP-A-377 893 and EP-442 077) having herbicidal, insecticidal or acaricidal activity are known.

Also known are polycyclic 3-arylpyrrolidine-2,4-dione derivatives (EP-442 073) and 1H-arylpyrrolidine-dione derivatives (EP-456 063, EP-521 334, EP-596 298, EP-613 884, EP-613 885, WO 94/01 997, WO 95/26 954, WO 95/20 572, EP-A-0 668 267, WO 96/25 395, WO 96/35 664, WO 97/01 535, WO 97/02 243 and WO 97/36 868, WO 98/05 638).

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methyl-phenyl)-4-hydroxy-5-(4-fluorophenyl)-$\Delta^3$-dihydrofuran-2-one) is likewise described in DE-A-4 014 420. Compounds of a similar structure are known from the publication Campbell et al., J. Chem. Soc., Perkin Trans. 1, 1985, (8) 1567–76, without any insecticidal and/or acaricidal activity being mentioned. Furthermore, 3-aryl-$\Delta^3$-di-hydrofuranone derivatives having herbicidal, acaricidal and insecticidal properties are known from EP-A-528 156, EP-A-0 647 637, WO 95/26 345, WO 96/20 196, WO 96/25 395, WO 96/35 664, WO 97/01 535, WO 97/02 243 and WO 97/36 868, WO 98/05 638. 3-Aryl-$\Delta^3$-dihydrothiophene-one derivatives are likewise known (WO 95/26 345, 96/25 395, WO 97/01 535, WO 97/02 243, WO 97/36 868, WO 98/05 638).

Also known from the literature are certain 3H-pyrazol-3-one derivatives, such as, for example, 1,2-diethyl-1,2-dihydro-5-hydroxy-4-phenyl-3H-pyrazol-3-one or [5-oxo-1,2-diphenyl-4-(p-sulphophenyl)-3-pyrazolin-3-yl]-oxy, disodium salt, or p-(3-hydroxy-5-oxo-1,2-diphenyl-3-pyrazolin-4-yl)-benzenesulphonic acid (cf. J. Heterocycl. Chem., 25(5), 1301–1305, 1988 or J. Heterocycl. Chem., 25(5), 1307–1310, 1988 or Zh. Obshch. Khim., 34(7), 2397–2402, 1964). However, a biological activity of these compounds is not described.

Furthermore, it is known that the trisodium salt of 4,4', 4"-(5-hydroxy-3-oxo-1H-pyrazol-1,2,4(3H)-triyl)-tris-benzenesulphonic acid has pharmacological properties (cf. Farmakol. Toksikol. (Moscow), 38(2), 180–186, 1976). However, it is not known to be used in crop protection.

Moreover, EP-508 126 and WO 92/16 510, WO 96/21 652 describe 4-arylpyrazolidin-3,5-dione derivatives having herbicidal, acaricidal and insecticidal properties. Additionally, 4-arylpyrazolidines have become known of which fungicidal properties have been described (WO 96/36 229, WO 96/36 615, WO 96/36 616, WO 96/36 633).

Certain phenyl-pyrone derivatives which are unsubstituted in the phenyl ring have already become known (cf. A. M. Chirazi, T. Kappe and E. Ziegler, Arch. Pharm. 309, 558 (1976) and K.-H. Boltze and K. Heidenbluth, Chem. Ber. 91, 2849), a possible use of these compounds as pesticides not being mentioned. Phenyl-pyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941 and WO 97/36 868, WO 98/05 638.

Certain 5-phenyl-1,3-thiazine derivatives which are unsubstituted in the phenyl ring have already become known (cf. E. Ziegler and E. Steiner, Monatsh. 95, 147 (1964), R. Ketcham, T. Kappe and E. Ziegler, J. Heterocycl. Chem. 10, 223 (1973)), a possible use of these compounds as pesticides not being mentioned. 5-Phenyl-1,3-thiazine derivatives which are substituted in the phenyl ring and have herbicidal, acaricidal and insecticidal activity are described in WO 94/14 785, WO 96/02 539, WO 96/35 664, WO 97/01535, WO 97/02 243, WO 97/02 243, WO 97/36 868.

It is known that certain substituted 2-arylcyclopentanediones have herbicidal and acaricidal properties (cf., for example, U.S. Pat. Nos. 4,283,348; 4,338,122; 4,436,666; 4,526,723; 4,551,547; 4,632,698; WO 96/01 798; WO 96/03 366 and also WO 97/14 667). Moreover, compounds of a similar structure are known: 3-hydroxy-5,5-dimethyl-2-phenylcyclopent-2-ene-1-one from the publication Micklefield et al., Tetrahedron, (1992), 7519–26 and the natural product involutine (−)-cis-5-(3,4-dihydroxyphenyl)-3,4-dihydroxy-2-(4-hydroxyphenyl)-cyclopent-2-ene-one from the publication Edwards et al., J. Chem. Soc. S, (1967), 405–9. An insecticidal or acaricidal activity is not described. Moreover, 2-(2,4,6-trimethylphenyl)-1,3-indanedione is known from the publication J. Economic Entomology, 66, (1973), 584 and the Offenlegungsschrift DE-2 361 084, with herbicidal and acaricidal activities being mentioned.

It is known that certain substituted 2-arylcyclohexanediones have herbicidal and acaricidal properties (cf., for example, U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-2 813 341, and also Wheeler, T. N., J. Org. Chem. 44, 4906 (1979)).

However, the activity and the activity spectrum of these compounds are, in particular at low application rates and concentrations, not always entirely satisfactory. Furthermore, the compatibility of these compounds with plants is not always satisfactory.

This invention, accordingly, provides novel compounds of the formula (I)

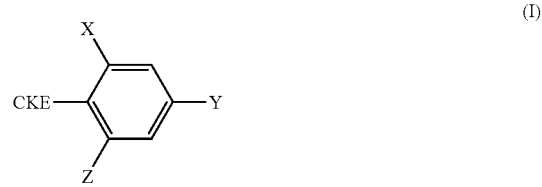

in which

X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or in each case optionally substituted phenyl, phenoxy, phenylthio, phenylalkoxy or phenylalkylthio, Y represents in each case optionally substituted cycloalkyl, aryl or hetaryl, Z represents hydrogen, halogen, alkyl, alkoxy, alkenyloxy, halogenoalkyl, halogenoalkoxy, halogenoalkenyloxy, nitro or cyano, CKE represents one of the groups

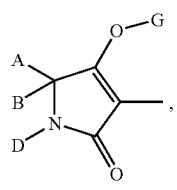 (1)

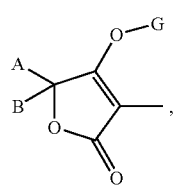 (2)

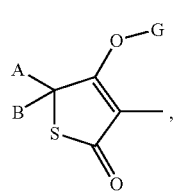 (3)

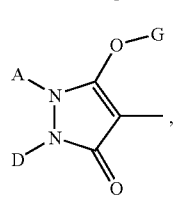 (4)

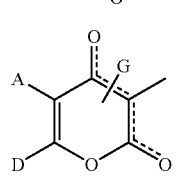 (5)

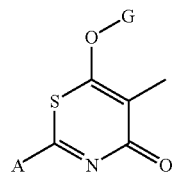 (6)

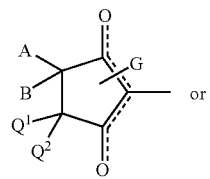 or (7)

-continued

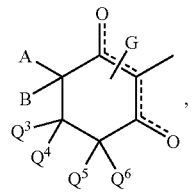 (8)

in which

A represents hydrogen, in each case optionally halogen-substituted alkyl, alkenyl, alkoxyalkyl, polyalkoxyalkyl, alkylthioalkyl, saturated or unsaturated, optionally substituted cycloalkyl in which optionally at least one ring atom is replaced by a heteroatom, or in each case optionally halogen-, alkyl-, halogenoalkyl-, alkoxy, halogenoalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated unsubstituted or substituted cycle which optionally contains at least one heteroatom, D represents hydrogen or an optionally substituted radical selected from the series consisting of alkyl, alkenyl, alkinyl, alkoxyalkyl, polyalkoxyalkyl, alkylthioalkyl, saturated or unsaturated cycloalkyl in which one or more ring members are optionally replaced by heteroatoms, arylalkyl, aryl, hetarylalkyl or hetaryl or A and D together with the atoms to which they are attached represent a saturated or unsaturated cycle which is unsubstituted or substituted in the A,D moiety and which optionally contains at least one (in the case where CKE=(4) further) heteroatom, or A and $Q^1$ together represent alkanediyl or alkenediyl, each of which is optionally substituted by in each case optionally substituted alkyl, hydroxyl, alkoxy, alkylthio, cycloalkyl, benzyloxy or aryl, or $Q^1$ represents hydrogen or alkyl, $Q^2$, $Q^4$, $Q^5$ and $Q^6$ independently of one another each represent hydrogen or alkyl, $Q^3$ represents hydrogen, alkyl, alkoxyalkyl, alkylthioalkyl, optionally substituted cycloalkyl (in which optionally one methylene group is replaced by oxygen or sulphur) or optionally substituted phenyl, or $Q^3$ and $Q^4$ together with the carbon atom to which they are attached represent a saturated or unsaturated unsubstituted or substituted cycle which optionally contains a heteroatom, G represents hydrogen (a) or represents one of the groups

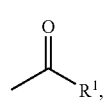 (b)

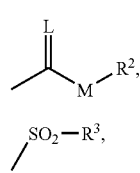 (c)

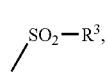 (d)

-continued

 (e)

E or

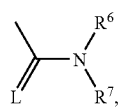 (f)

(g)

in which
E represents a metal ion or an ammonium ion,
L represents oxygen or sulphur,
M represents oxygen or sulphur,
R¹ represents in each case optionally halogen-substituted alkyl, alkenyl, alkoxyalkyl, alkylthioalkyl, polyalkoxyalkyl or optionally halogen-, alkyl- or alkoxy-substituted cycloalkyl, in which one or more methylene groups can be replaced with heteroatoms, in each case optionally substituted phenyl, phenylalkyl, hetaryl, phenoxyalkyl or hetaryloxyalkyl,
R² represents in each case optionally halogen-substituted alkyl, alkenyl, alkoxyalkyl, polyalkoxyalkyl or represents in each case optionally substituted cycloalkyl, phenyl or benzyl,
R³, R⁴ and R⁵ independently of one another each represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio,
R⁶ and R⁷ independently of one another each represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulphur.

Depending, inter alia, on the nature of the substituents, the compounds of the formula (I) can be present as geometrical and/or optical isomers or mixtures of isomers in varying compositions, which can be separated, if desired, in a customary manner. The present invention provides both the pure isomers and the isomer mixtures, their preparation and use and also compositions comprising them. In the following, for simplicity, however, compounds of the formula (I) are always referred to, although both pure compounds and, if appropriate, mixtures having different proportions of isomeric compounds are intended.

Including the meanings (1) to (8) of the group CKE, the following principal structures (I-1) to (I-8) result:

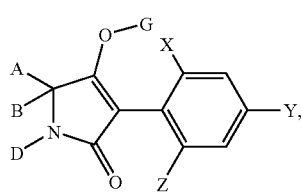 (I-1)

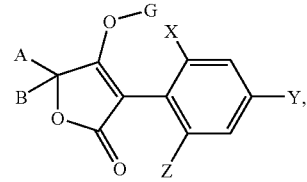 (I-2)

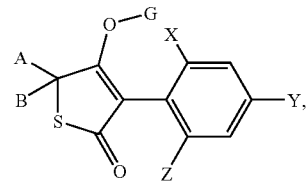 (I-3)

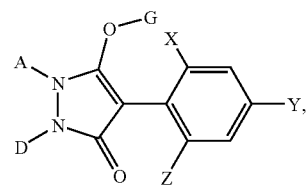 (I-4)

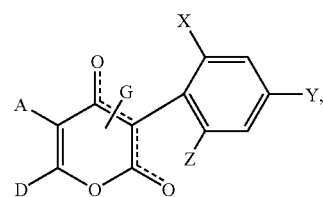 (I-5)

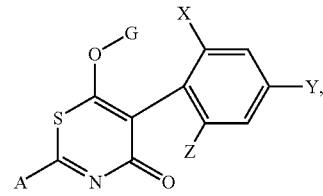 (I-6)

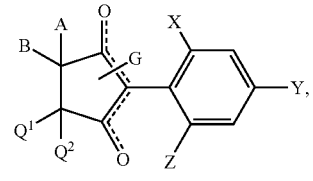 (I-7)

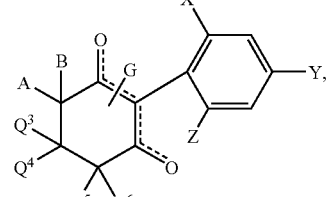 (I-8)

in which
A, B, D, G, Q¹, Q², Q³, Q⁴, Q⁵, Q⁶, X, Y and Z are each as defined above.

Including the various meanings (a), (b), (c), (d), (e), (f) and (g) of the group G, the following principal structures (I-1-a) to (I-1-g), result if CKE represents the group (1), (I-1-a):
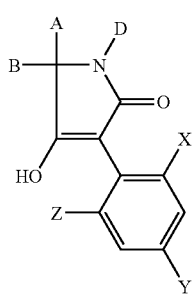
(I-1-b):
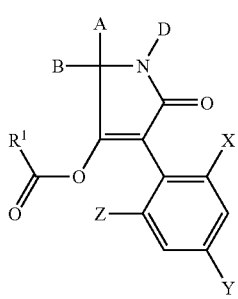
(I-1-c):
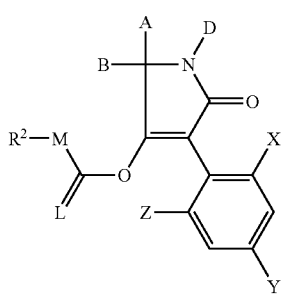
(I-1-d):
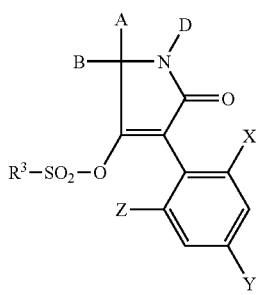
(I-1-e):
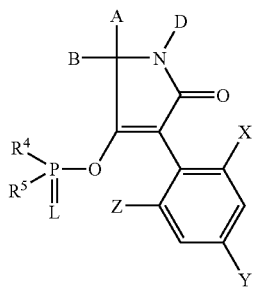
(I-1-f):
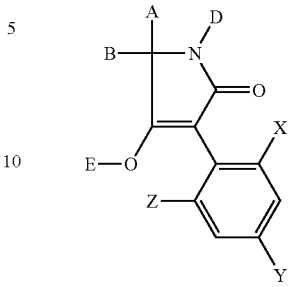
(I-1-g):
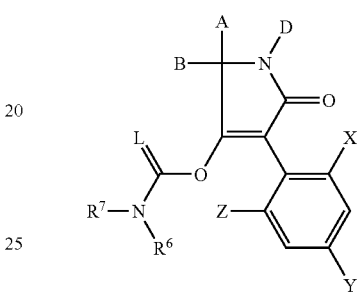
in which
A, B, D, E, L, M, X, Y, Z, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-2-a) to (I-2-g), result if CKE represents the group (2),
(I-2-a):
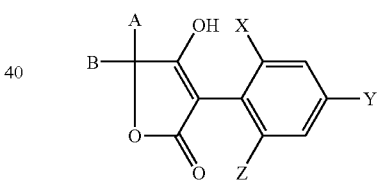
(I-2-b):
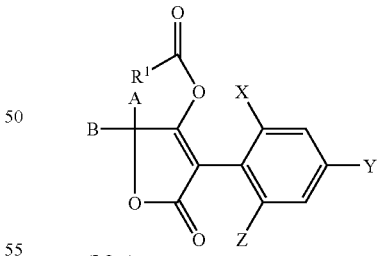
(I-2-c):
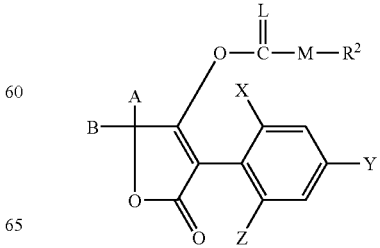

-continued
(I-2-d):
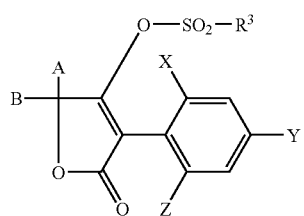
(I-2-e):
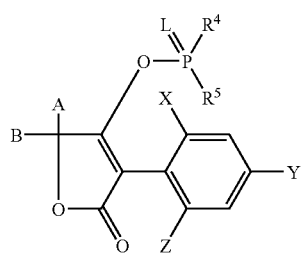
(I-2-f):
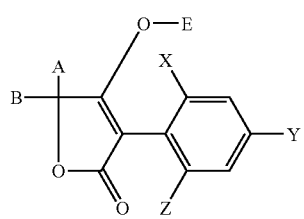
(I-2-g):
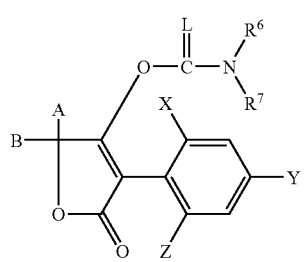
in which
A, B, E, L, M, X, Y, Z, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-3-a) to (I-3-g), result if CKE represents the group (3),
(I-3-a):
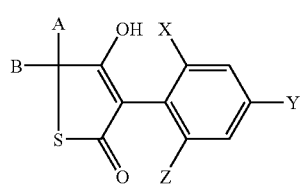
-continued
(I-3-b):
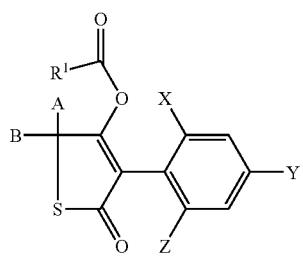
(I-3-c):
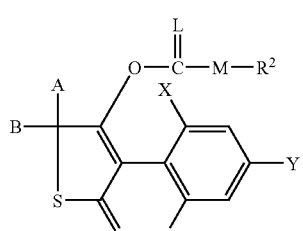
(I-3-d):
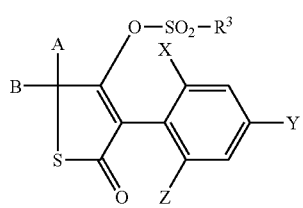
(I-3-e):
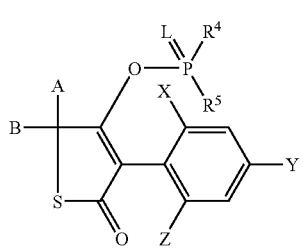
(I-3-f):
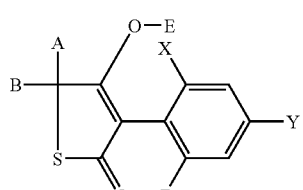
(I-3-g):
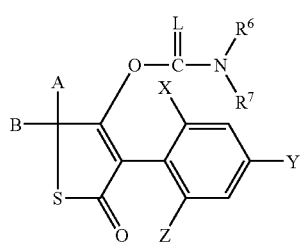

in which

A, B, E, L, M, X, Y, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-4-a) to (I-4-g), result if CKE represents the group (4), (I-4-a):

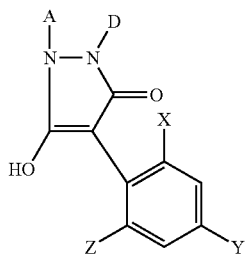

(I-4-b):

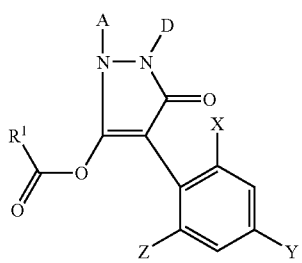

(I-4-c):

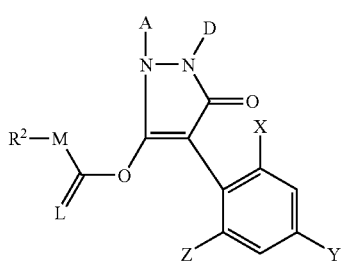

(I-4-d):

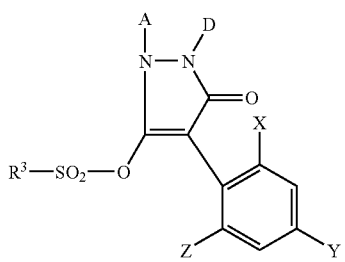

(I-4-e):

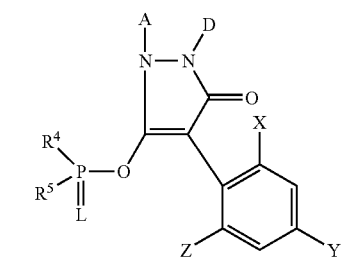

(I-4-f):

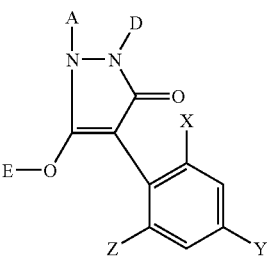

(I-4-g):

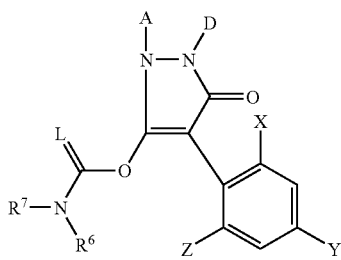

in which

A, D, E, L, M, X, Y, Z, $R^1$, $R^2$, $R^3$, $R^4$, $R^5$, $R^6$ and $R^7$ are each as defined above.

Depending on the position of the substituent G, the compounds of the formula (I-5) can be present in the two isomeric forms of the formulae (I-5-A) and (I-5-B),

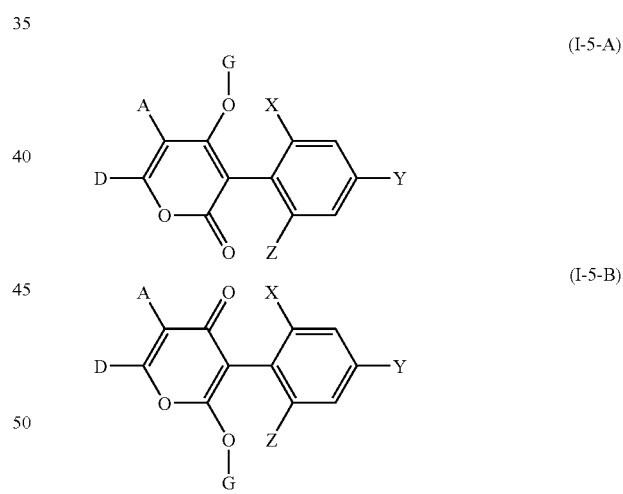

which is meant to be indicated by the dashed line in the formula (I-5).

The compounds of the formulae (I-5-A) and (I-5-B) can be present both as mixtures and in the form of their pure isomers. Mixtures of the compounds of the formulae (I-5-A) and (I-5-B) can be separated, if desired, in a manner known per se by physical methods, for example by chromatographic methods.

For reasons of clarity, hereinbelow in each case only one of the possible isomers is given. This does not exclude that the compounds may, if appropriate, be present in the form of the isomer mixtures or in the respective other isomeric form.

Including the various meanings (a), (b), (c), (d), (e), (f) and (g) of the group G, the following principal structures (I-5-a) to (I-5-g) result if CKE represents the group (5), (I-5-a):

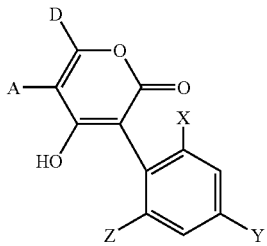

(I-5-b):

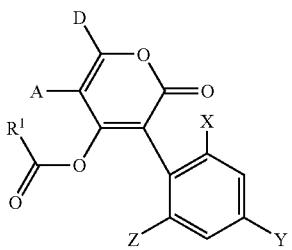

(I-5-b):

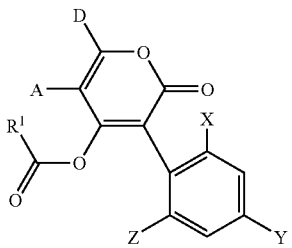

(I-5-c):

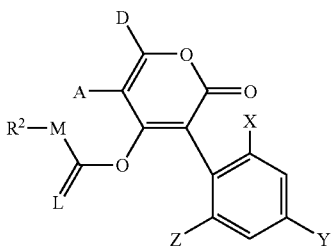

(I-5-d):

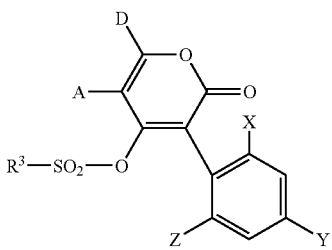

-continued (I-5-e):

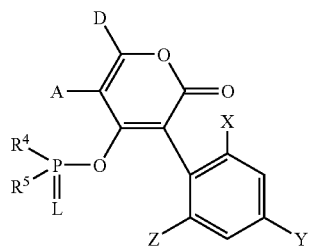

(I-5-f):

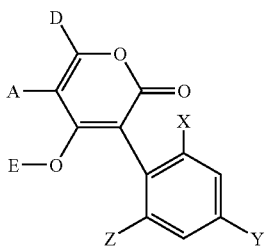

(I-5-g):

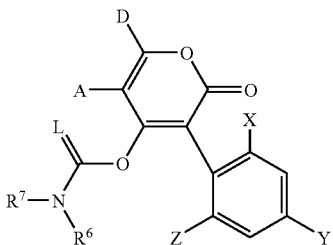

in which
A, D, E, L, M, X, Y, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-6-a) to (I-6-g), result if CKE represents the group (6), (I-6-a):

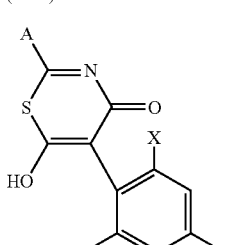

(I-6-b):

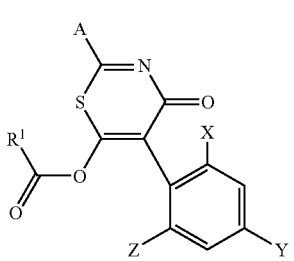

-continued (I-6-c): 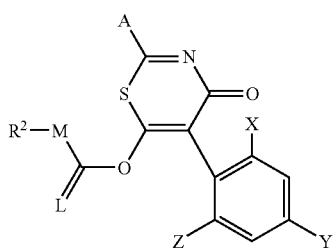

(I-6-d): 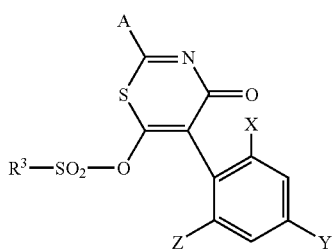

(I-6-e): 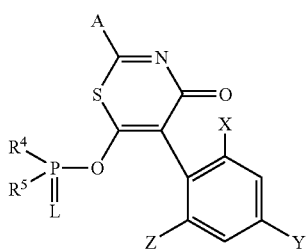

(I-6-f): 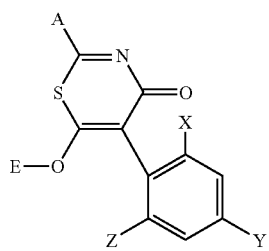

(I-6-g): 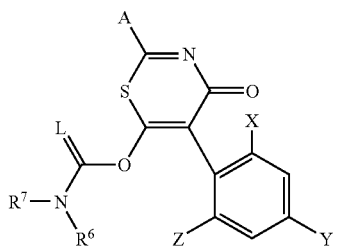

in which
A, E, L, M, X, Y, Z, $R^1$, $R^2$, $R^3$, $R^4$, $R^5$, $R^6$ and $R^7$ are each as defined above.

Depending on the position of the substituent G, the compounds of the formula (I-7) can be present in the two isomeric forms of the formulae (I-7-A) and (I-7-B):

(I-7-A): 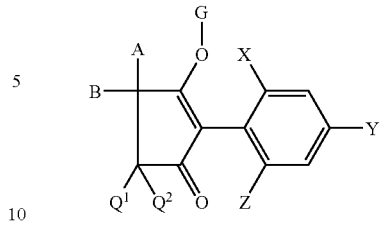

(I-7-B): 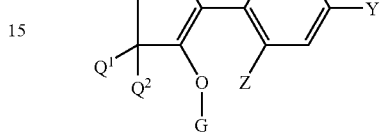

which is meant to be indicated by the dashed line in the formula (I).

The compounds of the formulae (I-7-A) and (I-7-B) can be present both as mixtures and in the form of their pure isomers. Mixtures of the compounds of the formulae (I-7-A) and (I-7-B) can be separated, if desired, by physical methods, for example by chromatographic methods.

For reasons of clarity, hereinbelow in each case only one of the possible isomers is given. This does not exclude that the compounds may, if appropriate, be present in the form of the isomer mixtures or in the respective other isomeric form.

Including the various meanings (a), (b), (c), (d), (e), (f) and (g) of the group G, the following principal structures (I-7-a) to (I-7-g) result:

(I-7-a): 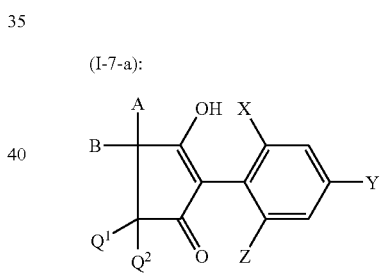

(I-7-b): 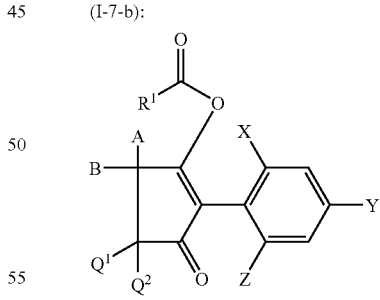

(I-7-c): 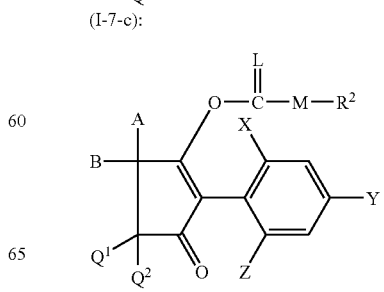

-continued (I-7-d):
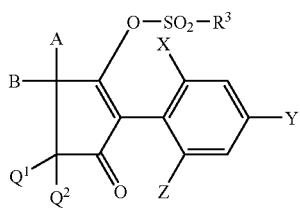

(I-7-e):
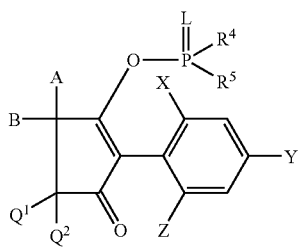

(I-7-f):
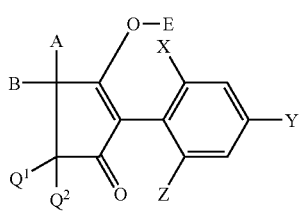

(I-7-g):
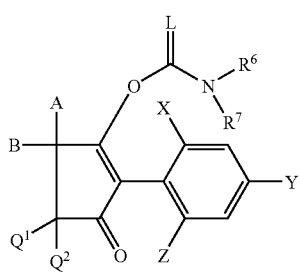

in which
A, B, $Q^1$, $Q^2$, E, L, M, X, Y, Z, $R^1$, $R^2$, $R^3$, $R^4$, $R^5$, $R^6$ and $R^7$ are each as defined above.

Depending on the position of the substituent G, the compounds of the formula (I-8) can be present in the two isomeric forms of the formulae (I-8-A) and (I-8-B)

(I-8-A)
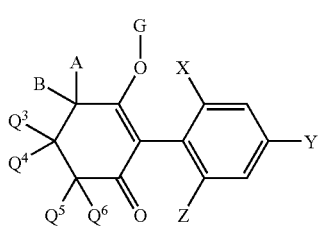

(I-8-B)
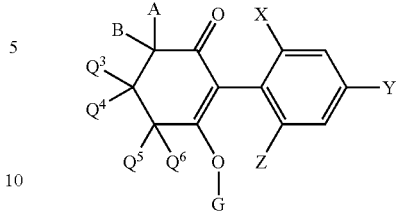

which is meant to be indicated by the dashed line in the formula (I).

The compounds of the formulae (I-8-A) and (I-8-B) can be present both as mixtures and in the form of their pure isomers. Mixtures of the compounds of the formulae (I-8-A) and (I-8-B) can be separated, if desired, by physical methods, for example by chromatographic methods.

For reasons of clarity, hereinbelow in each case only one of the possible isomers is given. This takes into account that the relevant compound may, if appropriate, be present as an isomer mixture or in the respective other isomeric form.

Including the various meanings (a), (b), (c), (d), (e), (f) and (g) of the group G, the following principal structures (I-8-a) to (I-8-g) result:

(I-8-a):
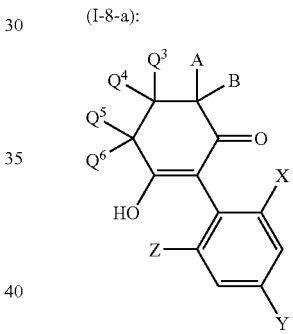

(I-8-b):
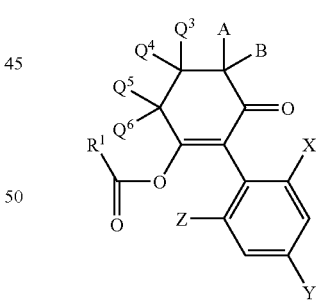

(I-8-c):
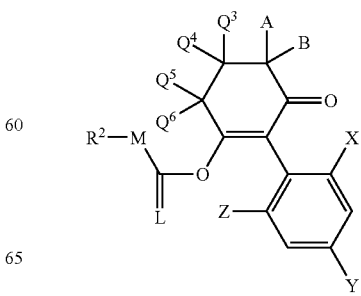

-continued (I-8-d):

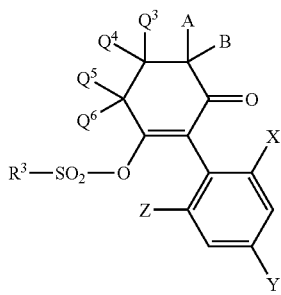

(I-8-e):

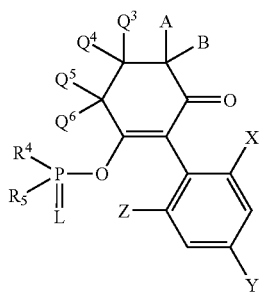

(I-8-f):

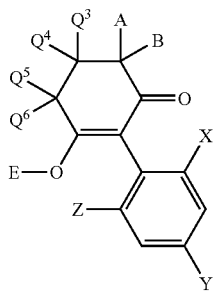

(I-8-g):

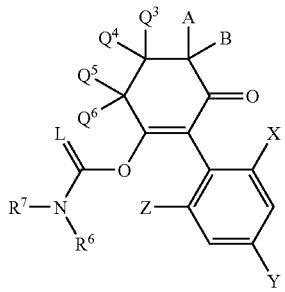

in which

A, B, E, L, M, $Q^3$, $Q^4$, $Q^5$, $Q^6$, X, Y, Z, $R^1$, $R^2$, $R^3$, $R^4$, $R^5$, $R^6$ and $R^7$ are each as defined above.

Furthermore, it has been found that the novel compounds of the formula (I) are obtained by one of the processes described below:

(A) Substituted 3-phenylpyrrolidine-2,4-diones or their enols of the formula (I-1-a)

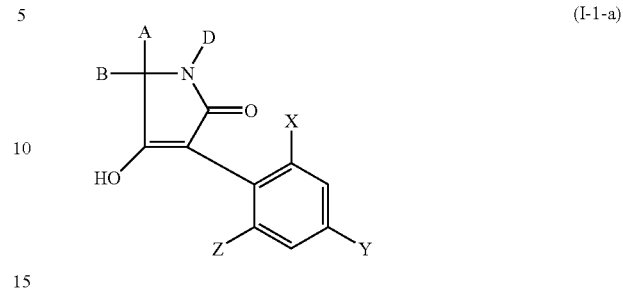

in which

A, B, D, X, Y and Z are each as defined above are obtained when

N-acylamino acid esters of the formula (II)

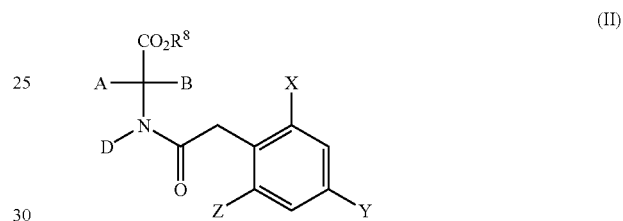

in which

A, B, D, X, Y and Z are each as defined above and $R^8$ represents alkyl (preferably $C_1$–$C_6$-alkyl)

are condensed intramolecularly in the presence of a diluent and in the presence of a base.

(B) Moreover, it has been found that substituted 3-phenyl-4-hydroxy-$\Delta^3$-dihydrofuranone derivatives of the formula (I-2-a)

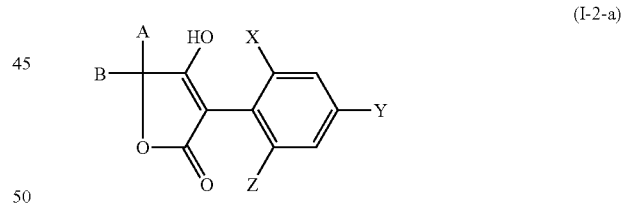

in which

A, B, X, Y and Z are each as defined above are obtained when carboxylic esters of the formula (III)

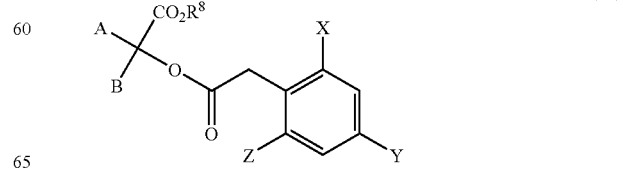

in which

A, B, X, Y, Z and $R^8$ are each as defined above
are condensed intramolecularly in the presence of a diluent and in the presence of a base.

(C) Furthermore, it has been found that substituted 3-phenyl-4-hydroxy-$\Delta^3$-dihydrothiophenone derivatives of the formula (I-3-a)

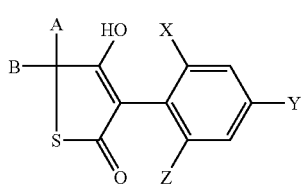

(I-3-a)

in which

A, B, X, Y and Z are each as defined above
are obtained when
β-ketocarboxylic esters of the formula (IV)

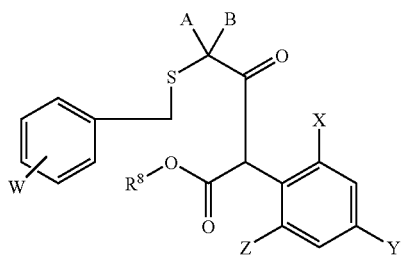

(IV)

in which

A, B, X, Y, Z and $R^8$ are each as defined above and
W represents hydrogen, halogen (preferably fluorine, chlorine, bromine), alkyl (preferably $C_1$–$C_6$-alkyl) or alkoxy (preferably $C_1$–$C_8$-alkoxy)
are cyclized intramolecularly, if appropriate in the presence of a diluent and in the presence of an acid.

(D) Furthermore, substituted 3-hydroxyl-4-phenyl-5-oxopyrazolines of the formula (I-4-a)

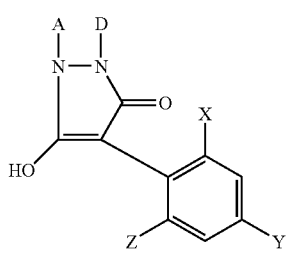

(I-4-a)

in which

A, D, X, Y and Z are each as defined above
are obtained when (α) halogenocarbonyl ketenes of the formula (V)

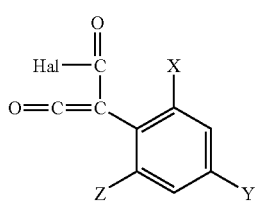

(V)

in which

X, Y and Z are each as defined above and
Hal represents halogen (in particular chlorine or bromine)
or (β) malonic acid derivatives of the formula (VI)

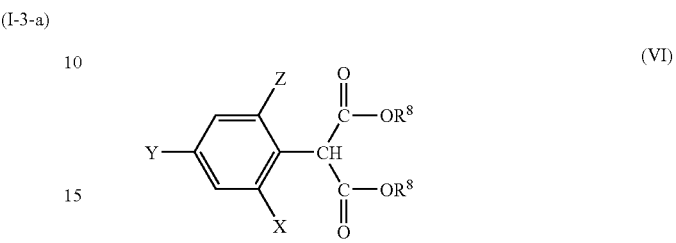

(VI)

in which $R^8$, X, Y and Z are each as defined above
are reacted with hydrazines of the formula (VII)

A-NH—NH-D    (VII)

in which

A and D are each as defined above
if appropriate in the presence of a diluent and if appropriate in the presence of a base.

(E) Furthermore, it has been found that the novel substituted 3-phenylpyrone derivatives of the formula (I-5-a)

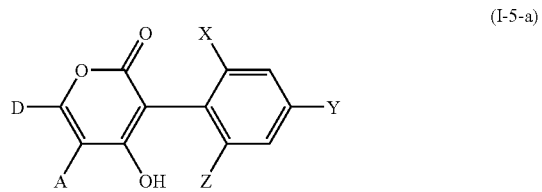

(I-5-a)

in which

A, D, X, Y and Z are each as defined above
are obtained when
carbonyl compounds of the formula (VIII)

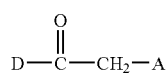

(VIII)

in which

A and D are each as defined above
or their silyl enol ethers of the formula (VIIIa)

$$D-\underset{\underset{}{\overset{\overset{CHA}{\|}}{C}}}{}-OSi(R^8)_3$$

(VIIIa)

in which

A, D and $R^8$ are each as defined above are reacted with ketene acid halides of the formula (V)

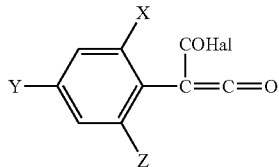
(V)

in which

X, Y and Z are each as defined above and

Hal represents halogen (preferably represents chlorine or bromine), if appropriate in the presence of a diluent and if appropriate in the presence of an acid acceptor.

Furthermore, it has been found (F) that the novel substituted phenyl-1,3-thiazine derivatives of the formula (I-6-a)

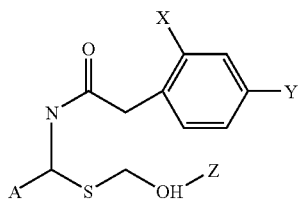
(I-6-a)

in which

A, X, Y and Z are each as defined above are obtained when thioamides of the formula (IX)

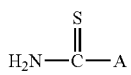
(IX)

in which

A is as defined above are reacted with ketene acid halides of the formula (V)

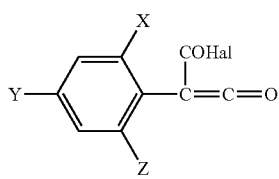
(V)

in which

Hal, X, Y and Z are each as defined above, if appropriate in the presence of a diluent and if appropriate in the presence of an acid acceptor.

Furthermore, it has been found (G) that compounds of the formula (I-7-a)

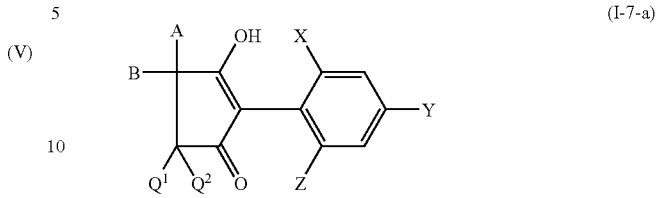
(I-7-a)

in which

A, B, $Q^1$, $Q^2$, X, Y and Z are each as defined above are obtained when ketocarboxylic esters of the formula (X)

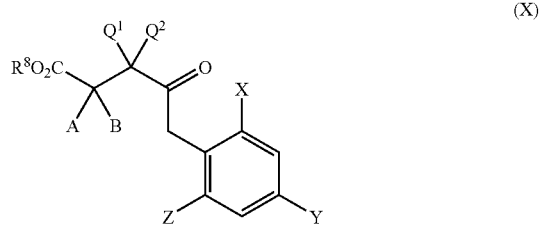
(X)

in which

A, B, $Q^1$, $Q^2$, X, Y and Z are each as defined above and $R^8$ represents alkyl (in particular $C_1$–$C_8$-alkyl)

are cyclized intramolecularly, if appropriate in the presence of a diluent and in the presence of a base.

Moreover, it has been found (H) that compounds of the formula (I-8-a)

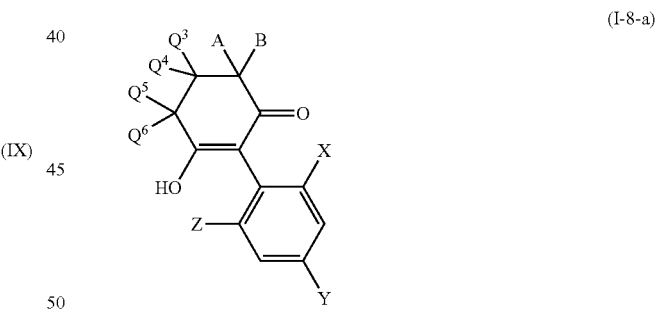
(I-8-a)

in which

A, B, $Q^3$, $Q^4$, $Q^5$, $Q^6$, X, Y and Z are each as defined above are obtained when 6-aryl-5-keto-hexanoic esters of the formula (XI)

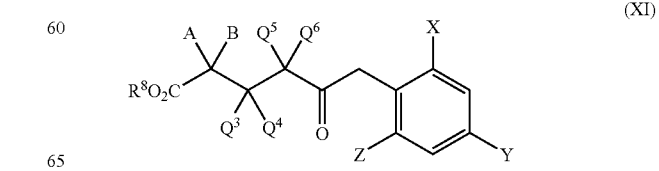
(XI)

in which
A, B, Q³, Q⁴, Q⁵, Q⁶, X, Y and Z are each as defined above and

R⁸ represents alkyl (preferably $C_1$–$C_6$-alkyl)

are condensed intramolecularly in the presence of a diluent and in the presence of a base; or (I) that compounds of the formulae (I-1-a) to (I-8-a) shown above in which A, B, D, Q¹, Q², Q³, Q⁴, Q⁵, Q⁶, X, Y and Z are each as defined above are obtained when compounds of the formula (I-1'-a) to (I-8'-a), (I-1'-a):

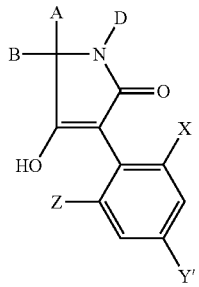

(I-2'-a):

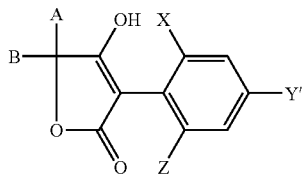

(I-3'-a):

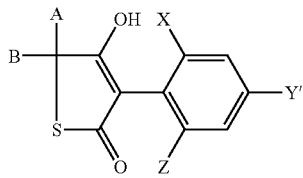

(I-4'-a):

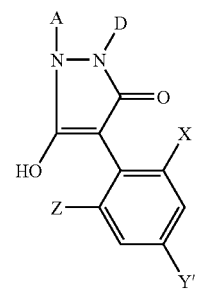

(I-5'-a):

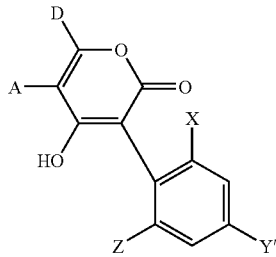

(I-6'-a):

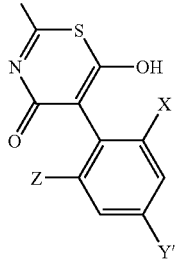

(I-7'-a):

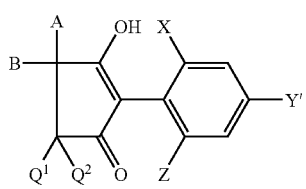

(I-8-a):

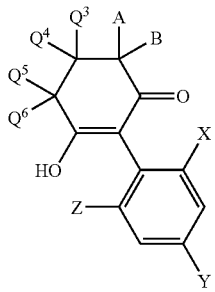

in which
A, B, D, Q¹, Q², Q³, Q⁴, Q⁵, Q⁶, X and Z are each as defined above and

Y' represents chlorine, bromine or iodine, preferably represents bromine, are reacted with boronic acids of the formula (XII)

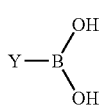

(XII)

in which
Y is as defined above in the presence of a solvent, a base and a catalyst, suitable catalysts being, in particular, palladium complexes.

Moreover, it has been found (J) that the compounds of the formulae (I-1-b) to (I-8-b) shown above in which A, B, D, Q¹, Q², Q³, Q⁴, Q⁵, Q⁶, R¹, X, Y and Z are each as defined above are obtained when compounds of the formulae (I-1-a) to (I-8-a) shown above in which A, B, D, Q¹, Q², Q³, Q⁴, Q⁵, Q⁶, X, Y and Z are each as defined above are in each case (α) reacted with acyl halides of the formula (XIII)

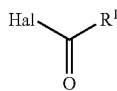 (XIII)

in which
R¹ is as defined above and
Hal represents halogen (in particular chlorine or bromine)
or (β) reacted with carboxylic anhydrides of the formula (XIV)

R¹—CO—O—CO—R¹ (XIV)

in which
R¹ is as defined above,
if appropriate in the presence of a diluent and if appropriate in the presence of an acid binder;

(K) that the compounds of the formulae (I-1-c) to (I-8-c) shown above in which A, B, D, Q¹, Q², Q³, Q⁴, Q⁵, Q⁶, R², M, X, Y and Z are each as defined above and L represents oxygen are obtained when compounds of the formulae (I-1-a) to (I-8-a) shown above in which A, B, D, Q¹, Q², Q³, Q⁴, Q⁵, Q⁶, X, Y and Z are each as defined above are in each case
reacted with chloroformic esters or chloroformic thioesters of the formula (XV)

R²-M-CO—Cl (XV)

in which
R² and M are each as defined above,
if appropriate in the presence of a diluent and if appropriate in the presence of an acid binder;

(L) that compounds of the formulae (I-1-c) to (I-8-c) shown above in which A, B, D, Q¹, Q², Q³, Q⁴, Q⁵, Q⁶, R², M, X, Y and Z are each as defined above and L represents sulphur are obtained when compounds of the formulae (I-1-a) to (I-8-a) shown above in which A, B, D, Q¹, Q², Q³, Q⁴, Q⁵, Q⁶, X, Y and Z are each as defined above are in each case reacted with chloromonothioformic esters or chlorodithioformic esters of the formula (XVI)

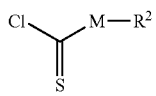 (XVI)

in which
M and R² are each as defined above
if appropriate in the presence of a diluent and if appropriate in the presence of an acid binder and (M) that compounds of the formulae (I-1-d) to (I-8-d) shown above in which A, B, D, Q¹, Q², Q³, Q⁴, Q⁵, Q⁶, R³, X, Y and Z are each as defined above are obtained when compounds of the formulae (I-1-a) to (I-8-a) shown above in which A, B, D, Q¹, Q², Q³, Q⁴, Q⁵, Q⁶, X, Y and Z are each as defined above are in each case
reacted with sulphonyl chlorides of the formula (XVII)

R³—SO₂—Cl (XVII)

in which
R³ is as defined above,
if appropriate in the presence of a diluent and if appropriate in the presence of an acid binder, (N) that compounds of the formulae (I-1-e) to (I-8-e) shown above in which A, B, D, L, Q¹, Q², Q³, Q⁴, Q⁵, Q⁶, R⁴, R⁵, X, Y and Z are each as defined above are obtained when compounds of the formulae (I-1-a) to (I-8-a) shown above in which A, B, D, Q¹, Q², Q³, Q⁴, Q⁵, Q⁶, X, Y and Z are each as defined above are in each case
reacted with phosphorus compounds of the formula (XVIII)

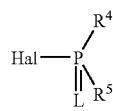 (XVIII)

in which
L, R⁴ and R⁵ are each as defined above and
Hal represents halogen (in particular chlorine or bromine),
if appropriate in the presence of a diluent and if appropriate in the presence of an acid binder, (L) that compounds of the formulae (I-1-f) to (I-8-f) shown above in which A, B, D, E, Q¹, Q², Q³, Q⁴, Q⁵, Q⁶, X, Y and Z are each as defined above are obtained when compounds of the formulae (I-1-a) to (I-8-a) in which A, B, D, Q¹, Q², Q³, Q⁴, Q⁵, Q⁶, X, Y and Z are each as defined above are in each case
reacted with metal compounds or amines of the formulae (XIX) or (XX)

Me(OR¹⁰)ₜ (XIX)

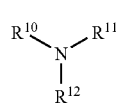 (XX)

in which
Me represents a mono- or divalent metal (preferably an alkali metal or alkaline earth metal, such as lithium, sodium, potassium, magnesium or calcium),
t represents the number 1 or 2 and
R¹⁰, R¹¹, R¹² independently of one another each represent hydrogen or alkyl (preferably C₁–C₈-alkyl),
if appropriate in the presence of a diluent, (P) that compounds of the formulae (I-1-g) to (I-8-g) shown above in which A, B, D, L, Q¹, Q², Q³, Q⁴, Qs, Q⁶, R⁶, R⁷, X, Y and Z are each as defined above are obtained when compounds of the formulae (I-1-a) to (I-8-a) shown above in which A, B, D, Q¹, Q², Q³, Q⁴, Q⁵, Q⁶, X, Y and Z are each as defined above are in each case (α) reacted with isocyanates or isothiocyanates of the formula (XXI)

R⁶—N=C=L (XXI)

in which
R⁶ and L are each as defined above
if appropriate in the presence of a diluent and if appropriate in the presence of a catalyst, or (β) reacted with carbamoyl chlorides or thiocarbamoyl chlorides of the formula (XXII)

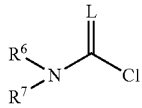
(XXII)

in which

L, $R^6$ and $R^7$ are each as defined above if appropriate in the presence of a diluent and if appropriate in the presence of an acid binder.

Furthermore, it has been found that the novel compounds of the formula (I) have very good activity as pesticides, preferably as insecticides, acaricides and also as herbicides.

The formula (I) provides a general definition of the compounds according to the invention. Preferred substituents or ranges of the radicals listed in the formulae mentioned hereinabove and hereinbelow are illustrated below:

X preferably represents halogen, $C_1$–$C_6$-alkyl, $C_1$–$C_6$-halogenoalkyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkoxy, $C_3$–$C_6$-halogenoalkenyloxy, nitro, cyano or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, benzyloxy or benzylthio.

Y preferably represents one of the radicals

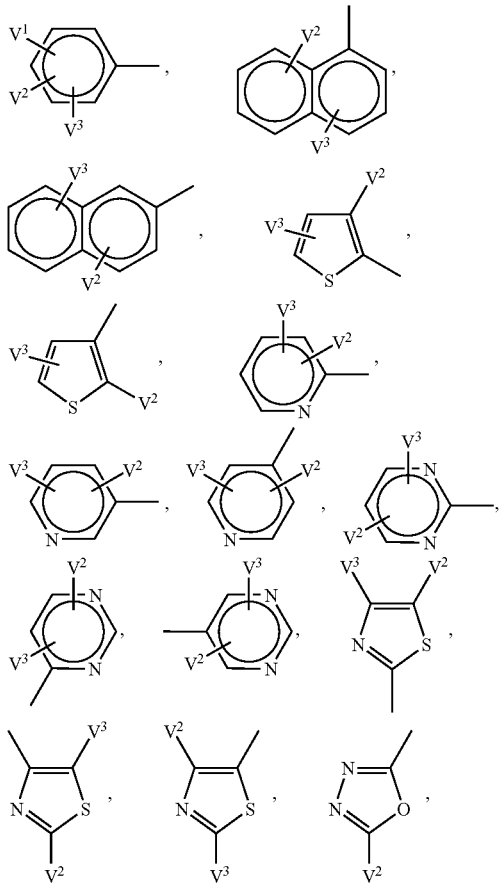

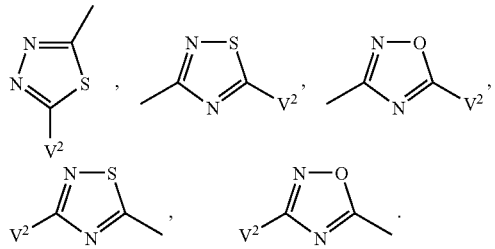

$V^1$ preferably represents hydrogen, halogen, $C_1$–$C_{12}$-alkyl, $C_1$–$C_6$-alkoxy, $C_1$–$C_4$-halogenoalky, $C_1$–$C_4$-halogenoalkoxy, nitro, cyano or phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$V^2$ and $V^3$ independently of one another each preferably represent hydrogen, halogen, $C_1$–$C_6$-alkyl, $C_1$–$C_6$-alkoxy, $C_1$–$C_4$-halogenoalkyl or $C_1$–$C_4$-halogenoalkoxy.

Z preferably represents hydrogen, halogen, $C_1$–$C_6$-alkyl, $C_1$–$C_6$-halogenoalkyl, $C_1$–$C_6$-alkoxy, $C_1$–$C_6$-halogenoalkoxy, nitro or cyano.

CKE preferably represents one of the groups

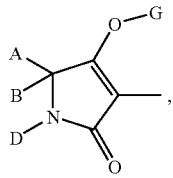
(1)

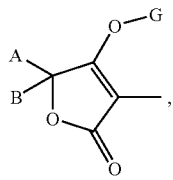
(2)

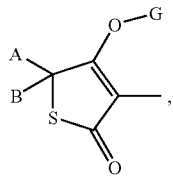
(3)

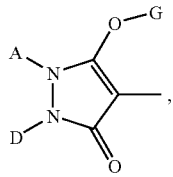
(4)

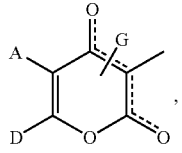
(5)

-continued

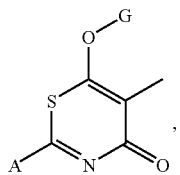
(6)

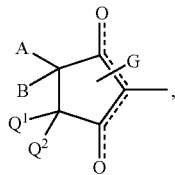
(7)

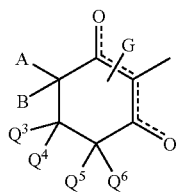
(8)

A preferably represents hydrogen or in each case optionally halogen-substituted $C_1$–$C_{12}$-alkyl, $C_3$–$C_8$-alkenyl, $C_1$–$C_{10}$-alkoxy-$C_1$–$C_8$-alkyl, poly-$C_1$–$C_8$-alkoxy-$C_1$–$C_8$-alkyl, $C_1$–$C_{10}$-alkylthio-$C_1$–$C_6$-alkyl, optionally halogen-, $C_1$–$C_6$-alkyl- or $C_1$–$C_6$-alkoxy-substituted $C_3$–$C_8$-cycloalkyl in which optionally one or two not directly adjacent ring members are replaced by oxygen and/or sulphur or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted $C_6$- or $C_{10}$-aryl (phenyl or naphthyl), hetaryl having 5 to 6 ring atoms (for example furanyl, pyridyl, imidazolyl, triazolyl, pyrazolyl, pyrimidyl, thiazolyl or thienyl) or $C_6$- or $C_{10}$-aryl-$C_1$–$C_6$-alkyl (phenyl-$C_1$–$C_6$-alkyl or naphthyl-$C_1$–$C_6$-alkyl).

B preferably represents hydrogen, $C_1$–$C_{12}$-alkyl or $C_1$–$C_8$-alkoxy-$C_1$–$C_6$-alkyl or A, B and the carbon atom to which they are attached preferably represent saturated $C_3$–$C_{10}$-cycloalkyl or unsaturated $C_5$–$C_{10}$-cycloalkyl in which optionally one ring member is replaced by oxygen or sulphur and which are optionally mono- or disubstituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the carbon atom to which they are attached preferably represent $C_3$–$C_6$-cycloalkyl which is substituted by an alkylenediyl group which optionally contains one or two not directly adjacent oxygen and/or sulphur atoms, or by an alkylenedioxyl group or by an alkylenedithioyl group which, together with the carbon atom to which it is attached, forms a further five- to eight-membered ring, or A, B and the carbon atom to which they are attached preferably represent $C_3$–$C_8$-cycloalkyl or $C_5$–$C_8$-cycloalkenyl, in which two substituents together with the carbon atoms to which they are attached represent in each case optionally $C_1$–$C_6$-alkyl-, $C_1$–$C_6$-alkoxy- or halogen-substituted $C_2$–$C_6$-alkanediyl, $C_2$–$C_6$-alkenediyl or $C_4$–$C_6$-alkanedienediyl in which optionally one methylene group is replaced by oxygen or sulphur.

D preferably represents hydrogen, in each case optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl, $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-halogenoalkyl-substituted $C_3$–$C_8$-cycloalkyl in which optionally one ring member is replaced by oxygen or sulphur or in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$–$C_6$-alkyl or hetaryl-$C_1$–$C_6$-alkyl having 5 or 6 ring atoms (for example furanyl-, imidazolyl-, pyridyl-, thiazolyl-, pyrazolyl-, pyrimidyl-, pyrrolyl-, thienyl- or triazolyl-$C_1$–$C_6$-alkyl), or A and D together preferably represent in each case optionally substituted $C_3$–$C_6$-alkanediyl or $C_3$–$C_6$-alkenediyl in which optionally one methylene group is replaced by oxygen or sulphur, possible substituents in each case being:

halogen, hydroxyl, mercapto or in each case optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy, or a further $C_3$–$C_6$-alkanediyl grouping, $C_3$–$C_6$-alkenediyl grouping or a butadienyl grouping which is optionally substituted by $C_1$–$C_6$-alkyl or in which optionally two adjacent substituents together with the carbon atoms to which they are attached form a further saturated or unsaturated cycle having 5 or 6 ring atoms (in the case of the compound of the formula (I-1), A and D, together with the atoms to which they are attached, then represent, for example, the groups AD-1 to AD-10 mentioned further below) which cycle may contain oxygen or sulphur, or which may optionally contain one of the groups below

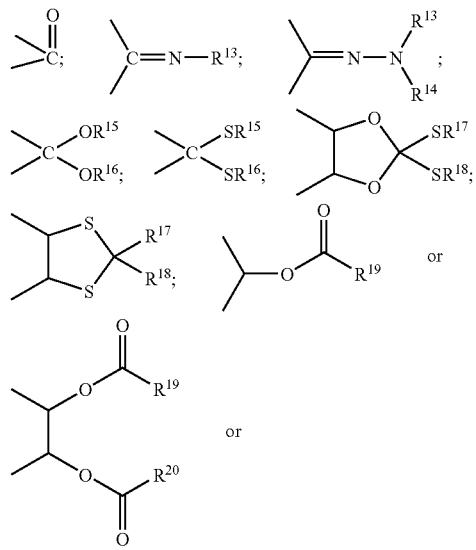

A and $Q^1$ together preferably represent $C_3$–$C_6$-alkanediyl or $C_4$–$C_6$-alkenediyl, each of which is optionally mono- or disubstituted by identical or different substituents selected from the group consisting of halogen, hydroxyl; $C_1$–$C_1$-alkyl, $C_1$–$C_6$-alkoxy, $C_1$–$C_6$-alkylthio, $C_3$–$C_7$-cycloalkyl, each of which is optionally mono- to trisubstituted by identical or different halogens; and benzyloxy and phenyl, each of which is optionally mono- to trisubstituted by identical or different substituents selected from the group consisting of halogen, $C_1$–$C_6$-alkyl or $C_1$–$C_6$-alkoxy, and which furthermore optionally contains one of the groups below

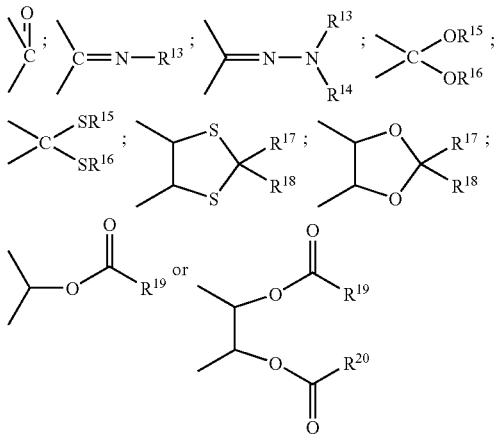

or is bridged by a $C_1$–$C_2$-alkanediyl group or by an oxygen atom, or $Q^1$ preferably represents hydrogen or $C_1$–$C_4$-alkyl.

$Q^2$, $Q^4$, $Q^5$ and $Q^6$ independently of one another each preferably represent hydrogen or $C_1$–$C_4$-alkyl, $Q^3$ preferably represents hydrogen, $C_1$–$C_6$-alkyl, $C_1$–$C_6$-alkoxy-$C_1$–$C_2$-alkyl, $C_1$–$C_6$-alkylthio-$C_1$–$C_2$-alkyl, optionally $C_1$–$C_4$-alkyl- or $C_1$–$C_4$-alkoxy-substituted $C_3$–$C_8$-cycloalkyl in which optionally one methylene group is replaced by oxygen or sulphur or optionally halogen-, $C_1$–$C_4$-alkyl-, $C_1$–$C_4$-alkoxy-, $C_1$–$C_2$-halogenoalkyl-, $C_1$–$C_2$-halogenoalkoxy-, cyano- or nitro-substituted phenyl, or $Q^3$ and $Q^4$ together with the carbon atom to which they are attached represent optionally $C_1$–$C_4$-alkyl-, $C_1$–$C_4$-alkoxy- or $C_1$–$C_2$-halogenoalkyl-substituted $C_3$–$C_7$-cycloalkyl in which optionally one ring member is replaced by oxygen or sulphur.

G preferably represents hydrogen (a) or represents one of the groups

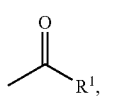 (b)

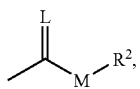 (c)

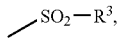 (d)

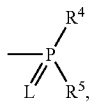 (e)

E or (f)

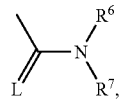 (g)

in particular represents (a), (b) or (c),
in which
E represents a metal ion or an ammonium ion,
L represents oxygen or sulphur and
M represents oxygen or sulphur.

$R^1$ preferably represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl or optionally halogen-, $C_1$–$C_6$-alkyl- or $C_1$–$C_6$-alkoxy-substituted $C_3$–$C_8$-cycloalkyl in which optionally one or more (preferably one or two) not directly adjacent ring members are replaced by oxygen and/or sulphur, represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, represents optionally halogen- or $C_1$–$C_6$-alkyl-substituted 5- or 6-membered hetaryl (for example pyrazolyl, thiazolyl, pyridyl, pyrimidyl, furanyl or thienyl), represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl (for example pyridyloxy-$C_1$–$C_6$-alkyl, pyrimidyloxy-$C_1$–$C_6$-alkyl or thiazolyloxy-$C_1$–$C_6$-alkyl).

$R^2$ preferably represents in each case optionally halogen-substituted $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl or represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl.

$R^3$ preferably represents optionally halogen-substituted $C_1$–$C_8$-alkyl or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl.

$R^4$ and $R^5$ independently of one another each preferably represent in each case optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio or represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio.

$R^6$ and $R^7$ independently of one another each preferably represent hydrogen, represent in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, represent optionally halogen-, $C_1$–$C_8$-halogenoalkyl-, $C_1$–$C_8$-alkyl- or $C_1$–$C_8$-alkoxy-substituted phenyl, optionally halogen-, $C_1$–$C_8$-alkyl-, $C_1$–$C_8$-halogenoalkyl- or $C_1$–$C_8$-alkoxy-substituted benzyl or together represent an optionally $C_1$–$C_4$-alkyl-substituted $C_3$–$C_6$-alkylene radical in which optionally one carbon atom is replaced by oxygen or sulphur.

$R^{13}$ preferably represents hydrogen, represents in each case optionally halogen-substituted $C_1$–$C_8$-alkyl or $C_1$–$C_8$-alkoxy, represents optionally halogen-, $C_1$–$C_4$-alkyl- or $C_1$–$C_4$-alkoxy-substituted $C_3$–$C_8$-cycloalkyl in which optionally one methylene group is replaced by oxygen or sulphur, or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy.

$R^{14}$ preferably represents hydrogen or $C_1$–$C_8$-alkyl, or $R^{13}$ and $R^{14}$ together preferably represent $C_4$–$C_6$-alkanediyl.

$R^{15}$ and $R^{16}$ are identical or different and each preferably represent $C_1$–$C_6$-alkyl, or $R^{15}$ and $R^{16}$ together preferably represent a $C_2$–$C_4$-alkanediyl radical which is optionally substituted by $C_1$–$C_6$-alkyl, $C_1$–$C_6$-halogenoalkyl or by optionally halogen-, $C_1$–$C_6$-alkyl-, $C_1$–$C_4$-halogenoalkyl-, $C_1$–$C_6$-alkoxy-, $C_1$–$C_4$-halogenoalkoxy-, nitro- or cyano-substituted phenyl.

$R^{17}$ and $R^{18}$ independently of one another each preferably represent hydrogen, represent optionally halogen-substituted $C_1$–$C_8$-alkyl or represent optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, or $R^{17}$ and $R^{18}$ together with the carbon atom to which they are attached preferably represent a carbonyl group or represent optionally halogen-, $C_1$–$C_4$-alkyl- or $C_1$–$C_4$-alkoxy-substituted $C_5$–$C_7$-cycloalkyl in which optionally one methylene group is replaced by oxygen or sulphur.

$R^{19}$ and $R^{20}$ independently of one another each preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

In the preferred radical definitions, halogen, including as substituent, such as, for example, in halogenoalkyl, represents fluorine, chlorine, bromine and iodine and in particular represents fluorine and chlorine.

X particularly preferably represents fluorine, chlorine, bromine, $C_1$–$C_4$-alkyl, $C_1$–$C_4$-alkoxy, $C_3$–$C_4$-alkenyloxy, $C_1$–$C_4$-halogenoalkyl, $C_1$–$C_4$-halogenoalkoxy, $C_3$–$C_4$-halogenoalkenyloxy, nitro or cyano.

Y particularly preferably represents one of the radicals

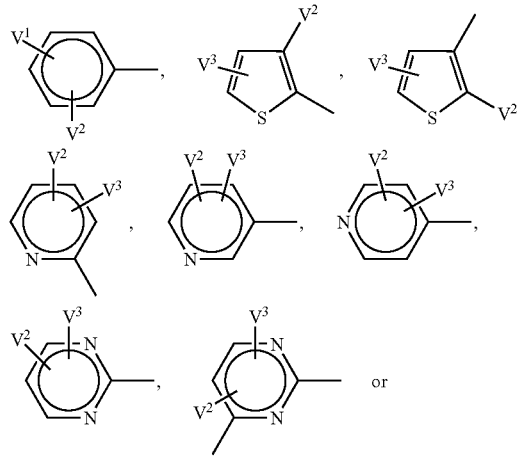

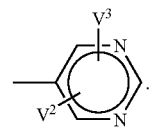

$V^1$ particularly preferably represents hydrogen, fluorine, chlorine, bromine, $C_1$–$C_6$-alkyl, $C_1$–$C_4$-alkoxy, $C_1$–$C_2$-halogenoalkyl, $C_1$–$C_2$-halogenoalkoxy, nitro, cyano or phenyl, phenoxy, phenoxy-$C_1$–$C_2$-alkyl, phenyl-$C_1$–$C_2$-alkoxy, phenylthio-$C_1$–$C_2$-alkyl or phenyl-$C_1$–$C_2$-alkylthio, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

$V^2$ and $V^3$ independently of one another each particularly preferably represent hydrogen, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy.

Z particularly preferably represents hydrogen, fluorine, chlorine, bromine, $C_1$–$C_4$-alkyl, $C_1$–$C_4$-halogenoalkyl, $C_1$–$C_4$-alkoxy or $C_1$–$C_4$-halogenoalkoxy.

CKE particularly preferably represents one of the groups

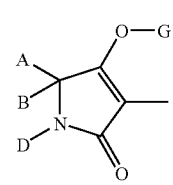

(1)

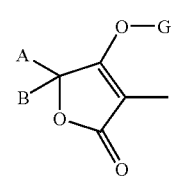

(2)

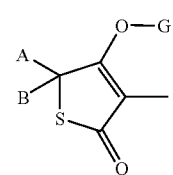

(3)

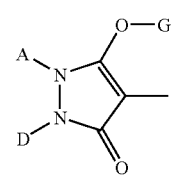

(4)

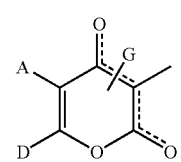

(5)

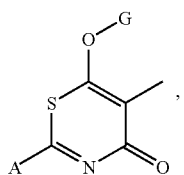
(6)

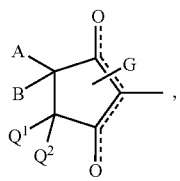
(7)

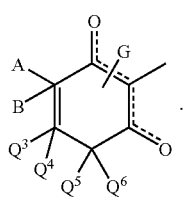
(8)

A particularly preferably represents hydrogen, in each case optionally fluorine- or chlorine-substituted $C_1$–$C_{10}$-alkyl, $C_1$–$C_8$-alkoxy-$C_1$–$C_6$-alkyl, optionally fluorine-, chlorine-, $C_1$–$C_4$-alkyl- or $C_1$–$C_4$-alkoxy-substituted $C_3$–$C_7$-cycloalkyl in which optionally one ring member is replaced by oxygen or sulphur or (but not in the case of the compounds of the formulae (I-5), (I-7) and (I-8)) in each case optionally fluorine-, chlorine-, bromine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, furanyl, pyridyl, imidazolyl, triazolyl, pyrazolyl, pyrimidyl, thiazolyl, thienyl or phenyl-$C_1$–$C_4$-alkyl.

B particularly preferably represents hydrogen or $C_1$–$C_6$-alkyl, or

A, B and the carbon atom to which they are attached particularly preferably represent saturated or unsaturated $C_5$–$C_7$-cycloalkyl in which optionally one ring member is replaced by oxygen or sulphur and which is optionally monosubstituted by $C_1$–$C_6$-alkyl, $C_5$–$C_8$-cycloalkyl, $C_1$–$C_3$-halogenoalkyl, $C_1$–$C_6$-alkoxy, fluorine, chlorine or phenyl, or A, B and the carbon atom to which they are attached particularly preferably represent $C_5$–$C_6$-cycloalkyl which is substituted by an alkylenediyl group which optionally contains one or two not directly adjacent oxygen or sulphur atoms or by an alkylenedioxyl group or by an alkylenedithiol group which, together with the carbon atom to which it is attached, forms a further five- or six-membered ring, or A, B and the carbon atom to which they are attached particularly preferably represent $C_3$–$C_6$-cycloalkyl or $C_5$–$C_6$-cycloalkenyl in which two substituents together with the carbon atoms to which they are attached represent in each case optionally $C_1$–$C_5$-alkyl-, $C_1$–$C_5$-alkoxy-, fluorine-, chlorine- or bromine-substituted $C_2$–$C_4$-alkanediyl, $C_2$–$C_4$-alkenediyl, in which optionally one methylene group is replaced by oxygen or sulphur, or butadienediyl.

D particularly preferably represents hydrogen, represents in each case optionally fluorine- or chlorine-substituted $C_1$–$C_{10}$-alkyl, $C_3$–$C_6$-alkenyl, $C_1$–$C_8$-alkoxy-$C_2$–$C_6$-alkyl or $C_1$–$C_8$-alkylthio-$C_2$–$C_6$-alkyl, represents optionally fluorine-, chlorine-, $C_1$–$C_4$-alkyl-, $C_1$–$C_4$-alkoxy- or $C_1$–$C_2$-halogenoalkyl-substituted $C_3$–$C_7$-cycloalkyl in which optionally one methylene group is replaced by oxygen or sulphur or (but not in the case of the compounds of the formulae (I-1) and (I-4)) represents in each case optionally fluorine-, chlorine-, bromine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, furanyl, imidazolyl, pyridyl, thiazolyl, pyrazolyl, pyrimidyl, pyrrolyl, thienyl, triazolyl or phenyl-$C_1$–$C_4$-alkyl, or A and D together particularly preferably represent optionally substituted $C_3$–$C_5$-alkanediyl in which one methylene group may be replaced by a carbonyl group, oxygen or sulphur, possible substituents being hydroxyl, $C_1$–$C_6$-alkyl or $C_1$–$C_4$-alkoxy, or A and D (in the case of the compounds of the formula (I-1)) together with the atoms to which they are attached represent one of the groups AD-1 to AD-10:

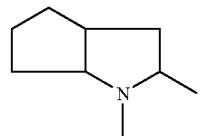
AD-1

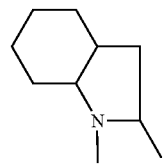
AD-2

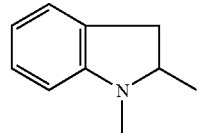
AD-3

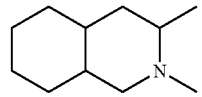
AD-4

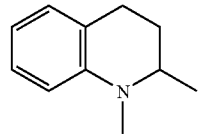
AD-5

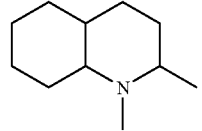
AD-6

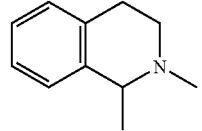
AD-7

-continued

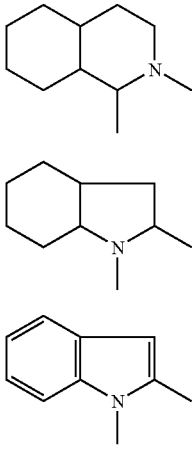

AD-8

AD-9

AD-10

A and $Q^1$ together particularly preferably represent $C_3$–$C_4$-alkanediyl or $C_3$–$C_4$-alkenediyl, each of which is optionally mono- or disubstituted by identical or different substituents selected from the group consisting of fluorine, chlorine, hydroxyl, and $C_1$–$C_8$-alkyl and $C_1$–$C_4$-alkoxy, each of which is optionally mono- to trisubstituted by fluorine, or $Q^1$ particularly preferably represents hydrogen.

$Q^2$ particularly preferably represents hydrogen.

$Q^4$, $Q^5$ and $Q^6$ independently of one another each particularly preferably represent hydrogen or $C_1$–$C_3$-alkyl.

$Q^3$ particularly preferably represents hydrogen, $C_1$–$C_4$-alkyl, $C_1$–$C_4$-alkoxy-$C_1$–$C_2$-alkyl, $C_1$–$C_4$-alkylthio-$C_1$–$C_2$-alkyl or optionally methyl- or methoxy-substituted $C_3$–$C_6$-cycloalkyl in which optionally one methylene group is replaced by oxygen or sulphur, or $Q^3$ and $Q^4$ together with the carbon atom to which they are attached particularly preferably represent an optionally $C_1$–$C_4$-alkyl- or $C_1$–$C_4$-alkoxy-substituted saturated $C_5$–$C_6$-cycloalkyl in which optionally one ring member is replaced by oxygen or sulphur.

G particularly preferably represents hydrogen (a) or particularly preferably represents one of the groups

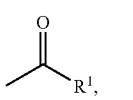 (b)

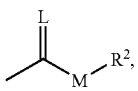 (c)

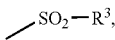 (d)

(e)

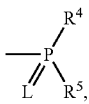 (f)

E or

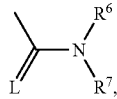 (g)

in particular represents (a), (b) or (c),
in which
E represents a metal ion or an ammonium ion,
L represents oxygen or sulphur and
M represents oxygen or sulphur.

$R^1$ particularly preferably represents in each case optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, poly-$C_1$–$C_6$-alkoxy-$C_1$–$C_6$-alkyl or optionally fluorine-, chlorine-, $C_1$–$C_5$-alkyl- or $C_1$–$C_5$-alkoxy-substituted $C_3$–$C_7$-cycloalkyl in which optionally one or two not directly adjacent ring members are replaced by oxygen and/or sulphur, represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, represents in each case optionally fluorine-, chlorine-, bromine- or $C_1$–$C_4$-alkyl-substituted pyrazolyl, thiazolyl, pyridyl, pyrimidyl, furanyl or thienyl, represents optionally fluorine-, chlorine-, bromine- or $C_1$–$C_4$-alkyl-substituted phenoxy-$C_1$–$C_3$-alkyl or represents in each case optionally fluorine-, chlorine-, bromine-, amino- or $C_1$–$C_4$-alkyl-substituted pyridyloxy-$C_1$–$C_3$-alkyl, pyrimidyloxy-$C_1$–$C_3$-alkyl or thiazolyloxy-$C_1$–$C_3$-alkyl.

$R^2$ particularly preferably represents in each case optionally fluorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents optionally fluorine-, chlorine-, $C_1$–$C_4$-alkyl- or $C_1$–$C_4$-alkoxy-substituted $C_3$–$C_7$-cycloalkyl or represents in each case optionally fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl, $R^3$ particularly preferably represents optionally fluorine-substituted $C_1$–$C_6$-alkyl or particularly preferably represents in each case optionally fluorine-, chlorine-, bromine-, $C_1$–$C_4$-alkyl-, $C_1$–$C_4$-alkoxy-, $C_1$–$C_3$-halogenoalkyl-, $C_1$–$C_3$-halogenoalkoxy-, cyano- or nitro-substituted phenyl or benzyl, $R^4$ and $R^5$ independently of one another each particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio, $C_3$–$C_6$-cycloalkylthio or represent in each case optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio, and $R^6$ and $R^7$ independently of one another each particularly preferably represent hydrogen, $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, represent optionally fluorine-, chlorine-, bromine-, $C_1$–$C_3$-halogenoalkyl-, $C_1$–$C_4$-alkyl- or $C_1$–$C_4$-alkoxy-substituted phenyl, represent optionally fluorine-, chlorine-, bromine-, $C_1$–$C_4$-alkyl-, $C_1$–$C_3$-halogenoalkyl- or $C_1$–$C_4$-alkoxy-substituted benzyl, or together represent an optionally methyl- or ethyl-substituted $C_4$–$C_5$-alkylene radical in which optionally one methylene group is replaced by oxygen or sulphur.

In the particularly preferred radical definitions, halogen, including as substituent, such as, for example, in halogenoalkyl, represents fluorine, chlorine, bromine and iodine, in particular represents fluorine, chlorine and bromine and very particularly represents fluorine or chlorine.

X very particularly preferably represents fluorine, chlorine, methyl, ethyl, n-propyl, iso-propyl, methoxy, ethoxy, n-propoxy, iso-propoxy, trifluoromethyl, difluoromethoxy, trifluoromethoxy, nitro or cyano (with emphasis on fluorine, chlorine, methyl, ethyl, n-propyl or iso-propyl).

Y very particularly preferably represents one of the radicals

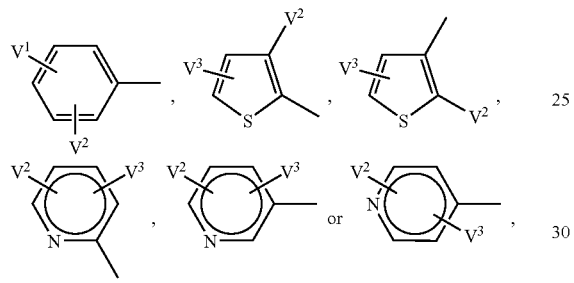

in particular represents

$V^1$ very particularly preferably represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, nitro, cyano or phenyl.

$V^2$ and $V^3$ independently of one another each very particularly preferably represent hydrogen, fluorine, chlorine, methyl, ethyl, n-propyl, iso-propyl, methoxy, ethoxy, trifluoromethyl or trifluoromethoxy.

Z very particularly preferably represents hydrogen, fluorine, chlorine, methyl, ethyl, n-propyl, methoxy, ethoxy or n-propoxy (with emphasis on hydrogen, fluorine, chlorine, methyl, ethyl or n-propyl).

CKE very particularly preferably represents one of the groups

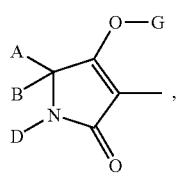 (1)

-continued

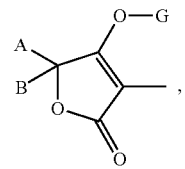 (2)

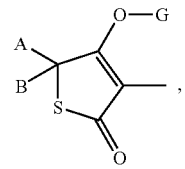 (3)

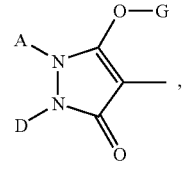 (4)

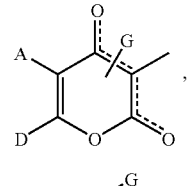 (5)

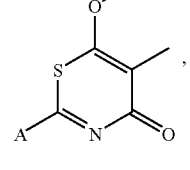 (6)

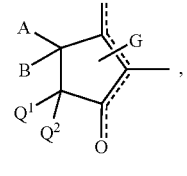 (7)

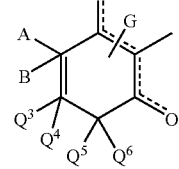 (8)

A very particularly preferably represents hydrogen, in each case optionally fluorine-substituted $C_1$–$C_8$-alkyl or $C_1$–$C_6$-alkoxy-$C_1$–$C_4$-alkyl, optionally fluorine-, methyl-, ethyl- or methoxy-substituted $C_3$–$C_6$-cycloalkyl in which optionally one ring member is replaced by oxygen or sulphur or (but not in the case of the compounds of the formulae (I-5), (I-7) and (I-8)) represents in each case optionally fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl or benzyl.

B very particularly preferably represents $C_1$–$C_4$-alkyl, or

A, B and the carbon atom to which they are attached very particularly preferably represent saturated $C_5$–$C_6$-cycloalkyl in which optionally one ring member is replaced by oxygen or sulphur and which is optionally monosubstituted by methyl, ethyl, n-propyl, isopropyl, butyl, isobutyl, sec-butyl, tert-butyl, trifluoromethyl, methoxy, ethoxy, n-propoxy, iso-propoxy, n-butoxy, isobutoxy, sec-butoxy, tert-butoxy, fluorine or chlorine, or A, B and the carbon atom to which they are attached very particularly preferably represent $C_5$–$C_6$-cycloalkyl in which two substituents together with the carbon atoms to which they are attached represent $C_2$–$C_4$-alkanediyl or $C_2$–$C_4$-alkenediyl in which in each case optionally one methylene group is replaced by oxygen or sulphur, or butadienediyl.

D very particularly preferably represents hydrogen, represents in each case optionally fluorine- or chlorine-substituted $C_1$–$C_8$-alkyl, $C_3$–$C_4$-alkenyl, $C_1$–$C_6$-alkoxy-$C_2$–$C_4$-alkyl, $C_1$–$C_4$-alkylthio-$C_2$–$C_4$-alkyl or $C_3$–$C_6$-cycloalkyl in which optionally one methylene group is replaced by oxygen or sulphur or (but not in the case of the compounds of the formulae (I-1) and (I-4)) represents in each case optionally fluorine-, chlorine-, methyl-, ethyl-, n-propyl-, iso-propyl-, methoxy-, ethoxy-, trifluoromethyl- or trifluoromethoxy-substituted phenyl, furanyl, pyridyl, thienyl or benzyl (in compounds of the formula (I-1) with emphasis on hydrogen), or A and D together very particularly preferably represent optionally substituted $C_3$–$C_4$-alkanediyl in which optionally one carbon atom is replaced by sulphur and which is optionally substituted by hydroxyl, methyl, ethyl, methoxy or ethoxy, or A and D (in the case of the compounds of the formula (I-1)) together with the atoms to which they are attached represent one of the following groups AD:

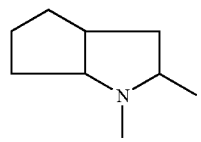

AD-1

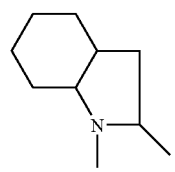

AD-2

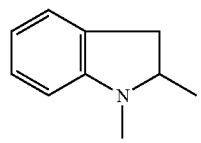

AD-3

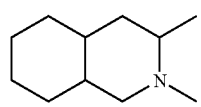

AD-4

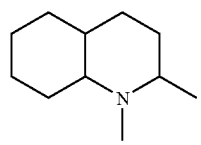

AD-6

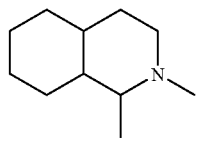

AD-8

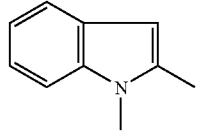

AD-10

A and $Q^1$ together very particularly preferably represent $C_3$–$C_4$-alkanediyl or butenediyl, each of which is optionally mono- or disubstituted by fluorine, hydroxyl, methyl or methoxy, or $Q^1$ very particularly preferably represents hydrogen.

$Q^2$ very particularly preferably represents hydrogen.

$Q^4$, $Q^5$ and $Q^6$ independently of one another each very particularly preferably represent hydrogen, methyl or ethyl.

$Q^3$ very particularly preferably represents hydrogen, methyl, ethyl or $C_3$–$C_6$-cycloalkyl in which optionally one methylene group is replaced by oxygen or sulphur (with emphasis on hydrogen, methyl or ethyl), or $Q^3$ and $Q^4$ together with the carbon to which they are attached very particularly preferably represent optionally methyl- or methoxy-substituted saturated $C_5$–$C_6$-cycloalkyl in which optionally one ring member is replaced by oxygen or sulphur.

G very particularly preferably represents hydrogen (a) or represents one of the groups

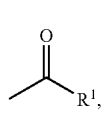

(b)

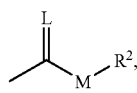

(c)

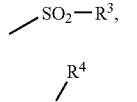

(d)

(e)

E or (f)

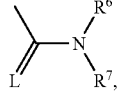

(g)

in particular represents (a), (b) or (c),
in which
E represents a metal ion or an ammonium ion,
L represents oxygen or sulphur and
M represents oxygen or sulphur.

$R^1$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl $C_1$–$C_4$-alkylthio-$C_1$–$C_6$-alkyl, poly-$C_1$–$C_4$-alkoxy-$C_1$–$C_4$-alkyl or optionally fluorine-, chlorine-, methyl-, ethyl-, n-propyl-, i-propyl-, n-butyl-, i-butyl-, tert-butyl-, methoxy-, ethoxy-, n-propoxy- or iso-propoxy-substituted $C_3$–$C_6$-cycloalkyl in which optionally one or two not directly adjacent ring members are replaced by oxygen and/or sulphur, represents optionally fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl, represents optionally fluorine-, chlorine-, bromine-, methyl-, ethyl-, n-propyl-, i-propyl-, methoxy-, ethoxy-, trifluoromethyl- or trifluoromethoxy-substituted benzyl, represents in each case optionally fluorine-, chlorine-, bromine-, methyl- or ethyl-substituted furanyl, thienyl, pyridyl, pyrimidyl, thiazolyl or pyrazolyl, represents optionally fluorine-, chlorine-, methyl- or ethyl-substituted phenoxy-$C_1$–$C_2$-alkyl or represents in each case optionally fluorine-, chlorine-, amino-, methyl- or ethyl-substituted pyridyloxy-$C_1$–$C_2$-alkyl, pyrimidyloxy-$C_1$–$C_2$-alkyl or thiazolyloxy-$C_1$–$C_2$-alkyl.

$R^2$ very particularly preferably represents in each case optionally fluorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, represents optionally fluorine-, chlorine-, methyl-, ethyl-, n-propyl-, isopropyl- or methoxy-substituted $C_3$–$C_6$-cycloalkyl, or represents in each case optionally fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl.

$R^3$ very particularly preferably represents in each case optionally fluorine-substituted methyl, ethyl, n-propyl, isopropyl or in each case optionally fluorine-, chlorine-, bromine-, methyl-, tert-butyl-, methoxy-, trifluoromethyl-, trifluoromethoxy-, cyano- or nitro-substituted phenyl or benzyl, $R^4$ and $R^5$ independently of one another each very particularly preferably represent $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio or represent in each case optionally fluorine-, chlorine-, bromine-, nitro-, cyano-, $C_1$–$C_2$-alkoxy-, $C_1$–$C_2$-fluoroalkoxy-, $C_1$–$C_2$-alkylthio-, $C_1$–$C_2$-fluoroalkylthio- or $C_1$–$C_3$-alkyl-substituted phenyl, phenoxy or phenylthio.

$R^6$ and $R^7$ independently of one another each very particularly preferably represent hydrogen, represent $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, represent optionally fluorine-, chlorine-, bromine-, trifluoromethyl-, methyl- or methoxy-substituted phenyl, represent optionally fluorine-, chlorine-, bromine-, methyl-, trifluoromethyl- or methoxy-substituted benzyl, or together represent a $C_5$–$C_6$-alkylene radical in which optionally one methylene group is replaced by oxygen or sulphur.

The abovementioned general or preferred radical definitions or illustrations can be combined with each other as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Compounds of the formula (I) in which G represents hydrogen are particularly preferred.

Saturated or unsaturated hydrocarbon radicals such as alkyl or alkenyl may in each case be straight-chain or branched as far as this is possible, including in combination with heteroatoms, such as, for example, in alkoxy.

Unless stated otherwise, optionally substituted radicals may be mono- or polysubstituted, and in the case of polysubstitutions the substituents may be identical or different.

Besides the compounds mentioned in the Preparation Examples, the following compounds of the formula (I-1-a) may be specifically mentioned:

TABLE 1

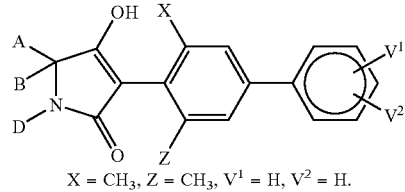

$X = CH_3, Z = CH_3, V^1 = H, V^2 = H.$

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| △— | $CH_3$ | H |
| ⬠— | $CH_3$ | H |
| ⬡— | $CH_3$ | H |
| —(CH$_2$)$_2$— | | H |
| —(CH$_2$)$_4$— | | H |
| —(CH$_2$)$_5$— | | H |

TABLE 1-continued

Structure: Pyrrolinone with OH, X, Z substituents on aryl, linked to biphenyl with V¹, V² substituents; A-B-N-D ring with carbonyl.

X = CH₃, Z = CH₃, V¹ = H, V² = H.

| A-B-D (combined) | B |
|---|---|
| —(CH₂)₆— | H |
| —(CH₂)₇— | H |
| —(CH₂)₂—O—(CH₂)₂— | H |
| —CH₂—O—(CH₂)₃— | H |
| —(CH₂)₂—S—(CH₂)₂— | H |
| —CH₂—CHCH₃—(CH₂)₃— | H |
| —(CH₂)₂—CHCH₃—(CH₂)₂— | H |
| —(CH₂)₂—CHC₂H₅—(CH₂)₂— | H |
| —(CH₂)₂—CHC₃H₇—(CH₂)₂— | H |
| —(CH₂)₂—CHi-C₃H₇—(CH₂)₂— | H |
| —(CH₂)₂—CHOCH₃—(CH₂)₂— | H |
| —(CH₂)₂—CHOC₂H₅—(CH₂)₂— | H |
| —(CH₂)₂—CHOC₃H₇—(CH₂)₂— | H |
| —(CH₂)₂—CHi-C₃H₇—(CH₂)₂— | H |
| —(CH₂)₂—C(CH₃)₂—(CH₂)₂— | H |
| —CH₂—(CHCH₃)₂—(CH₂)₂— | H |
| —CH₂—CH—(CH₂)₂—CH— with —CH₂— bridge | H |
| —CH₂—CH—CH—CH₂— with —(CH₂)₄— bridge | H |
| —CH₂—CH—CH—(CH₂)₂— with —(CH₂)₃— bridge | H |
| indane (fused bicyclic) | H |
| tetrahydronaphthalene (fused bicyclic) | H |

| A | D | B |
|---|---|---|
| —(CH₂)₃— | | H |
| —(CH₂)₄— | | H |
| —CH₂—CHCH₃—CH₂— | | H |
| —CH₂—CH₂—CHCH₃— | | H |
| —CH₂—CHCH₃—CHCH₃— | | H |
| —CH₂—S—CH₂— | | H |
| —CH₂—S—(CH₂)₂— | | H |
| —(CH₂)₂—S—CH₂— | | H |
| —CH₂—CH—CH— with —(CH₂)₃— bridge | | H |
| H | CH₃ | H |
| H | C₂H₅ | H |
| H | C₃H₇ | H |
| H | i-C₃H₇ | H |
| H | cyclopropyl | H |
| H | cyclopentyl-methyl | H |

TABLE 1-continued

X = CH₃, Z = CH₃, V¹ = H, V² = H.

| A | D | B |
|---|---|---|
| H | cyclohexyl-methyl | H |
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | cyclopentyl-methyl | H |
| CH₃ | cyclohexyl-methyl | H |
| C₂H₅ | CH₃ | H |
| C₂H₅ | C₂H₅ | H |

TABLE 2

A, B and D are each as given in Table 1
X = C₂H₅; Z = CH₃; V¹ = H; V² = H.

TABLE 3

A, B and D are each as given in Table 1
X = C₂H₅; Z = C₂H₅; V¹ = H; V² = H.

TABLE 4

A, B and D are each as given in Table 1
X = CH₃; Z = CH₃; V¹ = 4-Cl; V² = H.

TABLE 5

A, B and D are each as given in Table 1
X = C₂H₅; Z = CH₃; V¹ = 4-Cl; V² = H.

TABLE 6

A, B and D are each as given in Table 1
X = C₂H₅; Z = C₂H₅; V¹ = 4-Cl; V² = H.

TABLE 7

A, B and D are each as given in Table 1
X = CH₃; Z = CH₃; V¹ = 3-Cl; V² = H.

TABLE 8

A, B and D are each as given in Table 1
X = $C_2H_5$; Z = $CH_3$; $V^1$ = 3-Cl; $V^2$ = H.

TABLE 9

A, B and D are each as given in Table 1
X = $C_2H_5$; Z = $C_2H_5$; $V^1$ = 3-Cl; $V^2$ = H.

TABLE 10

A, B and D are each as given in Table 1
X = $CH_3$; Z = $CH_3$; $V^1$ = 2-Cl; $V^2$ = 4-Cl.

TABLE 11

A, B and D are each as given in Table 1
X = $C_2H_5$; Z = $CH_3$; $V^1$ = 2-Cl; $V^2$ = 4-Cl.

TABLE 12

A, B and D are each as given in Table 1
X = $C_2H_5$; Z = $C_2H_5$; $V^1$ = 2-Cl; $V^2$ = 4-Cl.

TABLE 13

A, B and D are each as given in Table 1
X = $CH_3$; Z = $CH_3$; $V^1$ = 4-$CF_3$; $V^2$ = H.

TABLE 14

A, B and D are each as given in Table 1
X = $C_2H_5$; Z = $CH_3$; $V^1$ = 4-$CF_3$; $V^2$ = H.

TABLE 15

A, B and D are each as given in Table 1
X = $C_2H_5$; Z = $C_2H_5$; $V^1$ = 4-$CF_3$; $V^2$ = H.

TABLE 16

A, B and D are each as given in Table 1
X = $CH_3$; Z = $CH_3$; $V^1$ = 4-$CH_3$; $V^2$ = H.

TABLE 17

A, B and D are each as given in Table 1
X = $C_2H_5$; Z = $CH_3$; $V^1$ = 4-$CH_3$; $V^2$ = H.

TABLE 18

A, B and D are each as given in Table 1
X = $C_2H_5$; Z = $C_2H_5$; $V^1$ = 4-$CH_3$; $V^2$ = H.

TABLE 19

A, B and D are each as given in Table 1
X = $CH_3$; Z = $CH_3$; $V^1$ = 4-$OCH_3$; $V^2$ = H.

TABLE 20

A, B and D are each as given in Table 1
X = $C_2H_5$; Z = $CH_3$; $V^1$ = 4-$OCH_3$; $V^2$ = H.

TABLE 21

A, B and D are each as given in Table 1
X = $C_2H_5$; Z = $C_2H_5$; $V^1$ = 4-$OCH_3$; $V^2$ = H.

Besides the compounds mentioned in the Preparation Examples, the following compounds of the formula (I-2-a) may be specifically mentioned:

TABLE 22

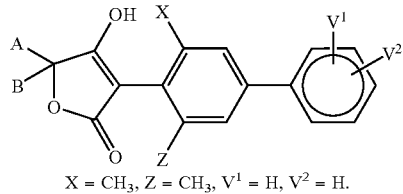

X = $CH_3$, Z = $CH_3$, $V^1$ = H, $V^2$ = H.

| A | B |
|---|---|
| $CH_3$ | H |
| $C_2H_5$ | H |
| $C_3H_7$ | H |
| i-$C_3H_7$ | H |
| $C_4H_9$ | H |
| i-$C_4H_9$ | H |
| s-$C_4H_9$ | H |
| t-$C_4H_9$ | H |
| $CH_3$ | $CH_3$ |
| $C_2H_5$ | $CH_3$ |
| $C_3H_7$ | $CH_3$ |
| i-$C_3H_7$ | $CH_3$ |
| $C_4H_9$ | $CH_3$ |
| i-$C_4H_9$ | $CH_3$ |
| s-$C_4H_9$ | $CH_3$ |
| t-$C_4H_9$ | $CH_3$ |
| $C_2H_5$ | $C_2H_5$ |
| $C_3H_7$ | $C_3H_7$ |
| cyclopropyl | $CH_3$ |
| cyclopentyl | $CH_3$ |
| cyclohexyl | $CH_3$ |
| —$(CH_2)_2$— | |
| —$(CH_2)_4$— | |
| —$(CH_2)_5$— | |
| —$(CH_2)_6$— | |
| —$(CH_2)_7$— | |
| —$(CH_2)_2$—O—$(CH_2)_2$— | |
| —$CH_2$—O—$(CH_2)_3$— | |
| —$(CH_2)_2$—S—$(CH_2)_2$— | |
| —$CH_2$—$CHCH_3$—$(CH_2)_3$— | |
| —$(CH_2)_2$—$CHCH_3$—$(CH_2)_2$— | |

TABLE 22-continued

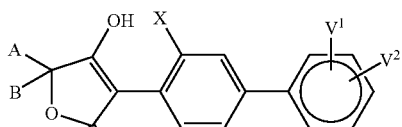

X = CH₃, Z = CH₃, V¹ = H, V² = H.

| A | B |
|---|---|

—(CH₂)₂—CHC₂H₅—(CH₂)₂—
—(CH₂)₂—CHC₃H₇—(CH₂)₂—
—(CH₂)₂—CHi—C₃H₇—(CH₂)₂—
—(CH₂)₂—CHOCH₃—(CH₂)₂—
—(CH₂)₂—CHOC₂H₅—(CH₂)₂—
—(CH₂)₂—CHOC₃H₇—(CH₂)₂—
—(CH₂)₂—CHi-C₃H₇—(CH₂)₂—
—(CH₂)₂—C(CH₃)₂—(CH₂)₂—
—CH₂—(CHCH₃)₂—(CH₂)₂—

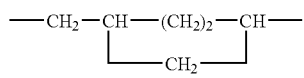

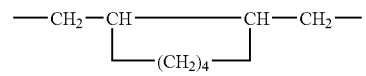

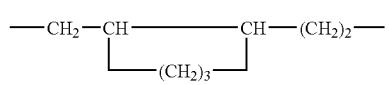

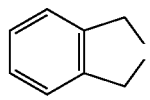

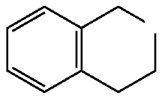

TABLE 23

A and B are each as given in Table 22
X = C₂H₅; Z = CH₃; V¹ = H; V² = H.

TABLE 24

A and B are each as given in Table 22
X = C₂H₅; Z = C₂H₅; V¹ = H; V² = H.

TABLE 25

A and B are each as given in Table 22
X = CH₃; Z = CH₃; V¹ = 4-Cl; V² = H.

TABLE 26

A and B are each as given in Table 22
X = C₂H₅; Z = CH₃; V¹ = 4-Cl; V² = H.

TABLE 27

A and B are each as given in Table 22
X = C₂H₅; Z = C₂H₅; V¹ = 4-Cl; V² = H.

TABLE 28

A and B are each as given in Table 22
X = CH₃; Z = CH₃; V¹ = 3-Cl; V² = H.

TABLE 29

A and B are each as given in Table 22
X = C₂H₅; Z = CH₃; V¹ = 3-Cl; V² = H.

TABLE 30

A and B are each as given in Table 22
X = C₂H₅; Z = C₂H₅; V¹ = 3-Cl; V² = H.

TABLE 31

A and B are each as given in Table 22
X = CH₃; Z = CH₃; V¹ = 4-CF₃; V² = H.

TABLE 32

A and B are each as given in Table 22
X = C₂H₅; Z = CH₃; V¹ = 4-CF₃; V² = H.

TABLE 33

A and B are each as given in Table 22
X = C₂H₅; Z = C₂H₅; V¹ = 4-CF₃; V² = H.

TABLE 34

A and B are each as given in Table 22
X = CH₃; Z = CH₃; V¹ = 2-Cl; V² = 4-Cl.

TABLE 35

A and B are each as given in Table 22
X = C₂H₅; Z = CH₃; V¹ = 2-Cl; V² = 4-Cl.

TABLE 36

A and B are each as given in Table 22
X = C₂H₅; Z = C₂H₅; V¹ = 2-Cl; V¹ = 4-Cl.

TABLE 37

A and B are each as given in Table 22
X = CH₃; Z = CH₃; V¹ = 4-CH₃; V² = H.

TABLE 38

A and B are each as given in Table 22
$X = C_2H_5; Z = CH_3; V^1 = 4\text{-}CH_3; V^2 = H.$

TABLE 39

A and B are each as given in Table 22
$X = C_2H_5; Z = C_2H_5; V^1 = 4\text{-}CH_3; V^2 = H.$

TABLE 40

A and B are each as given in Table 22
$X = CH_3; Z = CH_3; V^1 = 4\text{-}OCH_3; V^2 = H.$

TABLE 41

A and B are each as given in Table 22
$X = C_2H_5; Z = CH_3; V^1 = 4\text{-}OCH_3; V^2 = H.$

TABLE 42

A and B are each as given in Table 22
$X = C_2H_5; Z = C_2H_5; V^1 = 4\text{-}OCH_3; V^2 = H.$ Using, in accordance with process (A), ethyl N-[(2-methyl-4-phenyl)-phenylacetyl]-1-amino-cyclohexane-carboxylate as starting material, the course of the process according to the invention can be represented by the following equation:

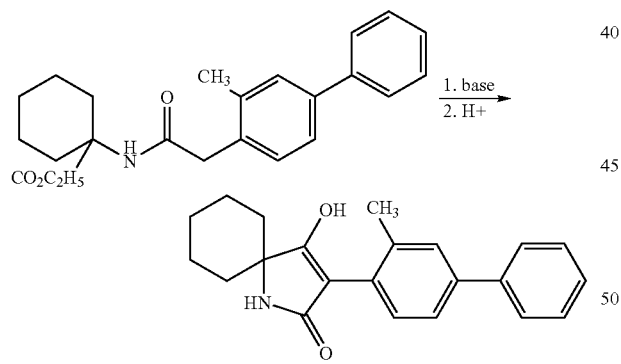

Using, in accordance with process (B), ethyl (B)O-[(2-chloro-4-(4-chloro)-phenyl)phenylacetyl]-2-hydroxyisobutyrate, the course of the process according to the invention can be represented by the following equation:

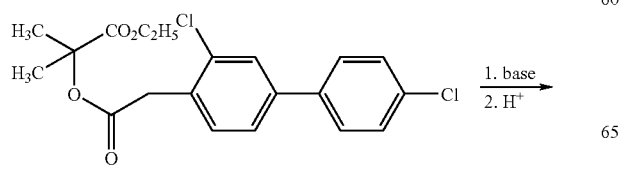

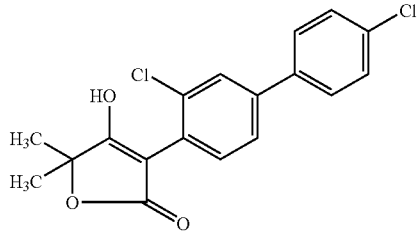

Using, in accordance with process (C), ethyl 2-[(2,6-dimethyl-4-phenyl)-phenyl]-4-(4-methoxy)-benzylmercapto-4-methyl-3-oxo-valerate, the course of the process according to the invention can be represented by the following equation:

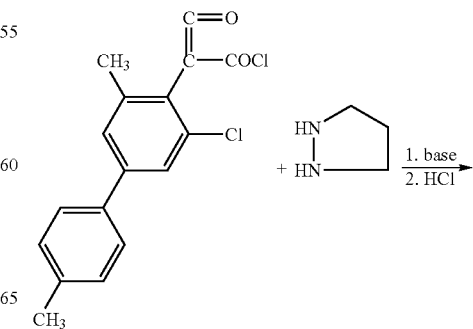

Using, for example in accordance with process (D-α), chlorocarbonyl 3-[(2-chloro-6-methyl-4-(4-methyl)-phenyl)-phenyl] ketene and 1,2-diazacyclopentane as starting materials, the course of the process according to the invention can be represented by the following equation:

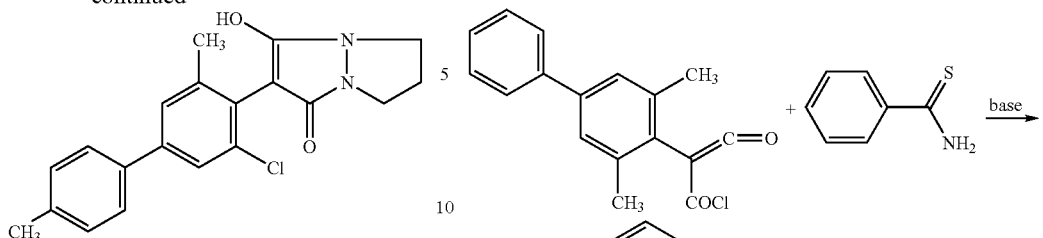

Using, for example in accordance with process (D-β), diethyl 3-[2-methyl-4-(3-chloro-phenyl)]-phenylmalonate and 1,2-diazacyclopentane as starting materials, the course of the process according to the invention can be represented by the following equation:

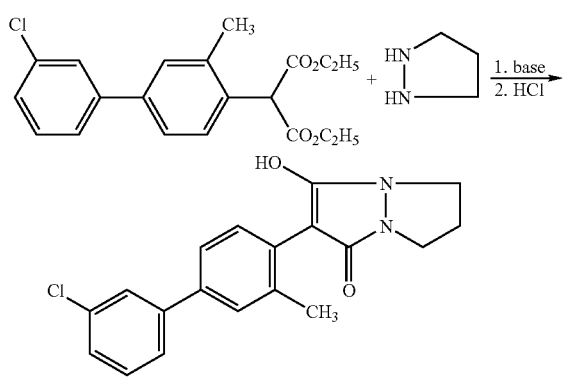

Using, for example in accordance with process (E), chlorocarbonyl 2-[(2-ethyl-6-methyl-(4-trifluoromethoxy-phenyl))-phenyl] ketene and acetone as starting materials, the course of the process according to the invention can be represented by the following equation:

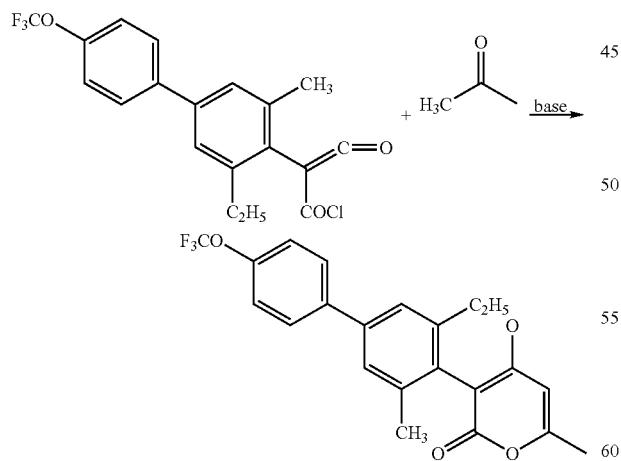

Using, for example in accordance with process (F), chlorocarbonyl 2-[(2,6-dimethyl-4-phenyl)-phenyl] ketene and thiobenzamide as starting materials, the course of the process according to the invention can be represented by the following equation:

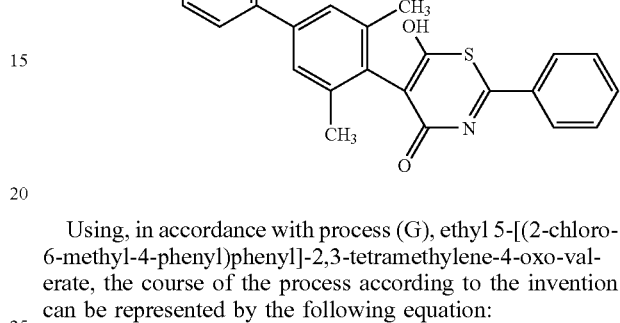

Using, in accordance with process (G), ethyl 5-[(2-chloro-6-methyl-4-phenyl)phenyl]-2,3-tetramethylene-4-oxo-valerate, the course of the process according to the invention can be represented by the following equation:

Using, in accordance with process (H), ethyl 5-[(2,6-dichloro-4-phenyl)-phenyl]-2,2-dimethyl-5-oxo-hexanoate, the course of the process according to the invention can be represented by the following equation:

Using, in accordance with process (I), 3-[(2,6-dimethyl-4-bromo)-phenyl]-4,4-(pentamethylene)-pyrrolidine-2,4-dione and 4-chlorophenylboronic acid as starting materials, the course of the reaction can be represented by the following scheme:

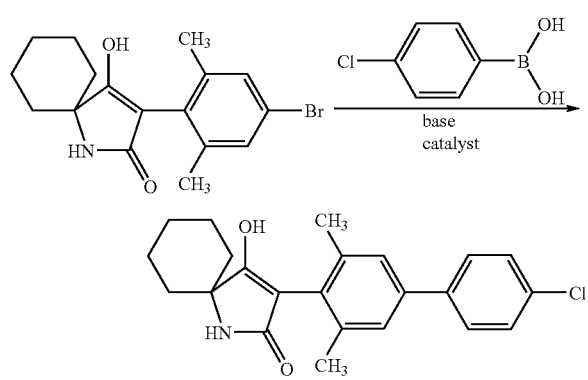

Using, in accordance with process (Jα), 3-[(2-chloro-4-(3-chloro-phenyl))-phenyl]-5,5-dimethylpyrrolidine-2,4-dione and pivaloyl chloride as starting materials, the course of the process according to the invention can be represented by the following equation:

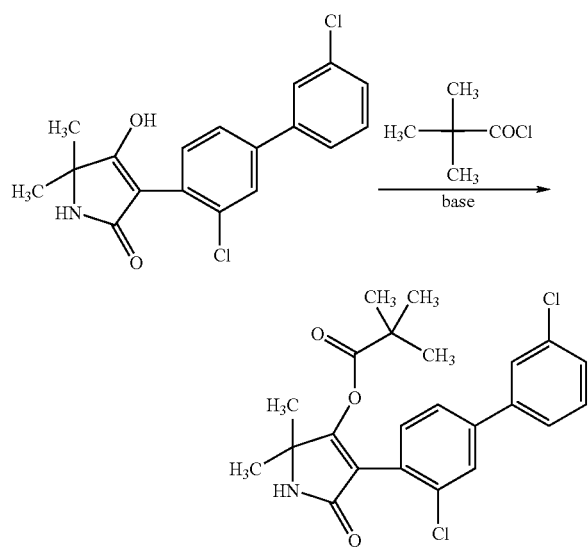

Using, in accordance with process (J), (variant β), 3-[(2-ethyl-4-(4-methoxyphenyl))-phenyl]4-hydroxy-5-phenyl-Δ³-dihydrofuran-2-one and acetic anhydride as starting materials, the course of the process according to the invention can be represented by the following equation:

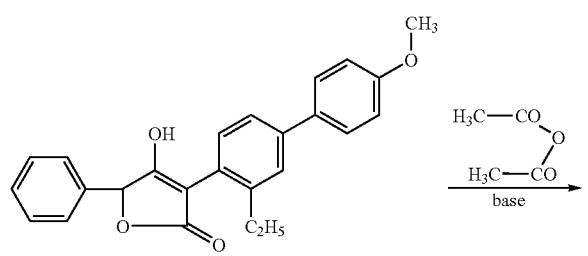

-continued

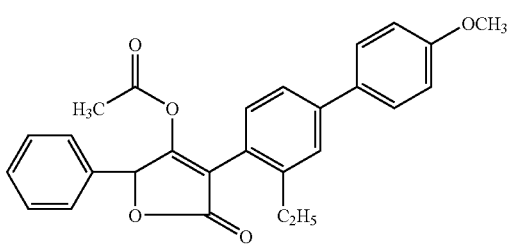

Using, in accordance with process (K), 8-[(2,6-diethyl-4-phenyl)-phenyl]-1,6-diazabicyclo-(4.3.0$^{1.6}$)-nonane-7,9-dione and ethoxyethyl chloroformate as starting materials, the course of the process according to the invention can be represented by the following equation:

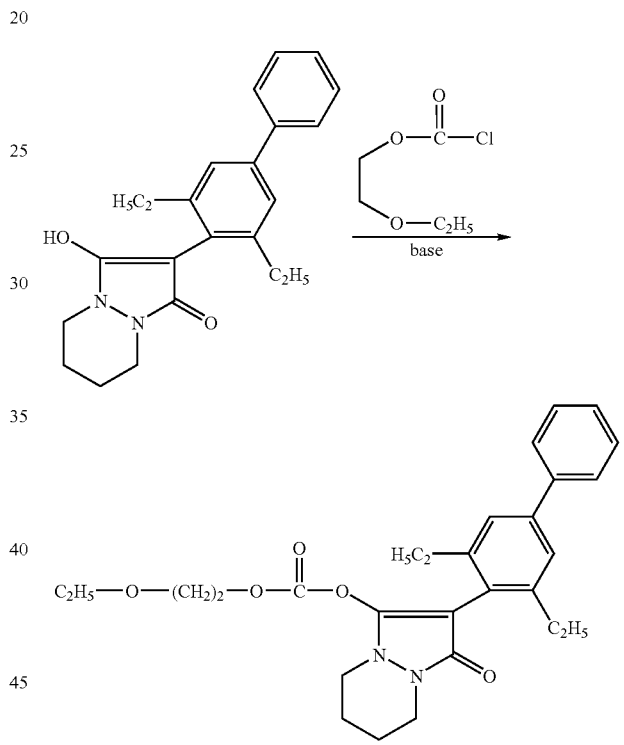

Using, in accordance with process (L), 3-[(2-chloro-4-(4-fluoro-phenyl))-phenyl]-4-hydroxy-5-methyl-6-(3-pyridyl)-pyrone and methyl chloromonothioformate as starting materials, the course of the reaction can be represented as follows:

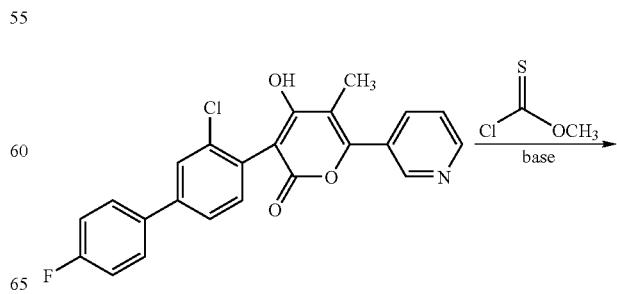

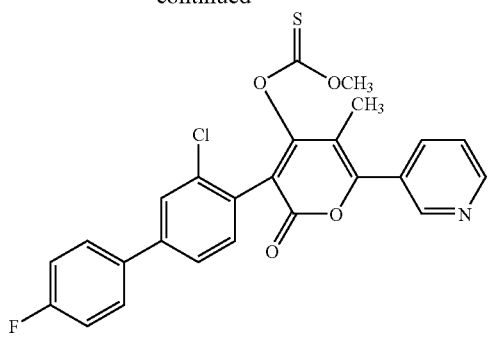

Using, in accordance with process (M), 2-[(2,6-dimethyl-4-(4-methyl-phenyl))-phenyl]-5,5-pentamethylene-pyrrolidine-2,4-dione and methanesulphonyl chloride as starting materials, the course of the reaction can be represented by the following equation:

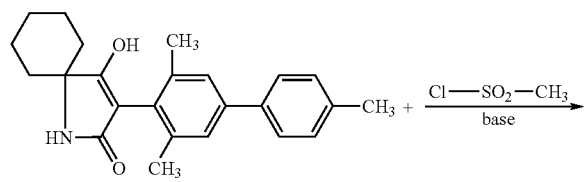

Using, in accordance with process (N), 2-[(2-methyl-4-phenyl)-phenyl]-4-hydroxy-5,5-dimethyl-$\Delta^3$-dihydrofuran-2-one and 2,2,2-trifluoroethyl methanethiophosphonyl chloride as starting materials, the course of the reaction can be represented by the following equation:

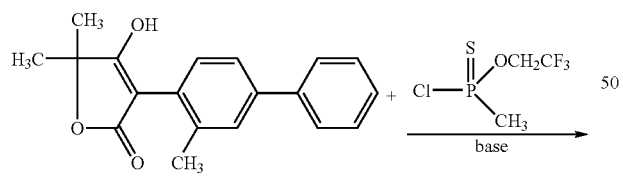

Using, in accordance with process (O), 3-[(2-trifluoromethyl-4-(4-(4-trifluoromethylphenyl))-phenyl]-5-cyclopropyl-5-methyl-pyrrolidine-2,4-dione and NaOH as components, the course of the process according to the invention can be represented by the following equation:

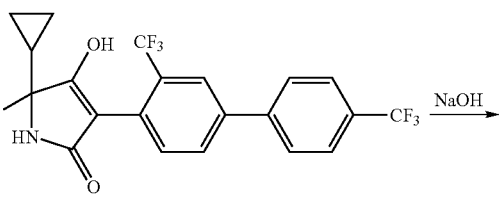

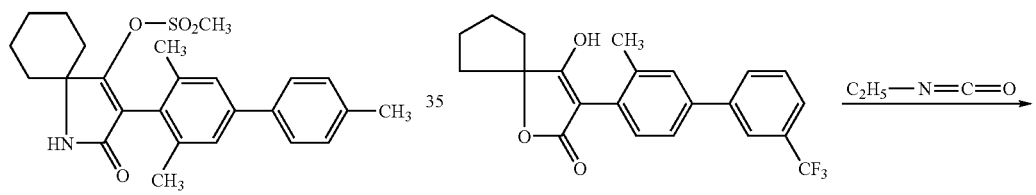

Using, in accordance with process (P), variant α, 3-[(2-methyl-4-(3-trifluoromethylphenyl))-phenyl]-4-hydroxy-5-tetramethylene-$\Delta^3$-dihydro-furan-2-one and ethyl isocyanate as starting materials, the course of the reaction can be represented by the following equation:

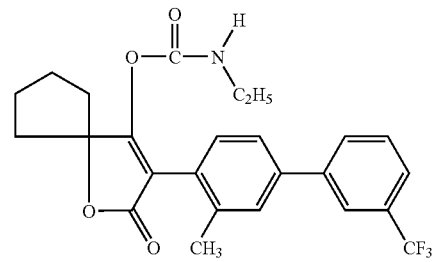

Using, in accordance with process (P), variant β, 3-[(2-chloro-4-phenyl)-phenyl]-5-methyl-pyrrolidine-2,4-dione and dimethylcarbamoyl chloride as starting materials, the course of the reaction can be represented by the following scheme:

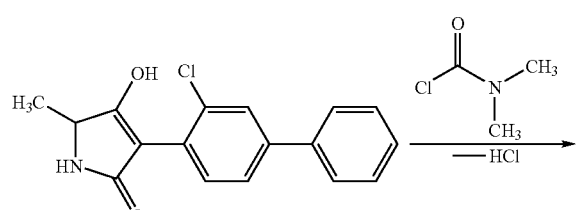

-continued

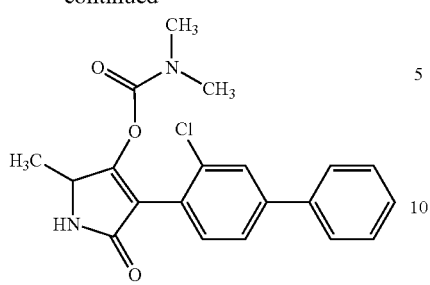

The compounds of the formula (II)

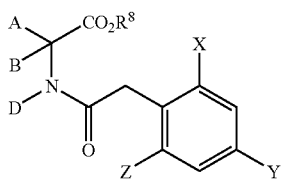
(II)

in which

A, B, D, X, Y, Z and $R^8$ are each as defined above which are required as starting materials in the process (a) according to the invention are novel.

The acylamino acid esters of the formula (II) are obtained, for example, when amino acid derivatives of the formula (XXIII)

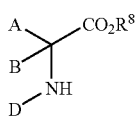
(XXIII)

in which

A, B, $R^8$ and D are each as defined above are acylated with substituted phenylacetyl halides of the formula (XXIV)

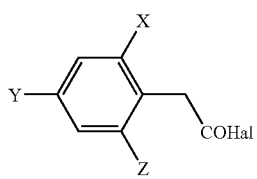
(XXIV)

in which

X, Y and Z are each as defined above and

Hal represents chlorine or bromine (Chem. Reviews 52, 237–416 (1953); Bhattacharya, Indian J. Chem. 6, 341–5, 1968) or when acylamino acids of the formula (XXV)

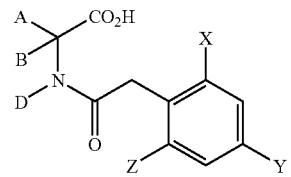
(XXV)

in which

A, B, D, X, Y and Z are each as defined above are esterified (Chem. Ind. (London) 1568 (1968)).

The compounds of the formula (XXV)

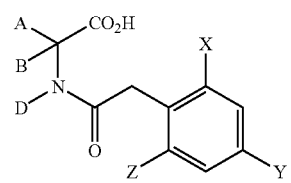
(XXV)

in which

A, B, D, X, Y and Z are each as defined above are novel.

The compounds of the formula (XXV) are obtained when amino acids of the formula (XXVI)

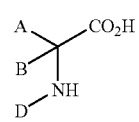
(XXVI)

in which

A, B and D are each as defined above are acylated with substituted phenylacetyl halides of the formula (XXIV)

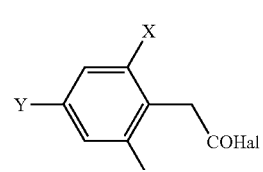
(XXIV)

in which

X, Y and Z are each as defined above and

Hal represents chlorine or bromine, for example according to Schotten-Baumann (Organikum, VEB Deutscher Verlag der Wissenschaften, Berlin 1977, p. 505).

The compounds of the formula (XXIV) are novel. They can be prepared by processses which are known in principle (see, for example, H. Henecka, Houben-Weyl, Methoden der Organischen Chemie, Vol. 8, p. 467–469 (1952)).

The compounds of the formula (XXIV) are obtained, for example, by reacting substituted phenylacetic acids of the formula (XXVII)

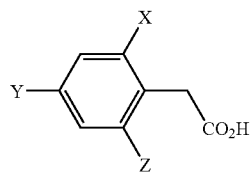

(XXVII)

in which
X, Y and Z are each as defined above
with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons such as toluene or methylene chloride), at temperatures from −20° C. to 150° C., preferably from −10° C. to 100° C.

Some of the compounds of the formulae (XXIII) and (XXVI) are known, and/or they can be prepared by known processes (see, for example, Compagnon, Miocque Ann. Chim. (Paris) [14] 5, p. 11–22, 23–27 (1970)).

The substituted cyclic aminocarboxylic acids of the formula (XXVIa) in which A and B form a ring are generally obtainable by the Bucherer-Bergs synthesis or by the Strecker synthesis and are in each case obtained in different isomer forms. Thus, under the conditions of the Bucherer-Bergs synthesis, the isomers (for simplicity called β below), in which the radicals R and the carboxyl group are equatorial are predominantly obtained, while under the conditions of the Strecker synthesis the isomers (for simplicity called α below) in which the amino group and the radicals R are equatorial are predominantly obtained.

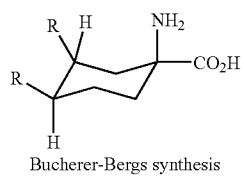

Bucherer-Bergs synthesis
(β isomer)

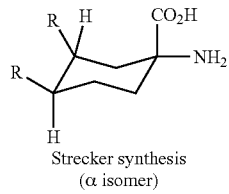

Strecker synthesis
(α isomer)

(L. Munday, J. Chem. Soc. 4372 (1961); J. T. Eward, C. Jitrangeri, Can. J. Chem. 53, 3339 (1975).

Furthermore, the starting materials of the formula (II)

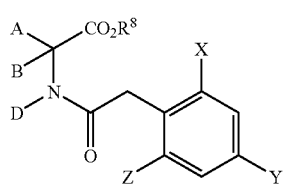

(II)

in which
A, B, D, X, Y, Z and $R^8$ are each as defined above
used in the above process (A) can be prepared when aminonitriles of the formula (XXVIII)

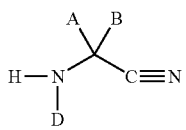

(XXVIII)

in which
A, B and D are each as defined above are reacted with substituted phenylacetyl halides of the formula (XXIV)

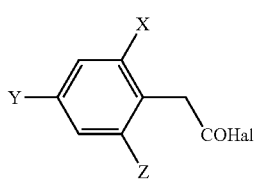

(XXIV)

in which
X, Y, Z and Hal are each as defined above
to give compounds of the formula (XXIX)

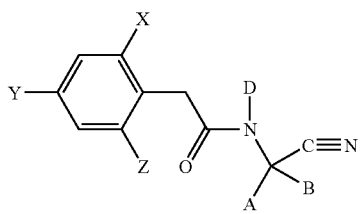

(XXIX)

in which
A, B, D, X, Y and Z are each as defined above
and these are subsequently subjected to acidic alcoholysis.

The compounds of the formula (XXIX) are likewise novel
The compounds of the formula (III)

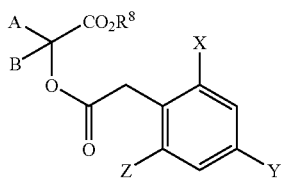

(III)

in which
A, B, X, Y, Z and $R^8$ are each as defined above
required as starting materials in the process (B) according to the invention are novel.

They can be prepared by methods known in principle.

Thus, the compounds of the formula (III), for example, are obtained when 2-hydroxycarboxylic esters of the formula (XXX)

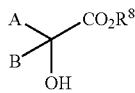 (XXX)

in which
A, B and R$^8$ are each as defined above
are acylated with substituted phenylacetyl halides of the formula (XXIV)

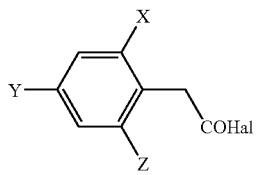 (XXIV)

in which
X, Y, Z and Hal are each as defined above
(Chem. Reviews 52, 237–416 (1953)).

Furthermore, compounds of the formula (III) are obtained when substituted phenylacetic acids of the formula (XXVII)

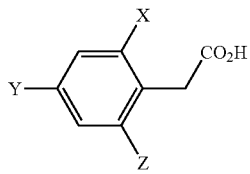 (XXVII)

in which
X, Y and Z are each as defined above
are alkylated with α-halogenocarboxylic esters of the formula (XXXI)

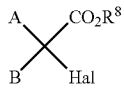 (XXXI)

in which
A, B and R$^8$ are each as defined above and
Hal represents chlorine or bromine.

The compounds of the formula (XXVII) are novel.
The compounds of the formula (XXXI) are known and in most cases commercially available.
The compounds of the formula (XXVII)

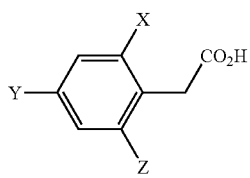 (XXVII)

in which
X, Y and Z are each as defined above
are obtained, for example,
α) when compounds of the formula (XXVII-a)

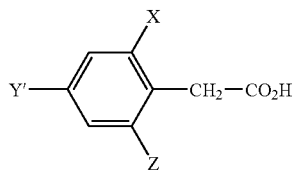 (XXVII-a)

in which
X and Z are each as defined above
Y' represents chlorine or bromine, preferably represents bromine,
are reacted with boronic acids of the formula (XII)

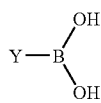 (XII)

in which
Y is as defined above
in the presence of a solvent, a base and a catalyst (preferably a palladium complex, such as, for example, tetrakis(triphenylphosphine)-palladium or
β) when phenylacetic esters of the formula (XXXII)

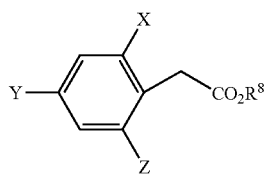 (XXXII)

in which
X, Y, Z and R$^8$ are each as defined above
are hydrolysed under generally known standard conditions in the presence of acids or bases, in the presence of a solvent, or
γ) when phenylacetic acids of the formula (XXVII-b)

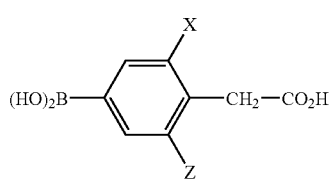 (XXVII-b)

in which
X and Z are each as defined above
are reacted with halogen compounds of the formula (XXXIII), Y-Hal (XXXIII)

in which

Y is as defined above and

Hal represents chlorine, bromine or iodine in the presence of a solvent, a base and a catalyst (preferably one of the abovementioned palladium complexes).

The compounds of the formulae (XII) and (XXXIII) are known, some of them are commercially available, or they can be prepared by processes known in principle. Some of the phenylacetic acids of the formula (XXVII-a) are known from WO 96/35 664 and WO 97/02243, or they can be prepared by the processes described therein.

The compounds of the formula (XXVII-b) and (XXII) are novel.

The compounds of the formula (XXVII-b)

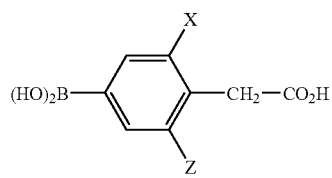

(XXVII-b)

in which

X and Z are each as defined above are obtained, for example, when phenylacetic acids of the formula (XXVII-a)

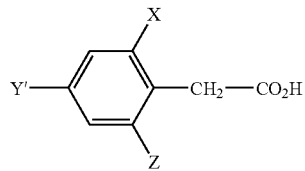

(XXVII-a)

in which

X, Y' and Z are each as defined above are reacted with lithium compounds of the formula (XXXIV)

Li—$R^{21}$      (XXXIV)

in which $R^{21}$ represents $C_1$–$C_8$-alkyl or phenyl, preferably represents n-$C_4H_9$, and boronic esters of the formula (XXXV)

B(O$R^8$)$_3$      (XXXV)

in which $R^8$ is as defined above in the presence of a diluent.

The compounds of the formulae (XXXIV) and (XXXV) are commercially available compounds.

The compounds of the formula (XXXII)

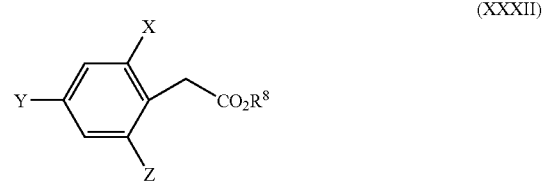

(XXXII)

in which

X, Y, Z and $R^8$ are each as defined above are obtained, for example, when phenylacetic esters of the formula (XXII-a)

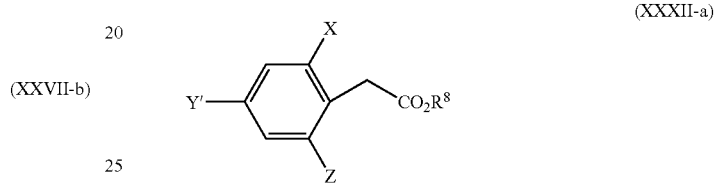

(XXXII-a)

in which $R^8$, X, Y' and Z are each as defined above are reacted with boronic acids of the formula (XII)

(XII)

in which

Y is as defined above in the presence of a solvent, a base and a catalyst (preferably one of the abovementioned palladium complexes).

Some of the phenylacetic esters of the formula (XXXII-a) are known from the applications WO 96/35 664 and WO 97/02 243, or they can be prepared by the processes described therein.

The compounds of the formula (IV)

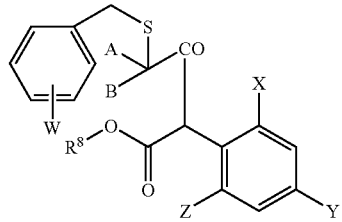

(IV)

in which

A, B, W, X, Y, Z and $R^8$ are each as defined above required as starting materials in the above process (C) are novel.

They can be prepared by methods known in principle.

The compounds of the formula (IV) are obtained, for example, when substituted phenylacetic esters of the formula (XXXII)

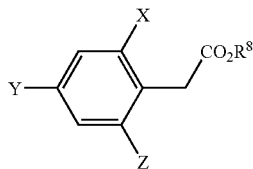

(XXXII)

in which

X, Y, R$^8$ and Z are each as defined above are acylated with 2-benzylthio-carbonyl halides of the formula (XXXVI)

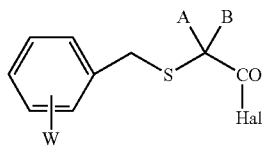

(XXXVI)

in which

A, B and W are each as defined above and

Hal represents halogen (in particular chlorine or bromine)

in the presence of strong bases (see, for example, M. S. Chambers, E. J. Thomas, D. J. Williams, J. Chem. Soc. Chem. Commun., (1987), 1228).

The compounds of the formula (XXXII) are novel. Compounds of the formula (XXXII) are obtained, for example, when compounds of the formula (XXVII)

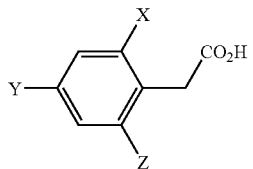

(XXVII)

in which

X, Y and Z are each as defined above are esterified in the presence of alcohols and dehydrating agents (for example conc. sulphuric acid), or when alcohols are acylated with compounds of the formula (XXIV)

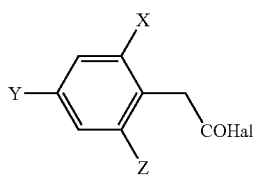

(XXVI)

in which

X, Y, Z and Hal are each as defined above (Chem. Reviews 52, 237–416 (1953)).

Some of the benzylthio-carbonyl halides of the formula (XXXVI) are known, and/or they can be prepared by known processes (J. Antibiotics (1983), 26, 1589).

The halogenocarbonyl ketenes of the formula (V) required as starting materials in the above processes (D), (E) and (F) are novel. They can be prepared by methods which are generally known in principle (cf., for example, Org. Prep. Proced. Int., 7, (4), 155–158, 1975 and DE 1 945 703). Thus, for example, the compounds of the formula (V)

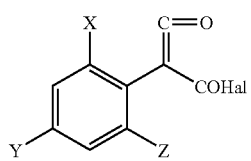

(V)

in which

X, Y and Z are each as defined above and

Hal represents chlorine or bromine are obtained when substituted phenylmalonic acids of the formula (XXXVII)

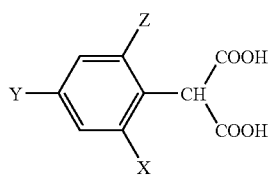

(XXXVII)

in which

X, Y and Z are each as defined above are reacted with acyl halides, such as, for example, thionyl chloride, phosphorus(V) chloride, phosphorus(III) chloride, oxalyl chloride, phosgene or thionyl bromide, if appropriate in the presence of catalysts, such as, for example, dimethylformamide, methyl-steryl-formamide or triphenylphosphine and if appropriate in the presence of bases such as, for example, pyridine or triethylamine.

The substituted phenylmalonic acids of the formula (XXXVII) are novel. They can be prepared by generally known processes (cf., for example, Organikum, VEB Deutscher Verlag der Wissenschaften, Berlin 1977, p. 517 ff, EP-A-528 156, WO 96/35 664, WO 97/02 243).

Thus, phenylmalonic acids of the formula (XXXVII)

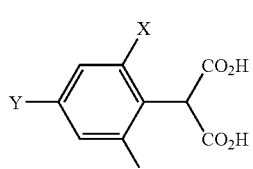

(XXXVII)

in which

X, Y and Z are each as defined above are obtained when phenylmalonic esters of the formula (VI)

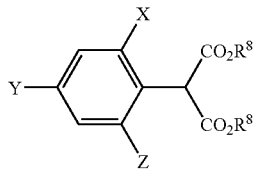
(VI)

in which

X, Y, Z and $R^8$ are each as defined above are initially hydrolysed in the presence of a base and in a solvent and subsequently carefully acidified (EP-528 156, WO 96/35 664, WO 97/02 243).

The malonic esters of the formula (VI)

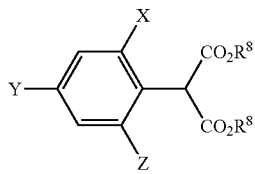
(VI)

in which

X, Y, Z and $R^8$ are each as defined above are novel.

They can be prepared by generally known methods of organic chemistry (cf., for example, Tetrahedron Lett. 27, 2763 (1986) and Organikum, VEB Deutscher Verlag der Wissenschaften, Berlin 1977, p. 587 ff.).

Some of the hydrazines of the formula (VII)

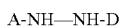   (VII), in which

A and D are each as defined above required as starting materials for the process (D) according to the invention are known, and/or they can be prepared by methods known from the literature (cf., for example, Liebigs Ann. Chem. 585, 6 (1954); Reaktionen der organischen Synthese, C. Ferri, p. 212, 513; Georg Thieme Verlag Stuttgart, 1978; Liebigs Ann. Chem. 443, 242 (1925); Chem. Ber. 98, 2551 (1965), EP-508 126).

The carbonyl compounds of the formula (VIII)

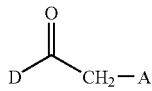
(VIII)

in which

A and D are each as defined above or their silyl enol ethers of the formula (VIIIa)

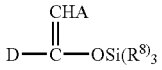
(VIIIa)

in which

A, D and $R^8$ are each as defined above required as starting materials for the process (E) according to the invention are commercially available, generally known compounds or compounds which are obtainable by known processes.

The preparation of the ketene acid chlorides of the formula (V), required as starting materials for carrying out the process (F) according to the invention has already been described above. The thioamides of the formula (IX)

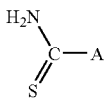
(IX)

in which

A is as defined above required for carrying out the process (F) according to the invention are compounds which are generally known in organic chemistry.

The compounds of the formula (X)

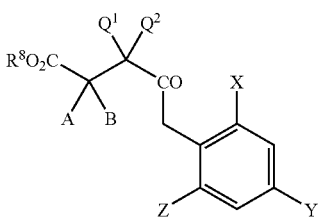
(X)

in which

A, B, $Q^1$, $Q^2$, X, Y, Z and $R^8$ are each as defined above required as starting materials in the above process (G) are novel.

They can be prepared by methods known in principle.

The 5-aryl-4-ketocarboxylic esters of the formula (X) are obtained, for example, when 5-aryl-4-ketocarboxylic acids of the formula (XXXVIII)

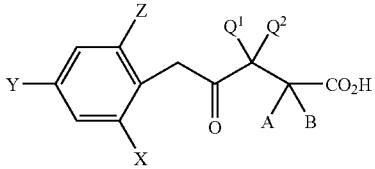
(XXXVIII)

in which

X, Y, Z, A, B, $Q^1$ and $Q^2$ are each as defined above are esterified (cf., for example, Organikum, 15th edition, Berlin, 1977, page 499) or alkylated (see Preparation Example).

The 5-aryl-4-ketocarboxylic acids of the formula (XXXVIII)

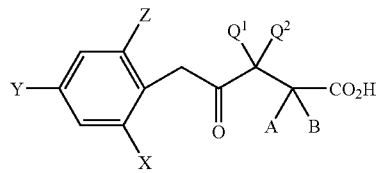

(XXXVIII)

in which

A, B, $Q^1$, $Q^2$, X, Y and Z are each as defined above are novel but can be prepared by methods known in principle (see Preparation Example).

The 5-aryl-4-ketocarboxylic acids of the formula (XXXVIII) are obtained, for example, when 2-phenyl-3-oxo-adipic esters of the formula (XXXIX)

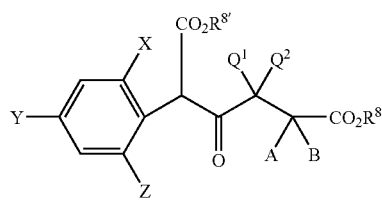

(XXXIX)

in which

A, B, $D^1$, $D^2$, X, Y and Z are each as defined above and $R^8$ and $R^{8'}$ each represent alkyl (in particular $C_1$–$C_8$-alkyl)

are decarboxylated, if appropriate in the presence of a diluent and if appropriate in the presence of a base or acid (cf., for example, Organikum, 15th edition, Berlin, 1977, pages 519 to 521).

The compounds of the formula (XXXIX)

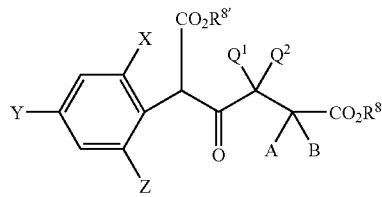

(XXXIX)

in which

A, B, $Q^1$, $Q^2$, X, Y, Z, $R^8$, $R^{8'}$ are each as defined above are novel.

The compounds of the formula (XXXIX) are obtained, for example, when dicarboxylic monoester chlorides of the formula (XL),

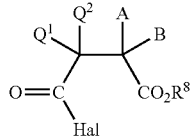

(XL)

in which

A, B, $Q^1$, $Q^2$ and $R^8$ are each as defined above and

Hal represents chlorine or bromine or carboxylic anhydrides of the formula (XLI)

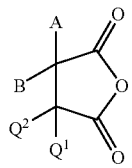

(XLI)

in which

A, B, $Q^1$ and $Q^2$ are each as defined above are acylated with a phenyl acetic ester of the formula (XXII)

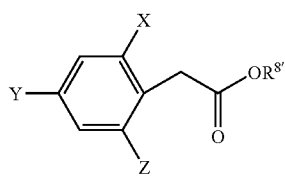

(XXXII)

in which

X, Y, Z and $R^{8'}$ are each as defined above in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XL) and (XLI) are known compounds of organic chemistry, and/or they can be prepared in a simple manner by methods known in principle.

The compounds of the formula (XI)

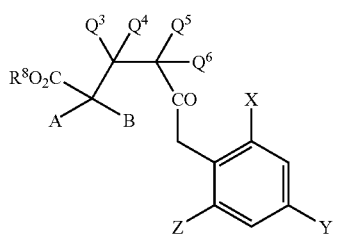

(XI)

in which

A, B, $Q^3$, $Q^4$, $Q^5$, $Q^6$, X, Y, Z and $R^8$ are each as defined above required as starting materials in the above process (H) are novel.

They can be prepared by methods known in principle.

The 6-aryl-5-ketocarboxylic esters of the formula (XI) are obtained, for example, when 6-aryl-5-ketocarboxylic acids of the formula (XLII)

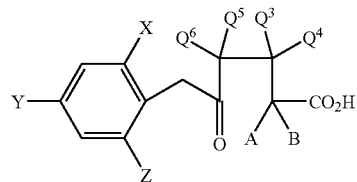
(XLII)

in which

A, B, $Q^3$, $Q^4$, $Q^5$, $Q^6$, X, Y and Z are each as defined above are esterified (cf., for example, Organikum, 15th edition, Berlin, 1977, page 499 and Preparation Example).

The 6-aryl-5-ketocarboxylic acids of the formula (XLII)

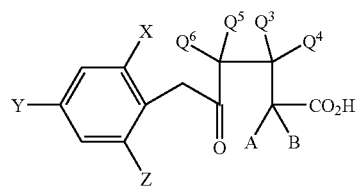
(XLII)

in which

A, B, $Q^3$, $Q^4$, $Q^5$, $Q^6$, X, Y and Z are each as defined above are novel. They can be prepared by methods known in principle, for example by hydrolysing and decarboxylating substituted 2-phenyl-3-oxo-heptanedioic esters of the formula (XLIII)

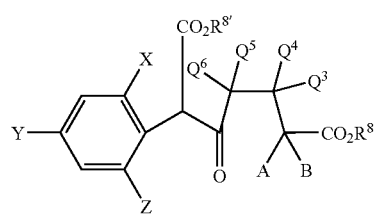
(XLIII)

in which

A, B, $Q^3$, $Q^4$, $Q^5$, $Q^6$, X, Y and Z are each as defined above and $R^8$ and $R^{8'}$ are each alkyl (preferably $C_1$–$C_6$-alkyl), if appropriate in the presence of a diluent and if appropriate in the presence of a base or acid (cf., for example, Organikun, 15th edition, Berlin, 1977, page 519 to 521 and Preparation Example).

The compounds of the formula (XLIII)

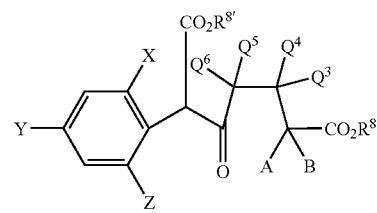
(XLIII)

in which

A, B, $Q^3$, $Q^4$, $Q^5$, $Q^6$, X, Y, Z, $R^8$ and $R^{8'}$ are each as defined above are novel. They can be obtained when dicarboxylic anhydrides of the formula (XLIV),

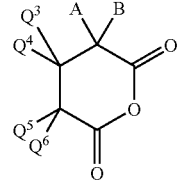
(XLIV)

in which

A, B, $Q^3$, $Q^4$, $Q^5$ and $Q^6$ are each as defined above are condensed with a substituted phenylacetic ester of the formula (XXXII)

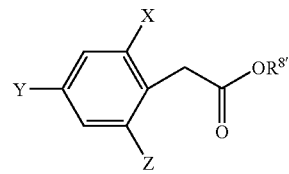
(XXXII)

in which

X, Y, Z and $R^{8'}$ are each as defined above in the presence of a diluent and in the presence of a base.

Some of the compounds of the formula (XLIV) are known, and/or they can be prepared by known processes.

The compounds of the formula (XXXII) have already been described under the precursors for the process (B). Furthermore, compounds of the formula (XXXII) are obtained by reacting substituted 1,1,1-trichloro-2-phenylethanes of the formula (XLV)

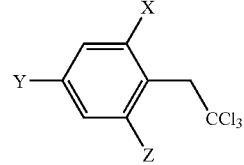
(XLV)

in which

X, Y and Z are each as defined above initially with alkoxides (for example alkali metal alkoxides such as sodium methoxide or sodium ethoxide) in the presence of a diluent (for example the alcohol derived from the alkoxide) at temperatures between 0° C. and 150° C., preferably between 20° C. and 120° C., and subsequently with an acid (preferably an inorganic acid such as, for example, sulphuric acid) at temperatures between −20° C. and 150° C., preferably between 0° C. and 100° C. (cf. DE 3 314 249).

The compounds of the formula (XLV) are novel, they can be prepared by processes known in principle.

The compounds of the formula (XLV) are obtained, for example, when anilines of the formula (XLVI)

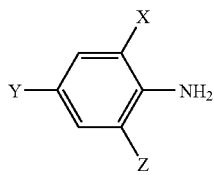

(XLVI)

in which

X, Y and Z are each as defined above are reacted with vinylidene chloride ($CH_2=CCl_2$) in the presence of an alkyl nitrite of the formula (XLVII)

$R^{21}$—ONO  (XLVII)

in which $R^{21}$ represents alkyl, preferably $C_1$–$C_6$-alkyl, in the presence of copper(II) chloride and, if appropriate, in the presence of a diluent (for example an aliphatic nitrile such as acetonitrile), at a temperature of from −20° C. to 80° C., preferably from 0° C. to 60° C.

The compounds of the formula (XLVII) are known compounds of organic chemistry. Copper(II) chloride and vinylidene chloride have been known for a long time and are commercially available.

The compounds of the formula (XLVI) are novel.

Compounds of the formula (XLVI)

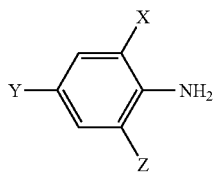

(XLVI)

in which

X, Y and Z are each as defined above, for example, are obtained when anilines of the formula (XLVI-a)

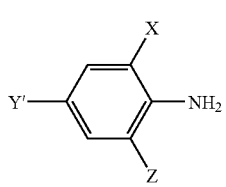

(XLVI-a)

in which

X and Z are each as defined above

Y' represents halogen (preferably represents bromine)

are reacted with boronic acids of the formula (XII)

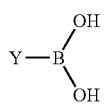

(XII)

in which

Y is as defined above in the presence of a solvent, a base and a catalyst (preferably a palladium complex, such as, for example, tetrakis(triphenylphosphine)palladium.

Some of the compounds of the formulae (I-1'-a) to (I-8'-a) in which A, B, D, $Q^1$, $Q^2$, $Q^3$, $Q^4$, $Q^5$, $Q^6$, X and Z are each as defined above and Y' represents chlorine and bromine, preferably represents bromine, and which are required as starting materials in the above process (I) are known (WO 96/35 664, WO 97/02 243) or they can be prepared by the processes described therein or by processes (A) to (H).

Some of the boronic acids of the formula (XII)

(XII)

in which

Y is as defined above are commercially available, or they can be prepared in a simple manner by generally known processes.

The acyl halides of the formula (XIII), carboxylic anhydrides of the formula (XIV), chloroformic esters or chloroformic thioesters of the formula (XV), chloromonothioformic esters or chlorodithioformic esters of the formula (XVI), sulphonyl chlorides of the formula (XVII), phosphorus compounds of the formula (XVIII) and metal hydroxides, metal alkoxides or amines of the formulae (XIX) and (XX) and isocyanates of the formula (XXI) and carbamoyl chlorides of the formula (XXII) furthermore required as starting materials for carrying out the processes (J), (K), (L), (M), (N), (O) and (P) according to the invention are generally known compounds of organic or inorganic chemistry.

Moreover, the compounds of the formulae (VII), (VIII), (IX), (XIII) to (XXIII), (XXVI), (XXVIII), (XXX), (XXXVI), (XL), (XLI) and (XLVI-a) are known from the patent applications cited at the outset, and/or they can be prepared by the methods given therein.

The process (A) is characterized in that compounds of the formula (II) in which A, B, D, X, Y, Z and $R^8$ are each as defined above are subjected to an intramolecular condensation in the presence of a base.

Suitable diluents for the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, iso-propanol, butanol, iso-butanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperatures can be varied within a relatively wide range. In general, the reaction is carried out at temperatures between 0° C. and 250° C., preferably between 50° C. and 150° C.

The process (A) according to the invention is generally carried out under atmospheric pressure.

When carrying out process (A) according to the invention, the reaction components of the formula (II) and the deprotonating bases are generally employed in approximately double-equimolar amounts. However, it is also possible to use a larger excess (up to 3 mol) of one component or the other.

The process (B) is characterized in that compounds of the formula (III) in which A, B, X, Y, Z and $R^8$ are each as defined above are subjected to an intramolecular condensation in the presence of a diluent and in the presence of a base.

Suitable diluents for the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, iso-propanol, butanol, iso-butanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (B) according to the invention, the reaction temperatures can be varied within a relatively wide range. In general, the reaction is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process (C) is characterized in that compounds of the formula (IV) in which A, B, W, X, Y, Z and $R^8$ are each as defined above are cyclized intramolecularly in the presence of an acid and, if appropriate, in the presence of a diluent.

Suitable diluents for the process (C) according to the invention are all inert organic solvents. Preference is given to using hydrocarbons, such as toluene and xylene, furthermore halogenated hydrocarbons such as dichloromethane, chloroform, ethylene chloride, chlorobenzene, dichlorobenzene, moreover polar solvents, such as dimethyl sulphoxide, sulpholane, dimethyl formamide and N-methyl-pyrrolidone. Furthermore, it is possible to employ alcohols such as methanol, ethanol, propanol, iso-propanol, butanol, isobutanol, tert-butanol.

If appropriate, the acid used can also serve as diluent.

Suitable acids for the process (C) according to the invention are all customary inorganic and organic acids, such as, for example, hydrohalic acids, sulphuric acid, alkyl, aryl and haloalkylsulphonic acids, in particular halogenated alkylcarboxylic acids, such as, for example, trifluoroacetic acid.

When carrying out the process (C) according to the invention, the reaction temperatures can be varied within a relatively wide range. In general, the reaction is carried out at temperatures between 0° C. and 250° C., preferably between 50° C. and 150° C.

The process (C) according to the invention is generally carried out under atmospheric pressure.

When carrying out the process (C) according to the invention, the reaction components of the formula (IV) and the acid are employed, for example, in equimolar amounts. However, it is also possible, if appropriate, to use the acid as solvent or as catalyst.

The processes (D-α) and (D-β) are characterized in that compounds of the formula (V) or (VI) in which X, Y, Z, $R^8$ and Hal are each as defined above are reacted with compounds of the formula (VII) in which A and D are each as defined above, if appropriate in the presence of a base and if appropriate in the presence of a diluent.

Suitable diluents for the processes (D-α) and (D-β) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also, only in the case where compounds of the formula (VI) are employed, alcohols such as methanol, ethanol, propanol, iso-propanol, butanol, iso-butanol and tert-butanol.

When compounds of the formula (V) are employed, suitable bases are inorganic bases, in particular alkali metal or alkaline earth metal carbonates such as sodium carbonate, potassium carbonate or calcium carbonate, and also organic bases, such as, for example, pyridine or triethylamine, and when compounds of the formula (VI) are employed, alkali metal and alkaline earth metal oxides, hydroxides and carbonates, such as sodium hydroxide, potassium hydroxide, magnesium hydroxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl ($C_8$–$C_{10}$)-ammonium chloride) or TDA 1 (=tris-(methoxyethoxyethyl)-amine), furthermore alkali metals, such as sodium or potassium, alkali metal amides and hydrides and alkaline earth metal amides and hydrides, such as sodium amide, sodium hydride and calcium hydride, and additionally alkali metal alkoxides, such as sodium methoxide and potassium tert-butoxide.

When carrying out the processes (D-α) and (D-β) according to the invention, the reaction temperatures can be varied within a relatively wide range. In general, the reaction is carried out at temperatures between −20° C. and 250° C., preferably between 0° C. and 150° C.

The processes (D-α) and (D-β) according to the invention are generally carried out under atmospheric pressure.

When carrying out the processes (D-α) and (D-β) according to the invention, the reaction components of the formulae (V) and (VII) or (VI) and (VII) and the deprotonating bases which are employed if appropriate are generally employed in approximately equimolar amounts. However, it is also possible to use a relatively large excess (up to 3 mol) of one component or the other.

The process (E) according to the invention is characterized in that carbonyl compounds of the formula (VIII) or enol ethers thereof of the formula (VIII-a) are reacted with ketene acid halides of the formula (V) in the presence of a diluent and, if appropriate, in the presence of an acid acceptor.

Suitable diluents for the process (E) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide or N-methyl-pyrrolidone.

Suitable acid acceptors for carrying out the process variant E) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethyl-aniline.

When carrying out the process variant E) according to the invention, the reaction temperatures can be varied within a relatively wide range. Advantageously, the reaction is carried out at temperatures between 0° C. and 250° C., preferably between 50° C. and 220° C.

The process (E) according to the invention is advantageously carried out under atmospheric pressure.

When carrying out the process (E) according to the invention, the reaction components of the formulae (VIII) and (V) in which A, D, X, Y and Z are each as defined above and Hal represents halogen, and, if appropriate, the acid acceptors, are generally employed in approximately equimolar amounts. However, it is also possible to use a relatively large excess (up to 5 mol) of one component or the other.

The process (F) according to the invention is characterized in that thioamides of the formula (IX) are reacted with ketene acid halides of the formula (V) in the presence of a diluent and, if appropriate, in the presence of an acid acceptor.

Suitable diluents for the process variant F) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methyl-pyrrolidone.

Suitable acid acceptors for carrying out the process (F) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethyl-aniline.

When carrying out the process (F) according to the invention, the reaction temperatures can be varied within a relatively wide range. Advantageously, the reaction is carried out at temperatures between 0° C. and 250° C., preferably between 20° C. and 220° C.

The process (F) according to the invention is advantageously carried out under atmospheric pressure.

When carrying out the process (F) according to the invention, the reaction components of the formulae (IX) and (V) in which A, X, Y and Z are each as defined above and Hal represents halogen, and, if appropriate, the acid acceptors, are generally employed in approximately equimolar amounts. However, it is also possible to use a relatively large excess (up to 5 mol) of one component or the other.

The process (G) is characterized in that compounds of the formula (X) in which A, B, $Q^1$, $Q^2$, Y, Z and $R^8$ are each as defined above are subjected to an intramolecular condensation in the presence of a base.

Suitable diluents for the process (G) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. It is furthermore possible to use alcohols, such as methanol, ethanol, propanol, isopropanol, butanol, isobutanol, tert-butanol.

Suitable bases (deprotonating agents) for carrying out the process (G) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl ($C_8$–$C_{10}$)ammonium chloride) or TDA 1 (tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying the process (G) according to the invention, the reaction temperatures can be varied within a relatively wide range. In general, the reaction is carried out at temperatures between −75° C. and 250° C., preferably between −50° C. and 150° C.

The process (G) according to the invention is generally carried out under atmospheric pressure.

When carrying out the process (G) according to the invention, the reaction components of the formula (X) and the deprotonating bases are generally employed in approximately equimolar amounts. However, it is also possible to use a relatively large excess (up to 3 mol) of one component or the other.

The process (H) is characterized in that compounds of the formula (XI) in which A, B, $Q^3$, $Q^4$, $Q^5$, $Q^6$, X, Y, Z and $R^8$ are each as defined above are subjected to an intramolecular condensation in the presence of bases.

Suitable diluents for the process (H) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. Alcohols, such as methanol, ethanol, propanol, iso-propanol, butanol, isobutanol and tert-butanol can also be used.

Suitable bases (deprotonating agents) for carrying out the process (H) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl ($C_8$–$C_{10}$)ammonium chloride) or TDA 1 (tris-(methoxyethoxyethyl)amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying the process (H) according to the invention, the reaction temperatures can be varied within a relatively wide range. In general, the reaction is carried out at temperatures between 0° C. and 250° C., preferably between 50° C. and 150° C.

The process (H) according to the invention is generally carried out under atmospheric pressure.

When carrying out the process (H) according to the invention, the reaction components of the formula (XII) and the deprotonating bases are generally employed in approximately equimolar amounts. However, it is also possible to use a relatively large excess (up to 3 mol) of one component or the other.

For carrying out the process (I) according to the invention, palladium(0) complexes are suitable as catalysts. Use is made, for example, of tetrakis(triphenylphosphine)palladium. Also suitable are palladium(II) compounds such as bis(triphenylphosphine)palladium(II) chloride.

Suitable acid acceptors for carrying out the process (I) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, potassium fluoride, caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (I) according to the invention are water, organic solvents and any mixtures thereof. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature in the process (I) according to the invention can be varied within a relatively wide range. In general, the reaction is carried out at temperatures between 0° C. and +140° C., preferably between 50° C. and +100° C.

When carrying out the process (I) according to the invention, boronic acid of the formula (XII) and compounds of the formulae (I-1-a) to (I-8-a) are employed in a molar ratio of from 1:1 to 3:1, preferably from 1:1 to 2:1. In general, 0.005 to 0.5 mol, preferably 0.01 mol to 0.1 mol of catalyst is employed per mole of the compounds of the formulae (I-1-a) to (I-8-a). The base is usually employed in excess.

The process (J-α) is characterized in that compounds of the formulae (I-1-a) to (I-8-a) are in each case reacted with carbonyl halides of the formula (XIII), if appropriate in the presence of a diluent and if appropriate in the prescence of an acid binder.

Suitable diluents for the process (J-α) according to the invention are all solvents which are inert towards the acyl halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acyl halide permitting, the reaction can also be carried out in the presence of water.

Suitable acid binders for the reaction according to the process (J-α) according to the invention are all customary acid acceptors. Preference is given to using tertiary amines, such as triethylamine, pyridine, diazabicyclooctane (DABCO), diazabicyclo-undecene (DBU), diazabicyclononene (DBN), Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides such as sodium hydroxide and potassium hydroxide.

The reaction temperatures in the process (J-α) according to the invention can be varied within a relatively wide range.

In general, the reaction is carried out at temperatures between −20° C. and +150° C., preferably between 0° C. and 100° C.

When carrying out the process (J-α) according to the invention, the starting materials of the formulae (I-1-a) to (I-8-a) and the carbonyl halide of the formula (XIII) are generally in each case employed in approximately equivalent amounts. However, it is also possible to employ a relatively large excess (up to 5 mol) of the carbonyl halide. Work-up is carried out by customary methods.

The process (J-β) is characterized in that compounds of the formulae (I-1-a) to (I-8-a) are reacted with carboxylic anhydrides of the formula (XIV), if appropriate in the presence of a diluent and if appropriate in the presence of an acid binder.

Preferred diluents for the process (J-β) according to the invention are those diluents which are also preferred when acyl halides are used. Otherwise, it is also possible for a carboxylic anhydride employed in excess to act simultaneously as a diluent.

In the process (J-β), acid binders which are added, if appropriate, are preferably those acid binders which are also preferred when acyl halides are used.

In the process (J-β) according to the invention, the reaction temperatures can be varied within a relatively wide range. In general, the reaction is carried out at temperatures between −20° C. and +150° C., preferably between 0° C. and 100° C.

When carrying out the process (J-β) according to the invention, the starting materials of the formulae (I-1-a) to (I-8-a) and the carboxylic anhydride of the formula (XIV) are generally each employed in approximately equivalent amounts. However, it is also possible to use a relatively large excess (up to 5 mol) of the carboxylic anhydride. Work-up is carried out by customary methods.

In general, the adopted procedure is to remove diluent and excess carboxylic anhydride and also the carboxylic acid formed by distillation or by washing with an organic solvent or with water.

The process (K) is characterized in that compounds of the formulae (I-1-a) to (I-8-a) are in each case reacted with chloroformic esters or chloroformic thiol esters of the formula (XV), if appropriate in the presence of a diluent and if appropriate in the presence of an acid binder.

Suitable diluents for the reaction according to the process (K) according to the invention are all customary acid acceptors. Preference is given to using tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides such as sodium hydroxide and potassium hydroxide.

Suitable diluents for the process (K) according to the invention are all solvents which are inert towards the chloroformic esters or chloroformic thiol esters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (K) according to the invention the reaction temperatures can be varied within a relatively wide range. If the reaction is carried out in the presence of a diluent and an acid binder, the reaction temperatures are generally between −20° C. and +100° C., preferably between 0° C. and 50° C.

The process (K) according to the invention is generally carried out under atmospheric pressure.

When carrying out the process (K) according to the invention, the starting materials of the formulae (I-1-a) to (I-8-a) and the appropriate chloroformic ester or chloroformic thiol ester of the formula (XV) are generally in each case employed in approximately equivalent amounts. However, it is also possible to employ a relatively large excess (up to 2 mol) of one component or the other. Work-up is carried out by customary methods. In general, precipitated salts are removed and the reaction mixture that remains is concentrated by stripping the diluent.

The process (L) according to the invention is characterized in that compounds of the formulae (I-1-a) to (I-8-a) are in each case reacted with compounds of the formula (XVI) in the presence of a diluent and, if appropriate, in the presence of an acid binder.

In the preparation process (L), approximately 1 mol of chloromonothioformic ester or chlorodithioformic ester of the formula (XVI) is reacted per mole of starting material of the formulae (I-1-a) to (I-8-a), at from 0 to 120° C., preferably from 20 to 60° C.

Suitable diluents which are added if appropriate are all inert polar organic solvents, such as ethers, amides, sulphones, sulphoxides, but also halogenoalkanes.

Preference is given to using dimethyl sulphoxide, tetrahydrofuran, dimethylformamide or methylene chloride.

If, in a preferred embodiment, the enolate salt of the compounds (I-1-a) to (I-8-a) is prepared by addition of strong deprotonating agents, such as, for example, sodium hydride or potassium tert-butoxide, it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (M) according to the invention is characterized in that compounds of the formulae (I-1-a) to (I-8-a) are in each case reacted with sulphonyl chlorides of the formula (XVII), if appropriate in the presence of a diluent and if appropriate in the presence of an acid binder.

In the preparation process (M), approximately 1 mol of sulphonyl chloride of the formula (XVII) is reacted per mole of starting material of the formula (I-1-a) to (I-8-a), at from −20 to 150° C., preferably at from 20 to 70° C. um.

Suitable diluents which are added if appropriate are all inert polar organic solvents, such as ethers, amides, nitrites, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-1-a) to (I-8-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (N) according to the invention is characterized in that compounds of the formulae (I-1-a) to (I-8-a) are in each case reacted with phosphorus compounds of the formula (XVIII), if appropriate in the presence of a diluent and if appropriate in the presence of an acid binder.

In the preparation process (N), 1 to 2, preferably 1 to 1.3, mol of the phosphorus compound of the formula (XVIII) are reacted per mole of the compounds (I-1-a) to (I-8-a) at temperatures between 40° C. and 150° C., preferably between −10 and 110° C., to give compounds of the formulae (I-1-e) to (I-8-e).

Suitable solvents which are added if appropriate are all inert polar organic solvents, such as ethers, amides, nitrites, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added if appropriate are customary inorganic or organic bases such as hydroxides, carbonates or amines. Examples include sodium hydroxide, sodium carbonate, potassium carbonate, pyridine, triethylamine.

The reaction can be carried out at atmospheric pressure or under elevated pressure and is preferably carried out under atmospheric pressure. Work-up is carried out by customary methods of organic chemistry. The resulting end products are preferably purified by crystallization, chromatographic purification or by so-called "incipient distillation", i.e. removal of the volatile components under reduced pressure.

The process (O) is characterized in that compounds of the formulae (I-1-a) to (I-8-a) are reacted with metal hydroxides or metal alkoxides of the formula (XIX) or amines of the formula (XX), if appropriate in the presence of a diluent.

Preferred diluents for the process (O) according to the invention are ethers, such as tetrahydrofuran, dioxane, diethyl ether, or else alcohols, such as methanol, ethanol, isopropanol, but also water.

The process (O) according to the invention is generally carried out under atmospheric pressure.

The reaction temperatures are generally between −20° C. and 100° C., preferably between 0° C. and 50° C.

The process (P) according to the invention is characterized in that compounds of the formulae (I-1-a) to (I-8-a) are in each case reacted with (P-α) compounds of the formula (XXI), if appropriate in the presence of a diluent and if appropriate in the presence of a catalyst, or (P-β) with compounds of the formula (XXII), if appropriate in the presence of a diluent and if appropriate in the presence of an acid binder.

In the preparation process (P-α), approximately one mol of isocyanate of the formula (XXI) is reacted per mole of starting material of the formulae (I-1-a) to (I-8-a), at from 0 to 100° C., preferably at from 20 to 50° C.

Suitable diluents which are added if appropriate are all inert organic solvents, such as ethers, amides, nitriles, sulphones, sulphoxides.

If appropriate, catalysts may be added to accelerate the reaction. Very advantageously, the catalysts which are employed are organotin compounds, such as, for example, dibutyltin dilaurate. The reaction is preferably carried out at atmospheric pressure.

In the preparation process (P-β), approximately 1 mol of carbamoyl chloride of the formula (XXII) is reacted per mole of starting material of the formulae (I-1-a) to (I-8-a), at from −20 to 150° C., preferably from 0 to 70° C. um.

Suitable diluents which are added if appropriate are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-1-a) to (I-8-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus*, *Gryllotalpa* spp., *Locusta migratoria migratorioides*, *Melanoplus* spp. and *Schistocerca gregaria*.

From the order of the Blattaria, for example, *Blatta orientalis*, *Periplaneta americana*, *Leucophaea maderae*, *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis*, *Haematopinus* spp., *Linognathus* spp., *Trichodectes* spp. and *Damalinia* spp.

From the order of the Thysanoptera, for example, *Hercinothrips femoralis*, *Thrips tabaci*, *Thrips palmi* and *Frankliniella accidentalis*.

From the order of the Heteroptera, for example, *Eurygaster* spp., *Dysdercus intermedius*, *Piesma quadrata*, *Cimex lectularius*, *Rhodnius prolixus* and *Triatoma* spp.

From the order of the Homoptera, for example, *Aleurodes brassicae*, *Bemisia tabaci*, *Trialeurodes vaporariorunm*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima*, *Tortrix viridana*, *Cnaphalocerus* spp.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis* and *Costelytra zealandica*.

From the order of the Hymenoptera, for example, *Diprion* spp., *Hoplocampa* spp., *Lasius* spp., *Monomoriumpharaonis* and *Vespa* spp.

From the order of the Diptera, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae*, *Tipula paludosa*, *Hylemyia* spp. and *Liriomyza* spp.

From the order of the Siphonaptera, for example, *Xenopsylla cheopis* and *Ceratophyllus* spp.

From the order of the Arachnida, for example, *Scorpio maurus*, *Latrodectus mactans*. *Acarus siro*, *Argas* spp., *Omithodoros* spp., *Dernanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Hemitarsonemus* spp., *Brevipalpus* spp.

The phytoparasitic nematodes include, for example, *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The active compounds according to the invention have high insecticidal and acaridical activity after foliar and soil application.

They can be employed particularly successfully for controlling plant-damaging insects, such as, for example, against the larvae of the mustard beetle (*Phaedon cochleariae*), against the larvae of the green rice leafhopper (*Nephotettix cincticeps*) and against the larvae of the green peach aphid (*Myzus persicae*).

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulationsin polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example ligninsulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, filberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfiuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziramn and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-αmethyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5-(4H)-one, 8-(1,1-dimethylethyl)-N-ethyl-N-propyl-1,4-dioxaspiro[4.5]decane-2-methanamine, 8-hydroxyquinolinesulphate,
9H-xanthene-2-[(phenylamino)-carbonyl]-9-carboxylihydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl[(4-chlorophenyl)-azo]-cyanoacetate,
potassium bicarbonate,
methanetetrathiol-sodiumsalt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran)-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses,
halofenozide, HCH, heptenophos, hexaflumuron, hexythiazox, hydroprene,
imidacloprid, isazofos, isofenphos, isoxathion, ivermectin, nuclear polyhedrosis viruses,
lambda-cyhalothrin, lufenuron,
malathion, mecarbam, metaldehyde, methamidophos, *Metharhizium anisopliae, Metharhizium* flavoviride, methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,
*Paecilomyces fumosoroseus,* parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos,
ribavirin,
salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*
YI 5302,
zeta-cypermethrin, zolaprofos,
(1R-cis)[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate.
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5] dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3 (4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention can be used as defoliants, desiccants, haulm killers and, especially, as weed killers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus* and *Taraxacum*.

Dicotyledonous cultures of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis* and *Cucurbita*.

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus Apera, Aegilopus* and *Phalaris*.

Monocotyledonous cultures of the genera: *Oryza, Zea, Triticum, Hordeum, Avena, Secale, Sorghum, Panicum, Saccharum, Ananas, Asparagus* and *Allium*.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for the control of weeds in perennial crops for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual crops.

The compounds of the formula (I) according to the invention have strong herbicidal activity and a broad activity spectrum when applied to the soil and to the above-ground parts of the plants. To a certain extent, they are also suitable for the selective control of monocotyledonous and dicotyledonous weeds in moncotyledonous and dicotyledonous crops, both pre-emergence and post-emergence.

For the control of weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafanedin, azimsulfuron, benazolin(-ethyl), benfuresate, bensulfuron(-methyl), bentazon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clethodim, clodinafop(-propargyl), clomazone, clomeprop, clopyralid, clopyrasulfuron(-methyl), cloransulam (-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethathyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, etobenzanid, fenoxaprop(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluciathet (-methyl), fluthiamide, fomesafen, glufosinate(-ammonium), glyphosate(-isopropylammonium), halosafen, haloxyfop (-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, perlagon acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-ethyl), quizalofop(-p-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyornma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) und Acaridida (Astigmata), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds of the formula (1) according to the invention also have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Den-*

*drobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenopterons, such as

*Sirex juvencus, Urocerus gigas, Urocerus gigas taignus, Urocerus augur*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptoternes formosanus.*

Bristletails, such as

*Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and wood processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such, as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention is illustrated by the examples below.

EXAMPLE

Myzus Test

Solvent: 1 part by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Cabbage leaves (*Brassica oleracea*) which are heavily infested by peach aphids (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compound of the Preparation Examples shows good activity:

TABLE

| Active compound | Plant-damaging insects Myzus test | |
|---|---|---|
| | Concentration of active compound in % | Kill in % after 6 days |
| Ex. I-1-a-4 | 0.1 | 95 |

EXAMPLE

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Rice seedlings (*Oryza sativa*) are treated by being dipped into the preparation of active compound of the desired concentration and are populated with larvae of the green rice leaf-hopper (*Nephotettix cincticeps*) while the leaves are still moist.

After the desired period of time, the kill in % is determined. 100% means that all leaf-hoppers have been killed; 0% means that none of the leaf-hoppers have been killed.

In this test, for example, the following compounds of the Preparation Examples show good activity:

TABLE

Plant-damaging insects
Nephotettix test

| Active compound | Active compound in % | Kill in % after 6 days |
|---|---|---|
| Ex. I-1-a-3 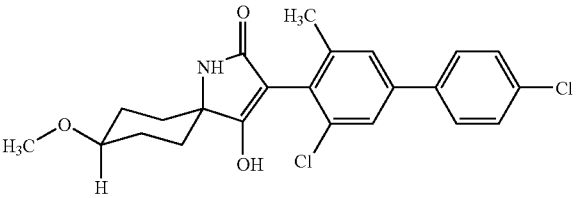 | 0.1 | 100 |
| Ex. I-1-a-4 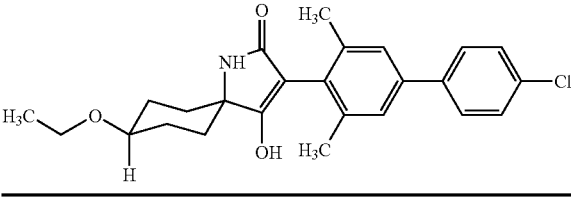 | 0.1 | 100 |

EXAMPLE

Phaedon Larvae Test
Solvent: 7 parts by weights of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all aphids have been killed; 0% means that none of the aphids have been killed.

In this test, for example, the following compounds of the Preparation Examples shows good activity:

TABLE

Plant-damaging insects
Phaedon larvae test

| Active compound | Concentration of active compound in % | Kill in % after 7 days |
|---|---|---|
| Ex. I-1-a-3 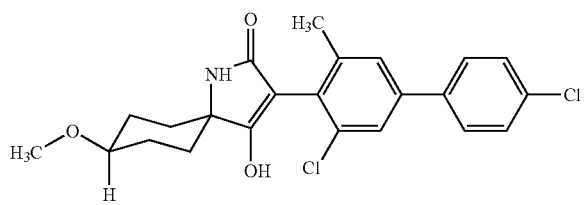 | 0.1 | 100 |
| Ex. I-1-a-4 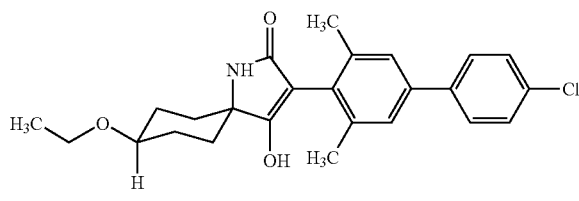 | 0.1 | 100 |

EXAMPLE

Post-Emergence Test
Solvent: 5 parts by weight of acetone
Emulsifier: 1 part by weight of alkylaryl polyglycol ether To produce a suitable preparation of active compound, one part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. After 3 weeks, the degree of damage to the plants is rated in % damage in comparison to the development of the untreated control.

The figures denote:
0%=no effect (like untreated control)
100%=total destruction

| Post-emergence/greenhouse | | | | |
|---|---|---|---|---|
| g of ai./ha | Sugar beet | Avena fatua | Setaria | Sinapis |
| Ex. I-1-a-2 | 250 | 20 | 70 | 100 | 70 |

| | g of ai./ha | Avena fatua | Setaria | Abutilon | Amaranthus |
|---|---|---|---|---|---|
| Ex. I-1-a-4 | 250 | 90 | 100 | 80 | 80 |

EXAMPLE I-1-a-1

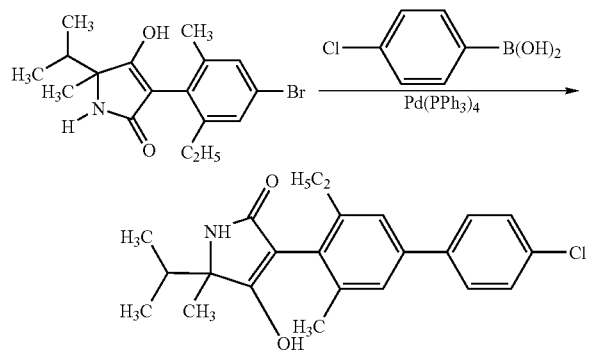

Under argon, 1.1 g of 3-[(4-bromo-2-ethyl-6-methyl)-phenyl]-5-isopropyl-5-methyl-pyrrolidin-2,4-dione according to Example I-1-a-4 from WO 97/02243 in 20 ml of 1,2-dimethoxyethane are admixed with 0.6 g of 4-chlorophenylboronic acid and 180 mg of tetrakis(triphenylphosphine)palladium. The mixture is stirred at 20° C. for 15 min, 15 ml of 20% strength aqueous sodium carbonate solution are then added, and the mixture is stirred at 80° C. for one day. The mixture is then filtered, the filtrate is admixed with water and the aqueous phase is acidified. Filtration with suction gives 0.75 g of product (65% of theory).

m.p.: 245° C.

By the method of Example (I-1-a-1) and (I-1-a-43), and/or in accordance with the general procedures for preparing compounds of the formula (I-1-a), the following compounds of the formula (I-1-a) are obtained:

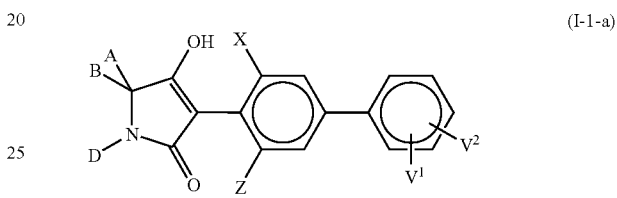

(I-1-a)

EXAMPLE

Pre-Emergence Test
Solvent: 5 parts by weight of acetone
Emulsifier: 1 part by weight of alkylaryl polyglycol ether To produce a suitable preparation of active compound, one part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. Advantageously, the amount of water per unit area is kept constant. The active compound concentration in the preparation is not important, only the active compound application rate per unit area matters. After three weeks, the degree of damage to the plants is rated in % damage in comparison to the development of the untreated control.

The figures denote:
0%=no effect (like untreated control)
100%=total destruction

| Pre-emergence/greenhouse | | | | |
|---|---|---|---|---|
| g of ai./ha | Alopecurus | Setaria | Amaranthus | Galium |
| Ex. I-1-a-3 | 250 | 100 | 100 | 100 | 90 |

| Ex. No. | X | Z | $V^1$ | $V^2$ | D | A | B | m.p.° C. | isomer |
|---|---|---|---|---|---|---|---|---|---|
| I-1-a-2 | $CH_3$ | $CH_3$ | 4-Cl | H | H | —$(CH_2)_2$—$CHOCH_3$—$(CH_2)_2$— | | >240 | β |
| I-1-a-3 | $CH_3$ | Cl | 4-Cl | H | H | —$(CH_2)_2$—$CHOCH_3$—$(CH_2)_2$— | | 211 | β |

-continued

| | | | | | Pre-emergence/greenhouse | | |
|---|---|---|---|---|---|---|---|
| I-1-a-4 | $CH_3$ | Cl | 4-Cl | H | H | —$(CH_2)_2$—$CHOC_2H_5$—$(CH_2)_2$— | >230 | β |
| I-1-a-5 | $CH_3$ | $CH_3$ | 4-Cl | H | H | —$CH_2$—O—$(CH_2)_3$— | >240 | — |
| I-1-a-6 | $C_2H_5$ | $CH_3$ | 4-Cl | H | H | $CH_3$   $CH_3$ | >240 | — |
| I-1-a-7 | $C_2H_5$ | $C_2H_5$ | 4-Cl | H | H | —$(CH_2)_2$—$CHCH_3$—$(CH_2)_2$— | 188 | β |
| I-1-a-8 | $CH_3$ | Cl | 4-Cl | H | H | —$(CH_2)_2$—O—$(CH_2)_2$— | 165–167 | — |
| I-1-a-9 | $C_2H_5$ | Cl | 4-Cl | H | H | —$(CH_2)_2$—$CHOCH_3$—$(CH_2)_2$— | >240 | β |
| I-1-a-10 | $C_2H_5$ | Cl | 4-Cl | H | H | —$(CH_2)_2$—$CHCH_3$—$(CH_2)_2$— | >240 | β |
| I-1-a-11 | $CH_3$ | Cl | 4-Cl | H | H | i-$C_3H_7$   $CH_3$ | >240 | — |
| I-1-a-12 | $CH_3$ | $CH_3$ | 4-Cl | H | H | $CH_3$   $CH_3$ | >240 | — |
| I-1-a-13 | $C_2H_5$ | $C_2H_5$ | 4-Cl | H | H | i-$C_3H_7$   $CH_3$ | 218 | — |
| I-1-a-14 | $CH_3$ | $CH_3$ | 4-Cl | H | H | —$(CH_2)_5$— | >240 | — |
| I-1-a-15 | $CH_3$ | $CH_3$ | 3-Cl | H | H | —$(CH_2)_2$—$CHOCH_3$—$(CH_2)_2$— | 135 | β |
| I-1-a-16 | $CH_3$ | $CH_3$ | 2-Cl | H | H | —$(CH_2)_2CHOCH_3(CH_2)_2$— | >245 | β |
| I-1-a-17 | $CH_3$ | $CH_3$ | 4-Cl | H | H | —$(CH_2)_2$—O—$(CH_2)_2$— | >235 | — |
| I-1-a-18 | $CH_3$ | $CH_3$ | 4-Cl | H | H | —$(CH_2)_2CHOC_2H_5(CH_2)_2$— | >245 | β |
| I-1-a-19 | $CH_3$ | $CH_3$ | 4-Cl | H | H | —$(CH_2)_2$—$CHCH_3$—$(CH_2)_2$— | >245 | β |
| I-1-a-20 | $CH_3$ | $CH_3$ | 4-Cl | H | H | —$CH_2$—$CHCH_3$—$(CH_2)_3$— | >245 | β |
| I-1-a-21 | $CH_3$ | $CH_3$ | 4-Cl | H | —$(CH_2)_4$— | H | >240 | — |
| I-1-a-22 | $CH_3$ | $CH_3$ | 4-Cl | H | i-$C_3H_7$ | H   H | >249 | — |
| I-1-a-23 | $CH_3$ | $CH_3$ | 2-$CH_3$ | 5-$CH_3$ | H | —$CH_2$—O—$(CH_2)_3$— | 148 | — |
| I-1-a-24 | $CH_3$ | $CH_3$ | 2-$CH_3$ | 6-$CH_3$ | H | —$CH_2$—O—$(CH_2)_3$— | >250 | — |
| I-1-a-25 | $CH_3$ | $CH_3$ | 3-$CH_3$ | 5-$CH_3$ | H | —$CH_2$—O—$(CH_2)_3$— | >250 | — |
| I-1-a-26 | $CH_3$ | Cl | 4-Cl | H | H | —$(CH_2)_5$— | >250 | — |
| I-1-a-27 | $CH_3$ | Cl | 3-$CF_3$ | 5-$CF_3$ | H | —$(CH_2)_5$— | >250 | — |
| I-1-a-28 | $CH_3$ | Cl | 3-$CF_3$ | H | H | —$(CH_2)_5$— | >250 | — |
| I-1-a-29 | $CH_3$ | Cl | 2-Cl | 4-Cl | H | —$(CH_2)_5$— | >250 | — |
| I-1-a-30 | $CH_3$ | Cl | 3-Cl | 5-Cl | H | —$(CH_2)_5$— | >250 | — |
| I-1-a-31 | $C_2H_5$ | $C_2H_5$ | 4-Cl | H | H | —$(CH_2)_2$—$CHCH_3$—$(CH_2)_2$— | >250 | — |
| I-1-a-32 | $C_2H_5$ | $C_2H_5$ | 3-$CF_3$ | 5-$CF_3$ | H | —$(CH_2)_2CHCH_3$—$(CH_2)_2$— | 242–244 | β |
| I-1-a-33 | $C_2H_5$ | $C_2H_5$ | 4-$CF_3$ | H | H | —$(CH_2)_2$—$CHCH_3$—$(CH_2)_2$— | >250 | β |
| I-1-a-34 | $CH_3$ | $CH_3$ | 4-Cl | H | H | i-$C_3H_7$   $CH_3$ | Wax | — |
| I-1-a-35 | $C_2H_5$ | $C_2H_5$ | 2-Cl | 4-Cl | H | —$(CH_2)_2CHCH_3$—$(CH_2)_2$— | >250 | β |
| I-1-a-36 | $C_2H_5$ | $C_2H_5$ | 3-Cl | 5-Cl | H | —$(CH_2)_2CHCH_3$—$(CH_2)_2$— | >250 | β |
| I-1-a-37 | $CH_3$ | $CH_3$ | 2-Cl | 4-Cl | H | i-$C_3H_7$   $CH_3$ | 115–117 | — |
| I-1-a-38 | $CH_3$ | $CH_3$ | 3-Cl | 5-Cl | H | i-$C_3H_7$   $CH_3$ | 233–234 | — |
| I-1-a-39 | $C_2H_5$ | Cl | 4-Cl | H | H | $CH_3$   $CH_3$ | >250 | — |
| I-1-a-40 | $C_2H_5$ | Cl | 3-Cl | 5-Cl | H | $CH_3$   $CH_3$ | 125–127 | — |
| I-1-a-41 | $CH_3$ | Cl | 4-Cl | H | H | $CH_3$   $CH_3$ | >250 | — |
| I-1-a-42 | $CH_3$ | Cl | 3-$CF_3$ | 5-$CF_3$ | H | $CH_3$   $CH_3$ | >250 | — |
| I-1-a-43 | $CH_3$ | $CH_3$ | 4-Cl | H | H | i-$C_3H_7$   $CH_3$ | >250 | — |
| I-1-a-44 | $CH_3$ | $CH_3$ | 4-$CH_3$ | H | H | —$(CH_2)_2$—$CHOCH_3$—$(CH_2)_2$— | >235 | β |
| I-1-a-45 | $CH_3$ | $CH_3$ | 2-$CH_3$ | 5-F | H | —$(CH_2)_2$—$CHOCH_3$—$(CH_2)_2$— | >235 | β |
| I-1-a-46 | $CH_3$ | $CH_3$ | 2-$CH_3$ | 5-$CH_3$ | H | —$(CH_2)_2$—$CHOCH_3$—$(CH_2)_2$— | 168 | β |
| I-1-a-47 | $CH_3$ | $CH_3$ | 2-$OCH_3$ | H | H | —$(CH_2)_2$—$CHOCH_3$—$(CH_2)_2$— | | β |
| I-1-a-48 | $CH_3$ | $CH_3$ | 3-$CH_3$ | 5-$CH_3$ | H | —$(CH_2)_2$—$CHOCH_3$—$(CH_2)_2$— | 238 | β |
| I-1-a-49 | $CH_3$ | $CH_3$ | 2-Cl | 4-Cl | H | —$(CH_2)_2$—$CHOCH_3$—$(CH_2)_2$— | 188 | β |
| I-1-a-50 | $CH_3$ | $CH_3$ | 2-Cl | 3-Cl | H | —$(CH_2)_2$—$CHOCH_3$—$(CH_2)_2$— | >235 | β |

EXAMPLE I-1-b-1

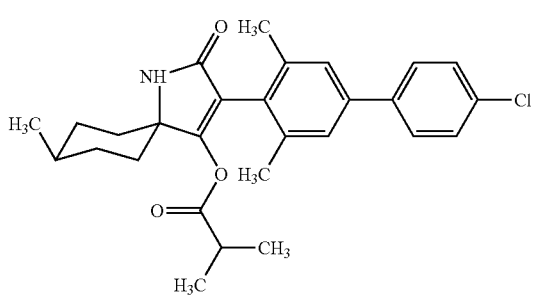

First 0.67 ml (4.8 mmol) of triethylamine and then, at reflux temperature, 0.5 ml (0.005 mol) of isobutyryl chloride in 5 ml of absolute ethyl acetate are added to 1.58 g of the compound of Example I-1-a-19 in 40 ml of absolute ethyl acetate. Stirring is continued at this temperature until the reaction has ended (monitored by thin-layer chromatography). The mixture is then concentrated and the residue is taken up in methylene chloride, washed twice with 30 ml of 0.5 N NaOH, dried and concentrated. The residue is recrystallized from methyl tert-butyl ether (MTBE)/n-hexane. Yield 1.27 g (68% of theory). m.p.:>247° C.

By the method of Example (I-1-b-1), and/or in accordance with the general procedures for preparing compounds of the formula (I-1-b), the following compounds of the formula (I-1-b) are obtained:

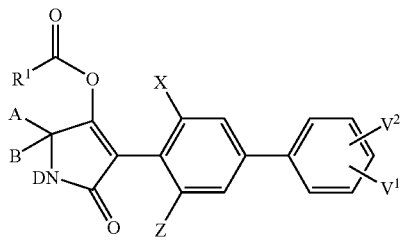

(I-1-b)

| Ex. No. | X | Z | V¹ | V² | D | A | B | R¹ | m.p. °C. | isomer |
|---|---|---|---|---|---|---|---|---|---|---|
| I-1-b-2 | $CH_3$ | $CH_3$ | 4-Cl | H | H | —$(CH_2)_2$—$CHCH_3$—$(CH_2)_2$— | | $H_5C_2$—O—$CH_2$— | >247 | β |
| I-1-b-3 | $CH_3$ | $CH_3$ | 4-Cl | H | H | —$CH_2$—$CHCH_3$—$(CH_2)_3$— | | $i$-$C_3H_7$— | >247 | β |
| I-1-b-4 | $CH_3$ | $CH_3$ | 4-Cl | H | H | —$CH_2$—$CHCH_3$—$(CH_2)_3$— | | Cl—C₆H₄— | >254 | β |
| I-1-b-5 | $CH_3$ | $CH_3$ | 4-Cl | H | H | —$CH_2$—$CHOCH_3$—$(CH_2)_2$— | | $i$-$C_3H_7$— | 236 | β |
| I-1-b-6 | $CH_3$ | $CH_3$ | 4-Cl | H | H | —$CH_2$—$CHOCH_3$—$(CH_2)_2$— | | 2-Cl-pyridin-5-yl | >247 | β |
| I-1-b-7 | $CH_3$ | $CH_3$ | 3-Cl | H | H | —$CH_2$—$CHOCH_3$—$(CH_2)_2$— | | $i$-$C_3H_7$— | 238 | β |

EXAMPLE I-1-c-1

At −10° C. to 0° C., 0.15 g of chloroformic acid in 5 ml of methylene chloride is added to 0.35 g of the compound of Example I-1-a-12 and 0.15 ml of triethylamine in 30 ml of methylene chloride, and the mixture is stirred at room temperature for 2 hours.

The reaction mixture is filtered through silica gel using methylene chloride/ethyl acetate 5:3 as mobile phase, and is then concentrated and dissolved in a little methylene chloride, and the product is precipitated out by addition of hexane.

Yield 0.23 g (56% of theory). m.p.: 129° C.

By the method of Example (I-1-c-1), and/or according to the general procedures for preparing compounds of the formula (I-1-c), the following compounds of the formula (I-1-c) are obtained:

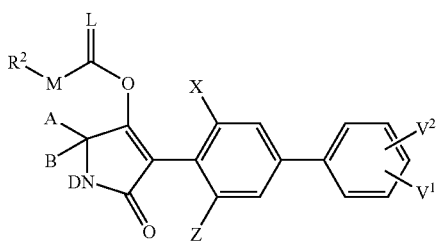

(I-1-c)

| Ex.-No. | X | Z | V¹ | V² | D | A | B | L | M | R² | m.p. °C. | isomer |
|---|---|---|---|---|---|---|---|---|---|---|---|---|
| I-1-c-2 | $CH_3$ | $CH_3$ | 4-Cl | H | H | —$(CH_2)_2$—$CHCH_3$—$(CH_2)_2$— | | O | O | $C_2H_5$— | >240 | β |
| I-1-c-3 | $CH_3$ | $CH_3$ | 4-Cl | H | H | —$CH_2$—$CHCH_3$—$(CH_2)_3$— | | O | O | $C_2H_5$— | >240 | β |
| I-1-c-4 | $CH_3$ | $CH_3$ | 4-Cl | H | H | —$(CH_2)_2$—$CHOCH_3$—$(CH_2)_2$— | | O | O | $C_2H_5$ | 202 | β |

-continued (I-1-c)

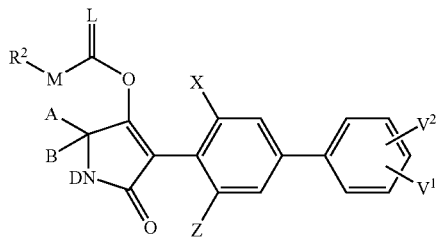

| Ex.-No. | X | Z | V¹ | V² | D | A | B | L | M | R² | m.p. °C. | isomer |
|---|---|---|---|---|---|---|---|---|---|---|---|---|
| I-1-c-5 | $CH_3$ | $CH_3$ | 3-Cl | H | H | —$(CH_2)_2$—$CHOCH_3$—$(CH_2)_2$— | | O | O | $C_2H_5$— | 214 | β |
| I-1-c-6 | $CH_3$ | $CH_3$ | 3-Cl | H | H | —$(CH_2)_2$—$CHOCH_3$—$(CH_2)_2$— | | O | O | 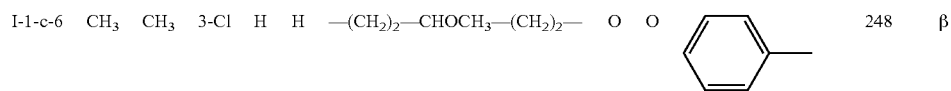 | 248 | β |
| I-1-c-7 | $CH_3$ | $CH_3$ | 3-Cl | H | H | —$(CH_2)_2$—$CHOCH_3$—$(CH_2)_2$— | | O | O | 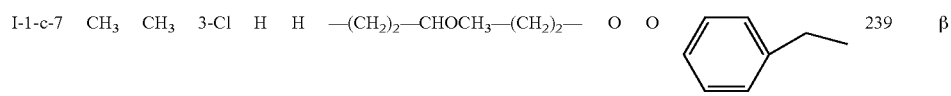 | 239 | β |

EXAMPLE I-2-a-1

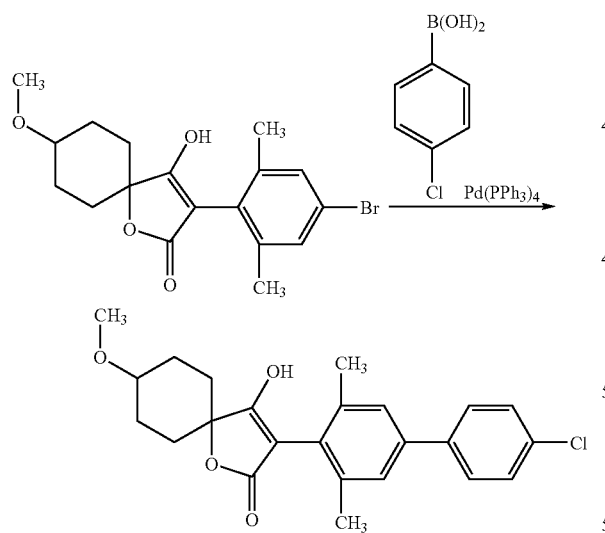

1.0 g (2.6 mmol) of 3-[(2,6-dimethyl-4-bromo)-phenyl]-5,5-[(3-methoxy)-pentamethylene]-4-hydroxy-Δ³-dihydrofuran-2-one according to Example I-2-a-15 from WO 97/02243 is suspended in 20 ml of diethoxyethane, 0.5 g (3.2 mmol) of 4-chlorophenylboronic acid and 180 mg (0.156 mmol) of tetrakis(triphenylphosphine)palladium are added and the mixture is stirred at room temperature for 15 minutes, after which 13 ml of 20% strength sodium carbonate solution are added, and stirring is continued at 80° C. for 24 h.

For work-up, the mixture was concentrated, partitioned between aqueous citric acid and methylene chloride, dried and concentrated. For further purification, the crude product was partitioned between 1N NaOH and methylene chloride, the aqueous phase was acidified and the precipitated product was filtered off with suction and dried.

Yield: 0.38 g (35% of theory) of a crystalline solid m.p.: 215–217° C.

EXAMPLE I-2-a-5

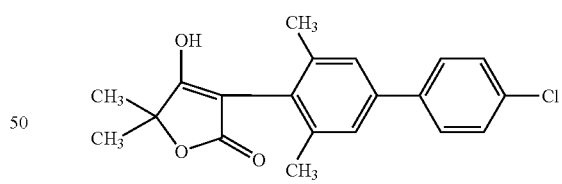

9.4 ml of 1 M solution of potassium tert-butoxide in DMF are slowly added dropwise to 7.82 mmol of the compound of Example (III-1) in 10 ml of DMF, and the mixture is stirred at room temperature overnight. The solvent is distilled off, the residue is taken up in water and acidified with dilute hydrochloric acid. The mixture is stirred for another 2 hours and then filtered off with suction.

Yield: 2.78 g, m.p. 285–287° C.

By the method of Example (I-2-a-1) and (I-2-a-5), and in accordance with the general procedures for preparing compounds of the formula (I-2-a) the following compounds of the formula (I-2-a) are obtained:

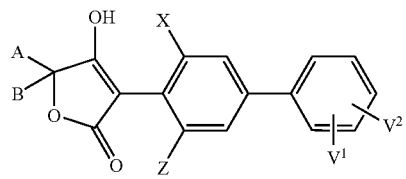

(I-2-a)

| Ex. No. | X | Z | V¹ | V² | A | B | m.p. °C |
|---|---|---|---|---|---|---|---|
| I-2-a-2 | Cl | H | 4-Cl | H | | —(CH$_2$)$_2$—CHOCH$_3$—(CH$_2$)$_2$— | 223–225 |
| I-2-a-3 | CH$_3$ | Cl | 4-Cl | H | | —(CH$_2$)$_2$—CHOCH$_3$—(CH$_2$)$_2$— | 157–160 |
| I-2-a-4 | C$_2$H$_5$ | CH$_3$ | 4-Cl | H | | —(CH$_2$)$_2$—CHOCH$_3$—(CH$_2$)$_2$— | 212–215 |
| I-2-a-5 | CH$_3$ | CH$_3$ | 4-Cl | H | CH$_3$ | CH$_3$ | 285–287 |
| I-2-a-6 | CH$_3$ | CH$_3$ | 4-Cl | H | | —(CH$_2$)$_4$— | 263–266 |
| I-2-a-7 | CH$_3$ | CH$_3$ | 4-Cl | H | | —(CH$_2$)$_5$— | 242–244 |
| I-2-a-8 | CH$_3$ | CH$_3$ | 4-Cl | H | | —CH$_2$—CHCH$_3$—(CH$_2$)$_3$— | 221–223 |
| I-2-a-9 | CH$_3$ | CH$_3$ | 4-Cl | H | | —(CH$_2$)$_2$—CHCH$_3$—(CH$_2$)$_2$— | 249–251 |
| I-2-a-10 | CH$_3$ | CH$_3$ | 4-Cl | H | | —CH$_2$—O—(CH$_2$)$_3$— | 255–258 |
| I-2-a-11 | CH$_3$ | CH$_3$ | 4-Cl | H | | —(CH$_2$)$_2$—O—(CH$_2$)$_2$— | 274–276 |
| I-2-a-12 | CH$_3$ | CH$_3$ | 4-Cl | H | | —CH$_2$—CHCH$_3$—O—(CH$_2$)$_2$— | 168–170 |
| I-2-a-13 | CH$_3$ | CH$_3$ | 4-Cl | H | | —(CH$_2$)$_2$—CHOC$_2$H$_5$(CH$_2$)$_2$ | 214–217 |
| I-2-a-14 | CH$_3$ | CH$_3$ | 4-Cl | H | | 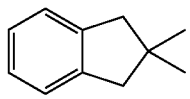 | 225–228 |

EXAMPLE I-2-b-1

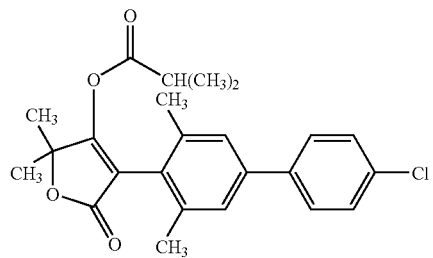

0.32 g of triethylamine and then 0.33 g of isobutyryl chloride are added to 1.03 g of the compound of Example I-2-a-5 in 20 ml of methylene chloride. The mixture is stirred overnight and then shaken with dilute aqueous citric acid and 1 N NaOH, and the organic phase is dried and concentrated. Yield 1.16 g.

$^1$H NMR (CDCl$_3$): 1.05 ppm (d, 6H); 1.55 ppm (s, 6H); 2.25 ppm (s, 6H); 2.65 ppm (m, 1H), 7.25–7.50 ppm (m, 6H).

By the method of Example (I-2-b-1), and/or in accordance with the general procedures for preparing compounds of the formula (I-2-b) the following compounds of the formula (I-2-b) are obtained:

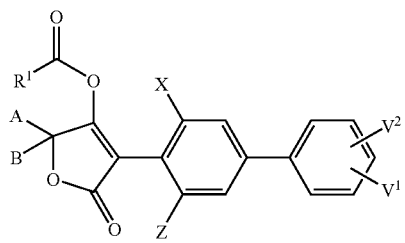

(I-2-b)

| Ex. No. | X | Z | V¹ | V² | A | B | R¹ | m.p. °C |
|---|---|---|---|---|---|---|---|---|
| I-2-b-2 | CH$_3$ | CH$_3$ | 4-Cl | H | | —(CH$_2$)$_4$— | i-C$_3$H$_7$— | oil |
| I-2-b-3 | CH$_3$ | CH$_3$ | 4-Cl | H | | —(CH$_2$)$_5$— | i-C$_3$H$_7$— | oil |
| I-2-b-4 | CH$_3$ | CH$_3$ | 4-Cl | H | | —CH$_2$—CHCH$_3$—(CH$_2$)$_3$— | i-C$_3$H$_7$— | oil |
| I-2-b-5 | CH$_3$ | CH$_3$ | 4-Cl | H | | —(CH$_2$)$_2$—CHCH$_3$—(CH$_2$)$_2$— | i-C$_3$H$_7$— | oil |
| I-2-b-6 | CH$_3$ | CH$_3$ | 4-Cl | H | | —CH$_2$—O—(CH$_2$)$_3$— | i-C$_3$H$_7$— | oil |
| I-2-b-7 | CH$_3$ | CH$_3$ | 4-Cl | H | | —(CH$_2$)$_2$—O—(CH$_2$)$_2$— | i-C$_3$H$_7$— | oil |

-continued (I-2-b)

| Ex. No. | X | Z | V¹ | V² | A | B | R¹ | m.p. ° C. |
|---|---|---|---|---|---|---|---|---|
| I-2-b-8 | $CH_3$ | $CH_3$ | 4-Cl | H | —$CH_2$—$CHCH_3$—O—$(CH_2)_2$— | | i-$C_3H_7$— | oil |
| I-2-b-9 | $CH_3$ | $CH_3$ | 4-Cl | H | —$(CH_2)_2$—$CHOC_2H_5$—$(CH_2)_2$— | | i-$C_3H_7$— | oil |

EXAMPLE I-2-c-1

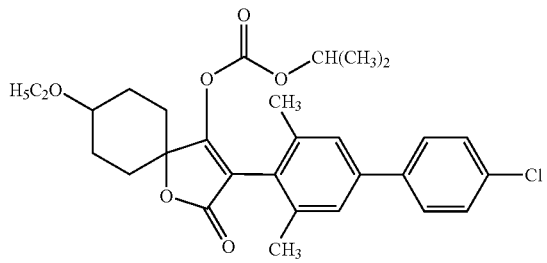

By the method of Example (I-2-b-1), the compound shown above is obtained starting from the compound of Example (I-2-a-13) and isopropyl chloroformate.

EXAMPLE I–3-a-1

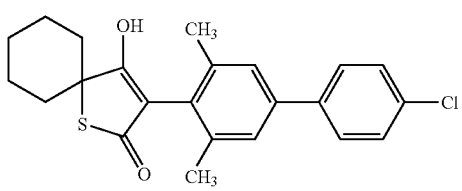

45.0 g (81 mmol) of the compound of Example (IV-1) in 91 ml of trifluoroacetic acid and 210 ml of toluene are heated at reflux overnight. The mixture is concentrated and the residue is then taken up in 200 ml of MTBE and 600 ml of water and adjusted to pH 14 by addition of NaOH. The organic phase is added dropwise to 1l of 1N HCl, the mixture is stirred for 2 hours, the product is filtered off with suction, washed with cyclohexane and dried. Yield 18.3 g (57% of theory) m.p.:>250° C.

EXAMPLE I-3-b-1

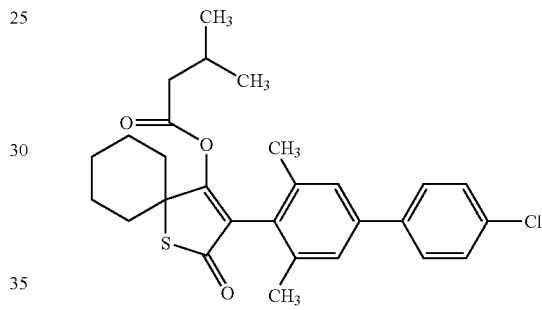

With ice-cooling, a solution of 0.79 ml of isovaleryl chloride in 3 ml of absolute methylene chloride is added dropwise to 2.0 g of the compound of Example (I-3-a-1) and 1.04 ml of triethylamine in 15 ml of absolute methylene chloride, and the mixture is stirred at room temperature for 2 hours. The mixture is washed with 10% strength aqueous citric acid and extracted with methylene chloride. The organic phase is washed with 1N NaOH, dried and concentrated. Yield 2.1 g (87% of theory) of an oil.

$^1$H NMR (400 MHz, $CDCl_3$):δ=0.9/(dd, 6 H, CH/$CH_3)_2$, 1.4–2.0 (m, 10H, cyclohexyl) 2.15 (s, 6H, 2×Ar—$CH_3$), 7.4–7.7 (m, 6H, Ar—H) ppm.

EXAMPLE I-3-c-1

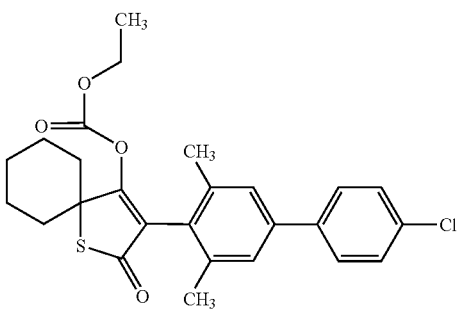

By the method of Example (I-3-b-1) the compound shown above is obtained by reacting the compound of Example (I-3-a-1) with ethyl chloroformate. Yield 2.1 g (89% of theory). m.p. 167 to 170° C.

EXAMPLE (I-5-a-1)

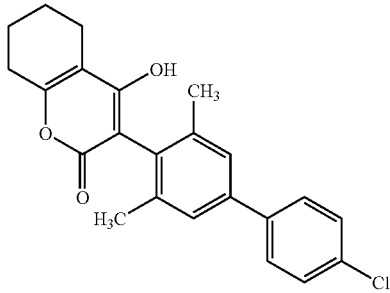

1.8 g of 4-chlorophenylboronic acid and 266.3 mg of bis(triphenylphosphine)-palladium(II) chloride are added to 2.6 g of the compound of Example (I-5-a-1) from WO 97/02 243 in 21 ml of dimethoxyethane and 18 ml of 1N Na$_2$CO$_3$ solution. The mixture is stirred at reflux overnight, acidified with dilute HCl and concentrated. The residue is purified by silica gel chromatography (mobile phase cyclohexane/ethyl acetate 4/1→2/1). Yield 2.55 g (89% of theory); m.p.: >250° C.

EXAMPLE (I-5-a-2)

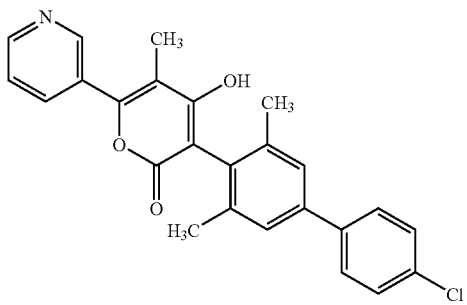

By the method of Example I-5-a-1, the compound shown above is obtained starting from the compound of Example (I-5-a-6) from WO 97/02 243. m.p. 107–108° C.

EXAMPLE I-7-a-1

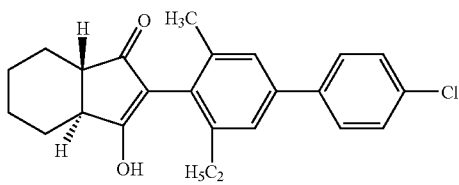

1.5 g (4.3 mmol) of the compound of the formula

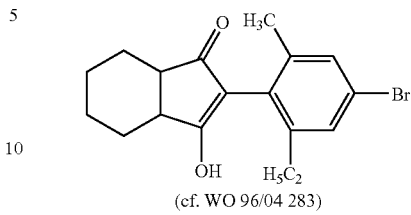

(cf. WO 96/04 283)

are dissolved in 10 ml of dimethoxyethane and admixed with 10 ml of 1 M Na$_2$CO$_3$ solution. 1.0 g (6.45 mmol) of p-chlorophenylboronic acid and finally, as catalyst, 254 mg (0.22 mmol) of Pd(PPh$_3$)$_4$ (Ph=phenyl) are added. The mixture is heated at reflux overnight and then filtered, and the filter cake is rinsed with ethyl acetate. The filtrate is admixed with water and extracted 3 times each with ethyl acetate and methyl tert-butyl ether (MTBE). The combined organic phases are washed with water and saturated NaCl solution, dried and concentrated.

Crude yield: 1.85 g.

Silica gel column chromatography using cyclohexane/ethyl acetate 15/1 gives 100 mg of the compound shown above.

Two other fractions (300 mg and 400 mg) of rotamers of the cis isomer are obtained.

EXAMPLE I-7-a-2

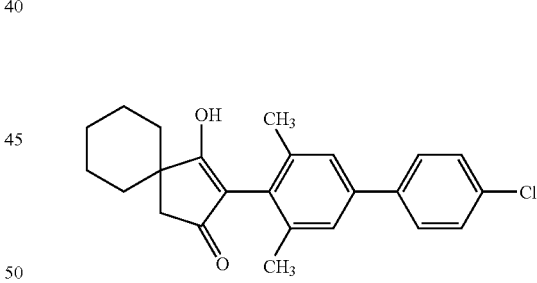

20.5 g of the compound of Example (X-1) in 50 ml of absolute DMF are admixed with 8.44 g of potassium tert-butoxide and heated at 80° C. for 1 hour. With ice-cooling, the mixture is slowly added to 2 l of 1N HCl. The mixture is extracted with methylene chloride and the extract is dried and concentrated. Yield 18 g (95% of theory), m.p.: 192–195° C.

By the method of Example (I-7-a-1) and (I-7-a-2), and/or in accordance with the general procedures for preparing compounds of the formula (I-7-a) the following compounds of the formula (I-7-a) are obtained:

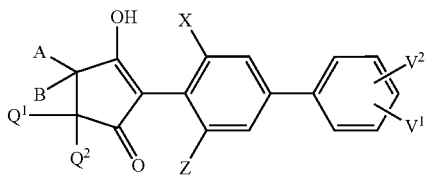

| Ex.-No. | X | Z | V¹ | V² | B | A | Q¹ | Q² | m.p. °C. |
|---|---|---|---|---|---|---|---|---|---|
| I-7-a-3 | CH₃ | CH₃ | 3-Cl | H | | —(CH₂)₅— | H | H | >250 |
| I-7-a-4 | CH₃ | CH₃ | 4-Cl | H | H | —(CH₂)₄— | H | H | >250 |
| I-7-a-5 | CH₃ | CH₃ | 3-Cl | H | H | —(CH₂)₄— | H | H | 211–213 |
| I-7-a-6 | CH₃ | CH₃ | 4-Cl | H | | —(CH₂)₃—CHCH₃—CH₂— | H | H | 243–244 |
| I-7-a-7 | CH₃ | CH₃ | 3-Cl | H | | —(CH₂)₃—CHCH₃—CH₂— | H | H | wax |

EXAMPLE I-7-b-1

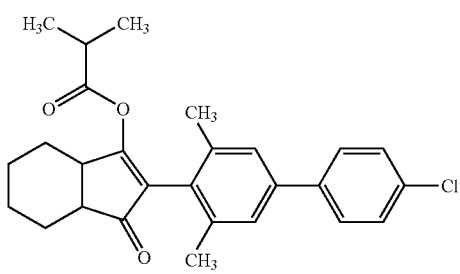

By the method of Example (I-3-b-1), the compound shown above is obtained by reacting the compound of Example (I-7-a-1) with isobutyryl chloride. m.p.: oil.

¹H NMR (400 MHz; DMSO): δ=0.9–1.0 (d, 6H, HC—CH₃); 1.2–2.0 (m, 8H, cyclohexyl-H); 2.1 2.15 (s, 6H, 2×ArCH₃); 2.65 (m, 1H, CHCH₃); 7.4 (s, 2H, Ar—H); 7.5–7.7 (d, 4H, Ar—H) ppm.

EXAMPLE I-7-b-2

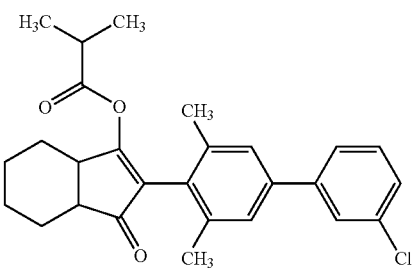

By the method of Example (I-3-b-1) the compound shown above is obtained as an oil by reacting the compound of Example (I-7-a-5) with isobutyryl chloride.

¹H NMR (400 MHz; DMSO): δ=1–1.1 (d, 6H, CH—CH₃), 42.0 (m, 8H, cyclohexyl-H); 2.15–2.2 (s, 6H, 2×ArCH₃); 2.6 (m, 1H, CH—CH₃); 2.9–3.4 (m, 2H, cyclohexyl C—H); 7.3–7.6 (m, 6H, Ar—H) ppm.

By the method of Example (I-7-b-1), and/or in accordance with the general procedures for preparing compounds of the formula (I-7-b), the following compounds of the formula (I-7-b) are obtained:

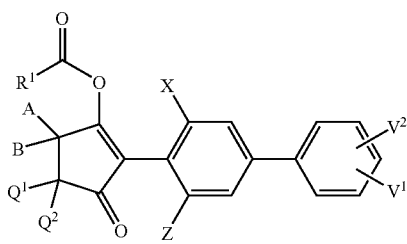

| Ex. No. | X | Z | V¹ | V² | B | A | Q¹ | Q² | R¹ | m.p. °C. |
|---|---|---|---|---|---|---|---|---|---|---|
| I-7-b-3 | CH₃ | CH₃ | 4-Cl | H | | —(CH₂)₅— | H | H | i-C₄H₉ | oil |

EXAMPLE I-7-c-1

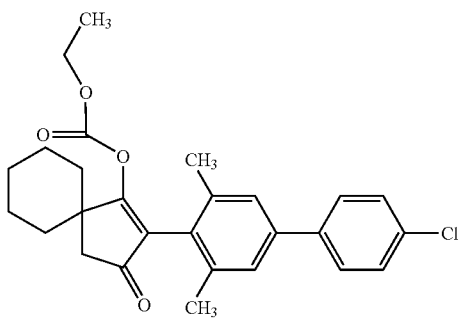

By the method of Example (I-3-b-1), the compound shown above is obtained as a wax by reacting the compound of Example (I-7-a-2) with ethyl chloroformate.

EXAMPLE I-8-a-1

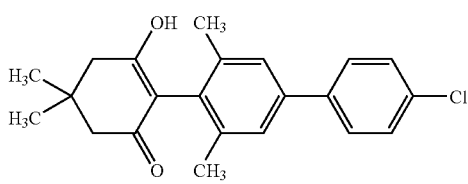

6.0 g of the compound of Example (XI-1) are initially charged in 20 ml of DMF, admixed with 2.63 g of potassium tert-butoxide and heated at 80° C. for 1 hour. With ice-cooling, the mixture is then slowly added to 1 l of 1N HCl, and the product is filtered off with suction and dried. Yield 5.15 g (93% of theory). m.p.: 222–224° C.

EXAMPLE I-8-a-2

By the method of Example (I-8-a-1),

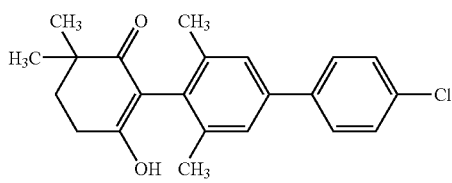

of m.p. 117–122° C. is obtained.

EXAMPLE I-8-b-1

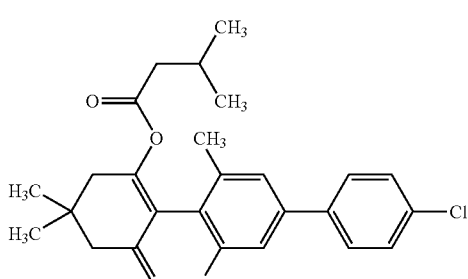

By the method of Example (I-3-b-1), the compound shown above is obtained as an oil by reacting the compound of Example (I-8-a-1) and isovaleryl chloride.

$^1$H NMR (400 MHz; CDCl$_3$): δ=0.55 (d, 6H, CH(CH$_3$)$_2$), 1.2 (s, 6H, C(CH$_3$)$_2$), 1.6 (m, 1H, CH(CH$_3$)$_2$), 2.1 (s, 6H, 2×Ar—CH$_3$), 7.3–7.65 (m, 6H, Ar—H) ppm.

EXAMPLE I-8-b-2

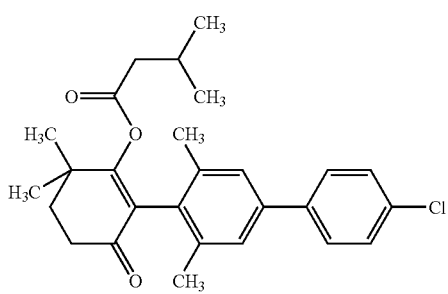

By the method of Example (I-3-6-1), the compound shown above is obtained as an oil by reacting the compound of Example (I-8-a-2) with isovaleryl chloride.

$^1$H NMR (400 MHz; CDCl$_3$): δ=0.55 (d, 6H, CH(CH$_3$)$_2$), 1.2 (s, 6H, C(CH$_3$)$_2$), 1.6 (m, 1H, CH(CH$_3$)$_2$), 2.0;2.7 (t, 2×2H, CH$_2$—CH$_2$), 2.05 (s, 6H, 2×Ar—CH$_3$), 7.3–7.65 (m, 6H, Ar—H) ppm.

EXAMPLE I-8-c-1

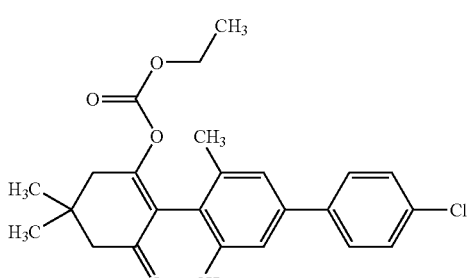

By the method of Example (I-3-b-1), the compound shown above is obtained as a wax-like substance by reacting the compound of Example (I-8-a-1) with ethyl chloroformate.

$^1$H NMR (400 MHz; CDCl$_3$):δ=1.05 (t, 3H, CH$_2$CH$_3$, 1.2 (s, 6H, C(CH$_3$)$_2$), 2.1 (s, 6H, 2×Ar—CH$_3$), 2.45;2.7 (s, 2×2H, CH$_2$), 4.1 (q, 2H, CH$_2$—CH3) 7.35–7.7 (m, 6H, Ar—H) ppm.

EXAMPLE I-8-c-2

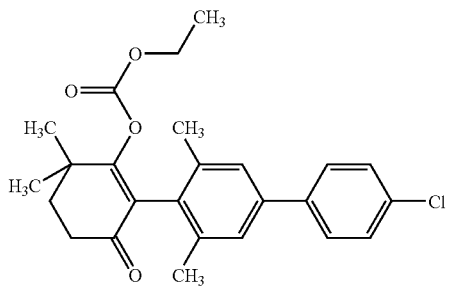

By the method of Example 1-3-b-1, the compound shown above is obtained as a wax-like substance by reacting the compound of Example (I-8-a-2) with ethyl chloroformate.

$^1$H NMR (400 MHz; CDCl$_3$):δ=1.05 (t, 3H, CH$_2$CH$_3$, 1.15 (s, 6H, C(CH$_3$)$_2$), 2.0; 2.7 (t, 2×2H, CH$_2$—CH$_2$) 2.05 (s, 6H, Qx, Ar—CH$_3$), 4.05 (q, 2H, CH$_2$—CH3) 7.3–7.7 (m, 6H, Ar—H) ppm.

EXAMPLE III-1

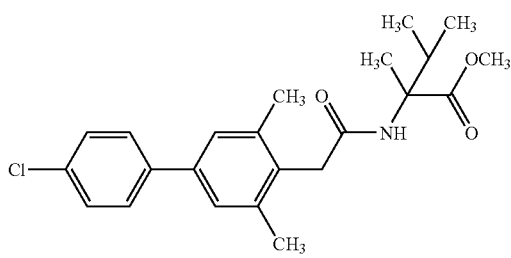

At a temperature of from 30 to 40° C., 7.75 g of the compound of Example XXIX-1 in 80 ml of methylene chloride are added dropwise to 10.3 g of concentrated sulphuric acid, and the mixture is stirred at this temperature for 2 hours. 14 ml of methanol are then added dropwise, and the mixture is stirred at 70° C. for a further 6 hours. The mixture is then poured onto 110 g of ice and extracted with methylene chloride, and the organic phase is washed with aqueous NaHCO$_3$ solution, dried and concentrated. The residue is recrystallized from MTBE/n-hexane and then purified further by silica gel column chromatography (mobile phase methylene chloride/ethyl acetate 5/3). Yield 4.24 g (50% of theory). m.p.: 142° C.

EXAMPLE II-2

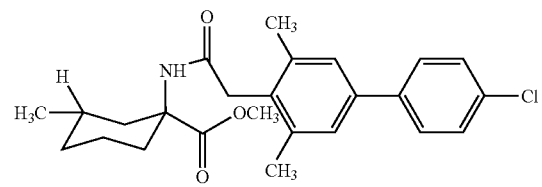

At 5–10° C., 5.86 g of 2,6-dimethyl-4-(4-chlorophenyl)-phenylacetyl chloride according to Example (XXIV-1) in 10 ml of acetonitrile are added dropwise to 4.57 g of methyl 3-methyl-1-amino-cyclohexane carboxylate×hydrochloride and 10 g of ground K$_2$CO$_3$ in 20 ml of acetonitrile, and the mixture is stirred at room temperature for 3 hours. The mixture is poured into 200 ml of ice-water and filtered off with suction, and the residue is taken up in methylene chloride, dried and concentrated. The residue is recrystallized from MTBE/n-hexane. Yield 7.12 g (83% of theory), m.p.: 169° C.

By the method of Examples (II-1) and (II-2), and/or in accordance with the general procedures for preparing compounds of the formula (II), the following compounds of the formula (II) are obtained:

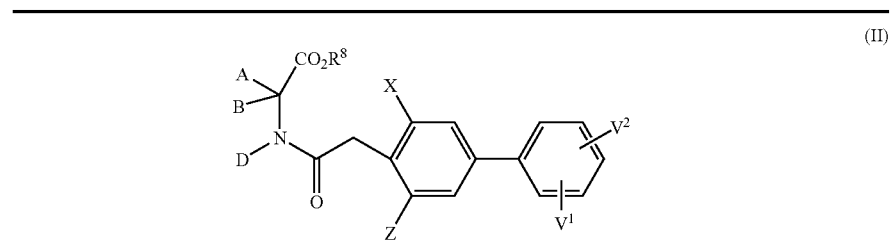

(II)

| Ex.-No. | X | Z | V$^1$ | V$^2$ | D | A | B | R$^8$ | m.p. ° C. | isomer |
|---|---|---|---|---|---|---|---|---|---|---|
| II-3 | CH$_3$ | CH$_3$ | 3-Cl | H | H | —(CH$_2$)$_2$—CHOCH$_3$—(CH$_2$)$_2$— | | CH$_3$ | 88 | β |
| II-4 | CH$_3$ | CH$_3$ | 4-Cl | H | H | —(CH$_2$)$_2$—CHOCH$_3$—(CH$_2$)$_2$— | | CH$_3$ | 127 | β |
| II-5 | CH$_3$ | CH$_3$ | 2-Cl | H | H | —(CH$_2$)$_2$—CHOCH$_3$—(CH$_2$)$_2$— | | CH$_3$ | 75 | β |
| II-6 | CH$_3$ | CH$_3$ | 4-Cl | H | H | —(CH$_2$)$_2$—O—(CH$_2$)$_2$— | | CH$_3$ | 179 | — |
| II-7 | CH$_3$ | CH$_3$ | 4-Cl | H | H | —(CH$_2$)$_2$—OCHC$_2$H$_5$—(CH$_2$)$_2$— | | CH$_3$ | 146 | β |
| II-8 | CH$_3$ | CH$_3$ | 4-Cl | H | H | —(CH$_2$)$_2$—CHCH$_3$—(CH$_2$)$_2$— | | CH$_3$ | 167 | β |
| II-9 | CH$_3$ | CH$_3$ | 4-CH$_3$ | H | H | —(CH$_2$)$_2$—CHOCH$_3$—(CH$_2$)$_2$— | | CH$_3$ | 159 | β |
| II-10 | CH$_3$ | CH$_3$ | 2-CH$_3$ | 5-F | H | —(CH$_2$)$_2$—CHOCH$_3$—(CH$_2$)$_2$— | | CH$_3$ | 138 | β |
| II-11 | CH$_3$ | CH$_3$ | 2-CH$_3$ | 5-CH$_3$ | H | —(CH$_2$)$_2$—CHOCH$_3$—(CH$_2$)$_2$— | | CH$_3$ | 71 | β |
| II-12 | CH$_3$ | CH$_3$ | 2-CH$_3$ | 3-CH$_3$ | H | —(CH$_2$)$_2$—CHOCH$_3$—(CH$_2$)$_2$— | | CH$_3$ | 133 | β |
| II-13 | CH$_3$ | CH$_3$ | 2-OCH$_3$ | H | H | —(CH$_2$)$_2$—CHOCH$_3$—(CH$_2$)$_2$— | | CH$_3$ | 156 | β |
| II-14 | CH$_3$ | CH$_3$ | 3-CH$_3$ | 5-CH$_3$ | H | —(CH$_2$)$_2$—CHOCH$_3$—(CH$_2$)$_2$— | | CH$_3$ | 169 | β |

-continued

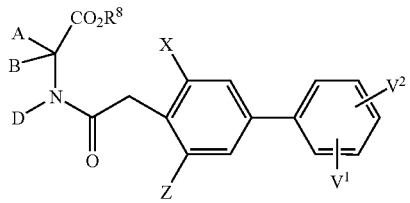

(II)

| Ex.-No. | X | Z | V$^1$ | V$^2$ | D | A | B | R$^8$ | m.p. °C. | isomer |
|---|---|---|---|---|---|---|---|---|---|---|
| II-15 | CH$_3$ | CH$_3$ | 2-Cl | 4-Cl | H | —(CH$_2$)$_2$—CHOCH$_3$—(CH$_2$)$_2$— | | CH$_3$ | 125 | β |
| II-16 | CH$_3$ | CH$_3$ | 2-Cl | 3-Cl | H | —(CH$_2$)$_2$—CHOCH$_3$—(CH$_2$)$_2$— | | CH$_3$ | 127 | β |
| II-17 | CH$_3$ | CH$_3$ | 4-Cl | H | | —(CH$_2$)$_4$— | H | C$_2$H$_5$ | oil | — |
| II-18 | CH$_3$ | CH$_3$ | 4-Cl | H | | —(CH$_2$)$_2$—S—CH$_2$— | H | C$_2$H$_5$ | 81 | — |
| II-19 | CH$_3$ | CH$_3$ | 4-Cl | H | | i-C$_3$H$_7$ | H | C$_2$H$_5$ | 119 | — |

EXAMPLE XXIX-1

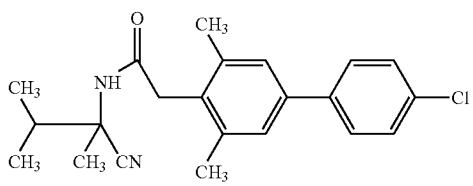

At 5–10° C., 8.79 g of 2,6-dimethyl-4-(4-chlorophenyl)-phenylacetyl chloride in 15 ml of acetonitrile are added dropwise to 3.7 g of 2-amino-2,3-dimethyl-butyronitrile and 13.8 g of ground K$_2$CO$_3$ in 30 ml of acetonitrile, and the mixture is stirred at room temperature for 3 hours. The mixture is poured into 250 ml of ice-water and filtered off with suction, and the residue is washed with water. The residue is taken up in methylene chloride, and the solution is dried and concentrated. The product is subsequently purified by silica gel chromatography (mobile phase n-hexane/ethyl acetate 3/1). Yield 8.24 g (74% of theory), m.p. 180° C.

EXAMPLE (III-1)

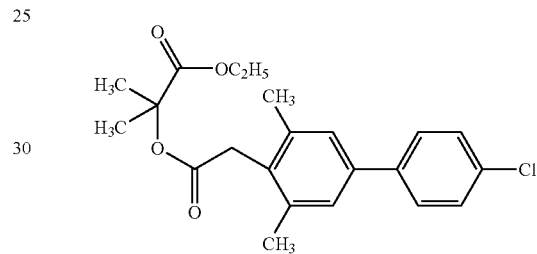

The mixture of 2.29 g of the compound of Example (XXIV-1) and 1.03 g of ethyl hydroxyisobutyrate is heated at 140° C. overnight.

GC/MS: m/e=115 (8%), 179 (34%), 229 (100%), 256 (12%), 388 (20%).

By the method of Example (III-1), and/or in accordance with the general procedures for preparing compounds of the formula (III), the following compounds of the formula (III) are obtained:

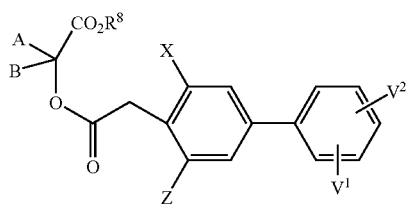

(III)

| Ex. No. | X | Z | V$^1$ | V$^2$ | A | B | R$^8$ | m.p. °C. |
|---|---|---|---|---|---|---|---|---|
| III-2 | CH$_3$ | CH$_3$ | 4-Cl | H | | —(CH$_2$)$_4$— | C$_2$H$_5$ | oil* |
| III-3 | CH$_3$ | CH$_3$ | 4-Cl | H | | —(CH$_2$)$_5$— | C$_2$H$_5$ | oil* |
| III-4 | CH$_3$ | CH$_3$ | 4-Cl | H | | —CH$_2$—CHCH$_3$—(CH$_2$)$_3$— | C$_2$H$_5$ | oil* |
| III-5 | CH$_3$ | CH$_3$ | 4-Cl | H | | —(CH$_2$)$_2$—CHCH$_3$—(CH$_2$)$_2$— | C$_2$H$_5$ | oil* |
| III-6 | CH$_3$ | CH$_3$ | 4-Cl | H | | —CH$_2$—O—(CH$_2$)$_3$— | C$_2$H$_5$ | oil* |
| III-7 | CH$_3$ | CH$_3$ | 4-Cl | H | | —(CH$_2$)$_2$—O—(CH$_2$)$_2$— | C$_2$H$_5$ | oil* |
| III-8 | CH$_3$ | CH$_3$ | 4-Cl | H | | —CH$_2$—CHCH$_3$—O—(CH$_2$)$_2$— | C$_2$H$_5$ | oil* |

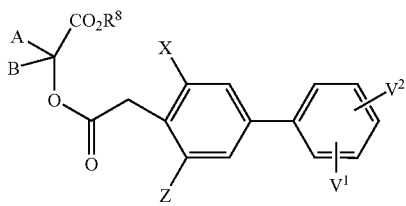

| Ex. No. | X | Z | V¹ | V² | A | B | R⁸ | m.p. °C. |
|---|---|---|---|---|---|---|---|---|
| III-9 | $CH_3$ | $CH_3$ | 4-Cl | H | —$(CH_2)_2$—$CHOC_2H_5$—$(CH_2)_2$— | | $C_2H_5$ | oil* |
| III-10 | $CH_3$ | $CH_3$ | 4-Cl | H | | 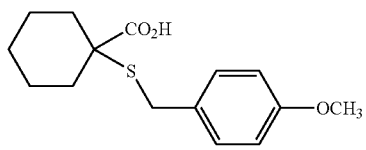 | $C_2H_5$ | oil* |

*The identity was established using GC/MS and the crude products were used directly for preparing the compounds of the formula (I-2-a).

EXAMPLE (IV-1)

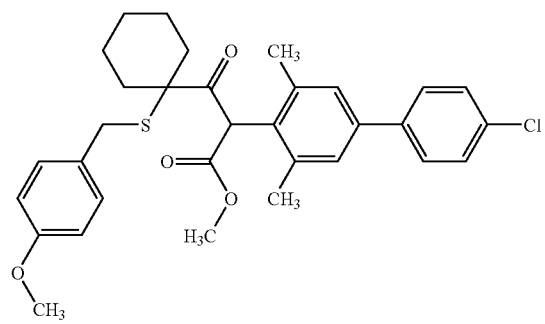

15.0 g of the compound,

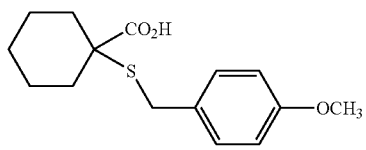

9.63 g of thionyl chloride and 1 drop of DMF were stirred at room temperature for 5 minutes and then at 100° C. until the evolution of gas had ceased. The mixture is then concentrated and dried under high vacuum.

B: At 0° C., 25.3 g of the compound of Example (XXXII-1) are added dropwise to 45.8 ml (96.3 mmol) of a lithium diisopropylamide (LDA) solution in 100 ml of absolute tetrahydrofuran (THF), and the mixture is stirred at this temperature for 30 minutes. The acyl chloride obtained according to A is then added dropwise in 30 ml of THF, cooling is removed and the mixture is stirred for another hour. 300 ml of MTBE and a few drops of water are added and the mixture is washed twice with 300 ml of 10% aqueous ammonium chloride solution each time, dried and concentrated. Yield 45 g (100% of theory) as an oil.

¹H NMR (CDCl₃, 400 MHz): δ=1.5–2.0 (m, 10H, cyclohexyl), 2.4 (s, 6H, 2×Ar—$CH_3$), 3.1; 3.3 (d, 2H, S—$CH_2$) 3.6; 3.7 (s, 2×3H, 2×$OCH_3$), 6.8–7.7 (m, 10H, Ar—H) ppm.

EXAMPLE X-1

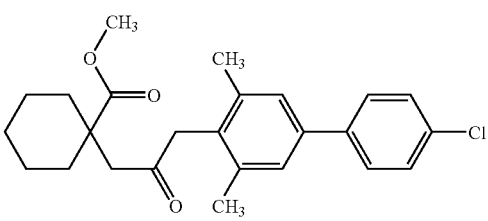

70.0 g of the compound of Example (XXVIII-1), 24.05 g of potassium carbonate and 74.4 g of methyl iodide in 400 ml of acetone are stirred under reflux for 16 hours. The mixture is filtered and the filtrate is concentrated. The residue is chromatographed over silica gel (mobile phase methylene chloride/petroleum ether 4/1). Yield 20.5 g (41% of theory) of an oil.

¹H NMR (CDCl₃, 400 MHz): δ=1.3–1.8 (m, 10H, cyclohexyl), 2.2 (s, 6H, 2×Ar—$CH_3$), 2.95 (s, 2H, $CH_2CO$), 3.55 (s, 3H, $OCH_3$), 3.85 (s, 2H, Ar—$CH_2$), 7.3–7.65 (m, 6H, Ar—H) ppm.

EXAMPLE (XXXVIII-1)

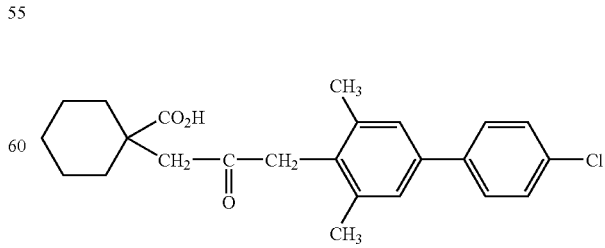

At −15° C., a solution of 51.9 g of the compound of Example (XXXII-1) in 80 ml of THF is added dropwise to 100 ml of a solution of LDA (2 molar) and 200 ml of THF, and the mixture is subsequently stirred at 0° C. for 1 hour. At −15° C., a solution of 20.2 g of the compound

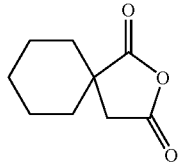

in 30 ml of THF is then added dropwise. The mixture is stirred at room temperature for 2 hours, 300 ml of water and 80 g of ammonium chloride are added and the mixture is acidified with concentrated HCl. The mixture is extracted with ether and the ether phase is concentrated. The residue is boiled under reflux with 200 g of KOH and 660 ml of water for 2 days. After cooling, the mixture is acidified with concentrated HCl and extracted with ether. The crude oily product which remains after concentration is reacted further without any further purification. Yield 70 g (100% of theory).

EXAMPLE (XI-1)

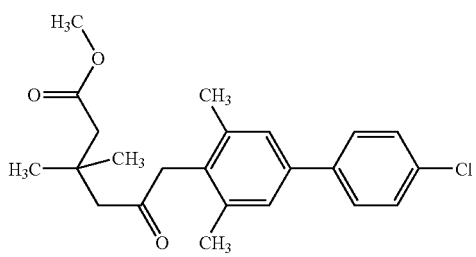

36 g of the compound of Example (XLII-1), 13.2 g of potassium carbonate and 40.8 g of methyl iodide in 200 ml of acetone are boiled under reflux for 16 hours. The mixture is filtered, the filtrate is concentrated and the residue is purified by silica gel column chromatography (mobile phase methylene chloride/petroleum ether 2/1). Yield 12 g (52% of theory), oil.
$^1$H NMR (400 MHz, CDCl$_3$):δ=1.05 (s, 6H, C(CH$_3$)$_2$, 2.2 (s, 6H, 2×Ar—CH$_3$), 2.4; 2.7 (s, 2×2H, CO—CH$_2$), 3.6 (s, 3H, OCH$_3$), 3.85 (s, 2H, Ar—CH$_2$), 7.3–7.65 (m, 6H, Ar—H) ppm.

EXAMPLE (XI-2)

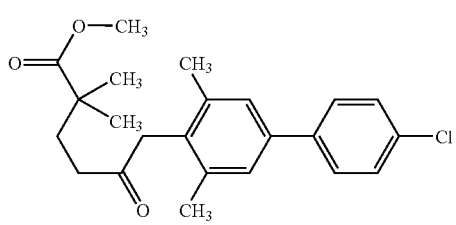

By the method of Example (XI-1), the compound shown above is obtained, likewise as an oil.

$^1$H NMR (400 MHz, CDCl$_3$):δ=1.1 (s, 6H, C(CH$_3$)$_2$), 1.75; 2.55 (t, 2×2H, CH$_2$CH$_2$), 2.2 (s, 6H, 2×Ar—CH$_3$), 3.6 (s, 3H, OCH$_3$), 3.9 (s, 2H, ArCH$_2$), 7.3–7.7 (m, 6H, Ar—H) ppm.

EXAMPLE (XLII-1)

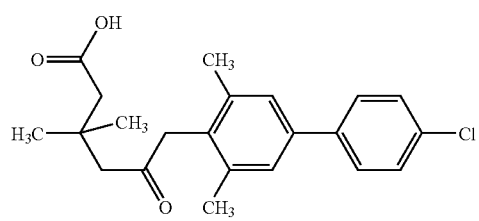

At −15° C., a solution of 27 g of the compound of Example (XXXII-1) in 30 ml of THF is added dropwise to 50 ml of a solution of LDA (2 molar) in 100 ml of THF, and the mixture is stirred at 0° C. for 1 hour. At −15° C., a solution of 8.6 g of the compound

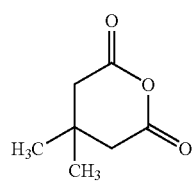

in 20 ml of THF is then added dropwise. The mixture is stirred at room temperature for 2 hours, after which 150 ml of water and 40 g of ammonium chloride are added, and the mixture is acidified with concentrated HCl. The mixture is extracted with ether and the ether phase is concentrated. The residue is boiled under reflux with 100 g of KOH and 330 ml of water for 2 days. After cooling, the mixture is acidified with concentrated HCl and extracted with ether. The crude product (36 g) which remains after concentration is reacted further without any further purification.

EXAMPLE (LXII-2)

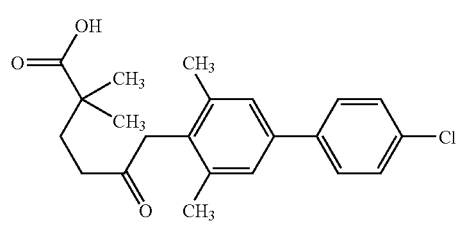

By the method of Example (LXII-1), the compound shown above is obtained.

EXAMPLE XXIV-1

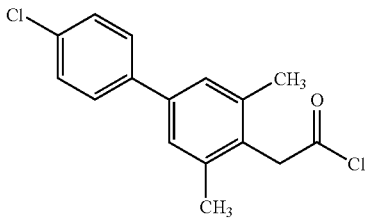

69 g of the acid of Example XXVII-1 are heated with 55 ml of thionyl chloride at 70° C. until the evolution of gas has ceased.

Excess thionyl chloride is subsequently removed under reduced pressure. Yield 54.9 g (74% of theory), m.p.: 102° C.

By the method of Example (XXIV-1), and/or in accordance with the general procedures for preparing the compounds of the formula (XXIV), the following compounds of the formula (XXIV) are obtained:

(XXIV)

| Ex. No. | X | Z | $V^1$ | $V^2$ | m.p. ° C. |
|---|---|---|---|---|---|
| XXIV-2 | $CH_3$ | $CH_3$ | 3-Cl | H | * |
| XXIV-3 | $CH_3$ | $CH_3$ | 2-Cl | H | * |
| XXIV-4 | $CH_3$ | $CH_3$ | 4-$CH_3$ | H | * |
| XXIV-5 | $CH_3$ | $CH_3$ | 2-$CH_3$ | 5-F | * |
| XXIV-6 | $CH_3$ | $CH_3$ | 2-$CH_3$ | 5-$CH_3$ | * |
| XXIV-7 | $CH_3$ | $CH_3$ | 2-$CH_3$ | 3-$CH_3$ | * |
| XXIV-8 | $CH_3$ | $CH_3$ | 2-$OCH_3$ | H | * |
| XXIV-9 | $CH_3$ | $CH_3$ | 3-$CH_3$ | 5-$CH_3$ | * |
| XXIV-10 | $CH_3$ | $CH_3$ | 2-Cl | 4-Cl | * |
| XXIV-11 | $CH_3$ | $CH_3$ | 2-Cl | 3-Cl | * |

*The acyl chlorides were used without any further purification for the synthesis of compounds of the formula (II).

EXAMPLE (XVII-1)

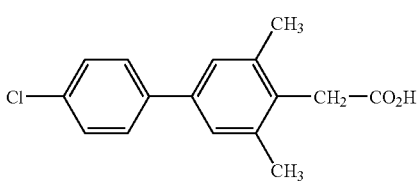

At room temperature, 6 g of the compound of Example (XXXII-1), 1.2 g of lithium hydroxide, 20 ml of ethanol, 100 ml of water and 100 ml of THF are stirred overnight. The THF is removed under reduced pressure and the aqueous solution that remains is repeatedly extracted with methylene chloride. The aqueous phase is acidified with concentrated HCl and the precipitated product is filtered off with suction. Yield 5 g (96% of theory), m.p. 205° C.

By the method of Example (XXVII-1), and/or in accordance with the general procedures for preparing the compounds (XXVII), the following compounds of the formula (XXVII) are obtained:

(XXVII)

| Ex. No. | X | Z | $V^1$ | $V^2$ | m.p. ° C. |
|---|---|---|---|---|---|
| XXVII-2 | $CH_3$ | $CH_3$ | 3-Cl | H | 143 |
| XXVII-3 | $CH_3$ | $CH_3$ | 2-Cl | H | 129 |
| XXVII-4 | $CH_3$ | $CH_3$ | 4-$CH_3$ | H | 154 |
| XXVII-5 | $CH_3$ | $CH_3$ | 2-$CH_3$ | 5-F | 120 |
| XXVII-6 | $CH_3$ | $CH_3$ | 2-$CH_3$ | 5-$CH_3$ | 141 |
| XXVII-7 | $CH_3$ | $CH_3$ | 2-$CH_3$ | 3-$CH_3$ | 155 |
| XXVII-8 | $CH_3$ | $CH_3$ | 2-$OCH_3$ | H | 151 |
| XXVII-9 | $CH_3$ | $CH_3$ | 3-$CH_3$ | 5-$CH_3$ | 173 |
| XXVII-10 | $CH_3$ | $CH_3$ | 2-Cl | 4-Cl | 166 |
| XXVII-11 | $CH_3$ | $CH_3$ | 2-Cl | 3-Cl | 158 |

EXAMPLE (XXXII-1)

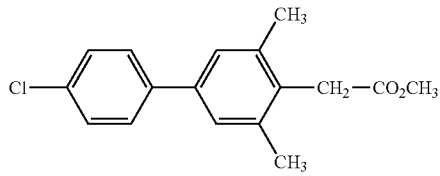

30 g of the compound of Example (XLV-1) are boiled under reflux with 19.8 g of 88% strength KOH in 1000 ml of methanol overnight. After cooling, the mixture is admixed with 20 ml of concentrated sulphuric acid and boiled under reflux for 1 hour. The solid is filtered off with suction and washed with methanol. The methanol in the filtrate is removed under reduced pressure, and the residue is admixed with water and extracted with methylene chloride. The organic phase is dried and concentrated. Yield 1 g (10% of theory), oil.

$^1$H NMR (400 MHz, $CDCl_3$,):δ=2.38 (s, 6H, Ar—C$\underline{H}_3$), 3.70 (s, 3H, OC$\underline{H}_3$), 3.73 (s, 2H, C$\underline{H}_2$), 7.23 (s, 2H Ar$\underline{H}$), 7.36–7.39 (AA', BB', 2H, Ar$\underline{H}$), 7.48–7.51 (AA', BB', 2H, Ar—H) ppm.

EXAMPLE (XXXII-2)

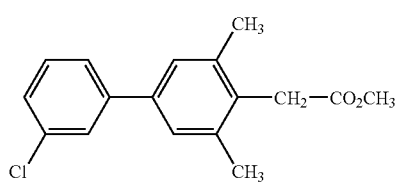

Under argon, 6.1 g of 3-chlorophenylboronic acid, 0.15 g of bis(triphenylphosphine)palladium(II) chloride and 65 ml of 1M $Na_2CO_3$ solution are introduced into 7.68 g of methyl 4-bromo-2,6-dimethylphenyl acetate in 85 ml of dimethoxyethane, and the mixture is stirred under reflux overnight. The mixture is diluted with water and extracted with ethyl acetate. The organic phase is washed with ammonium chloride solution, water and saturated sodium chloride solution, dried and concentrated. Yield 4.3 g (36% of theory), m.p.: 56° C.

By the method of Examples (XXXII-1) and (XXXII-2), and/or in accordance with the general procedures for preparing the compounds (XXXII), the following compounds of the formula (XXXII) are obtained:

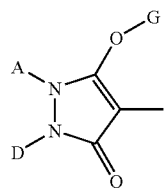

(XXXII)

| Ex. No. | X | Z | $V^1$ | $V^2$ | $R^8$ | m.p. ° C. |
|---|---|---|---|---|---|---|
| XXXII-2 | $CH_3$ | $CH_3$ | 3-Cl | H | $CH_3$ | 56 |
| XXXII-3 | $CH_3$ | $CH_3$ | 2-Cl | H | $CH_3$ | oil |
| XXXII-4 | $CH_3$ | $CH_3$ | 4-Cl | H | $CH_3$ | 137 |
| XXXII-5 | $CH_3$ | $CH_3$ | 2-$CH_3$ | 5-F | $CH_3$ | oil |
| XXXII-6 | $CH_3$ | $CH_3$ | 2-$CH_3$ | 5-$CH_3$ | $CH_3$ | oil |
| XXXII-7 | $CH_3$ | $CH_3$ | 2-$CH_3$ | 3-$CH_3$ | $CH_3$ | oil |
| XXXII-8 | $CH_3$ | $CH_3$ | 2-$OCH_3$ | H | $CH_3$ | 85 |
| XXXII-9 | $CH_3$ | $CH_3$ | 3-$CH_3$ | 5-$CH_3$ | $CH_3$ | oil |
| XXXII-10 | $CH_3$ | $CH_3$ | 2-Cl | 4-Cl | $CH_3$ | oil |
| XXXII-11 | $CH_3$ | $CH_3$ | 2-Cl | 3-Cl | $CH_3$ | oil |

EXAMPLE XLVI-1

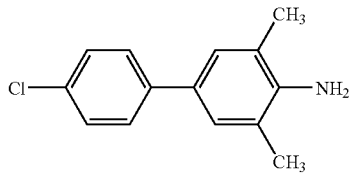

5 g of 4-bromo-2,6-dimethylaniline, 3.88 g of 4-chlorophenylboronic acid and 0.11 g of bis(triphenylphosphine) palladium(II) chloride in 48.8 ml of 1M $Na_2CO_3$ solution and 65 ml of dimethoxyethane are heated under reflux overnight. The mixture is admixed with water and extracted with ethyl acetate. The organic phase is washed with ammonium chloride solution, water and saturated sodium chloride solution, dried and concentrated. Yield 4 g (77% of theory), m.p.: 96° C.

The invention claimed is:
1. A compound of the formula (I)

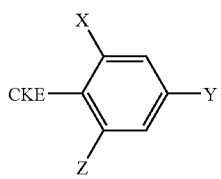

(I)

in which
X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or in each case optionally substituted phenyl, phenoxy, phenylthio, phenylalkoxy or phenylalkylthio, Y represents in each case optionally substituted cycloalkyl, aryl, or hetaryl Z represents hydrogen, halogen, alkyl, alkoxy, alkenyloxy, halogenoalkyl, halogenoalkoxy, halogenoalkenyloxy, nitro or cyano, CKE represents

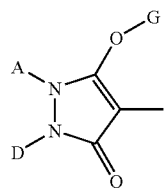

(4)

wherein
A represents hydrogen, in each case optionally halogen-substituted alkyl, alkenyl, alkoxyalkyl, polyalkoxyalkyl, alkylthioalkyl, saturated or unsaturated, optionally substituted cycloalkyl in which optionally at least one ring atom is replaced by a heteroatom, or in each case optionally halogen-, alkyl-, halogenoalkyl-, alkoxy-, halogenoalkoxy-, cyano- or nitro-substituted aryl, arylalkyl or hetaryl, D represents hydrogen or an optionally substituted radical selected from the series consisting of alkyl, alkenyl, alkinyl, alkoxyalkyl, polyalkoxyalkyl, alkylthioalkyl, saturated or unsaturated cycloalkyl in which one or more ring members are optionally replaced by heteroatoms, arylalkyl, aryl, hetarylalkyl or hetaryl or A and D together with the atoms to which they are attached represent a saturated or unsaturated cycle which is unsubstituted or substituted in the A,D moiety and which optionally contains at least one further heteroatom, G represents hydrogen (a) or represents one of the groups (b)

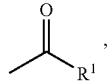

(c)

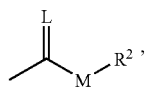

(d)

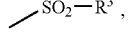

(e)

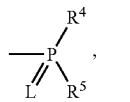

E or (f)

(g)

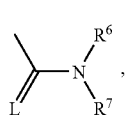

in which

E represents a metal ion equivalent or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another each represent in each case optionally halogen-substituted alkyl, alkoxy, alkylamino, dialkylamino, alkylthio, alkenylthio, cyclo alkylthio and represents optionally substituted phenyl, benzyl, phenoxy or phenylthio, $R^6$ and $R^7$ independently of one another each represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulphur.

2. A compound of the formula (I) according to claim 1 wherein

X represents halogen, $C_1$–$C_6$-alkyl, $C_1$–$C_6$-halogenoalkyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkoxy, $C_3$–$C_6$-halogenoalkenyloxy, nitro, cyano or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, benzyloxy or benzylthio, Y represents one of the radicals

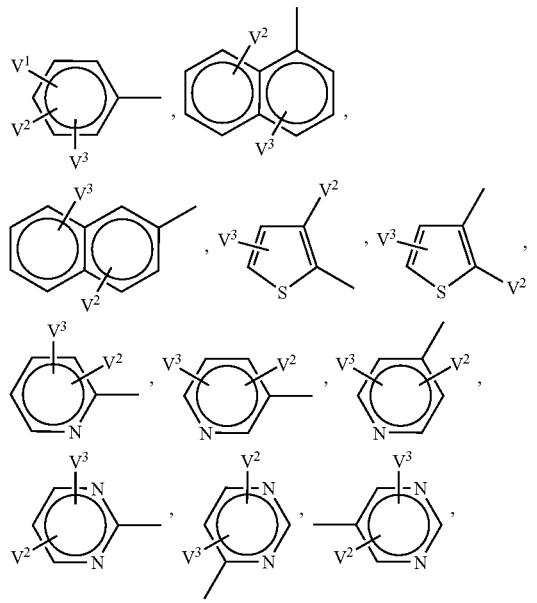

-continued

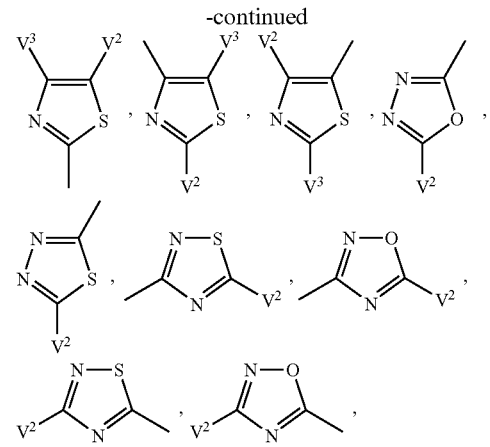

wherein $V^1$ represents hydrogen, halogen, $C_1$–$C_{12}$-alkyl, $C_1$–$C_6$-alkoxy, $C_1$–$C_4$-halogenoalkyl, $C_1$–$C_4$-halogenoalkoxy, nitro, cyano or phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally mono- or poly-substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, $V^2$ and $V^3$ independently of one another each represent hydrogen, halogen, $C_1$–$C_6$-alkyl, $C_1$–$C_6$-alkoxy, $C_1$–$C_4$-halogenoalkyl or $C_1$–$C_4$-halogeno-alkoxy, Z represents hydrogen, halogen, $C_1$–$C_6$-alkyl, $C_1$–$C_6$-halogenoalkyl, $C_1$–$C_6$-alkoxy, $C_1$–$C_6$-halogenoalkoxy, nitro or cyano, CKE represents (4)

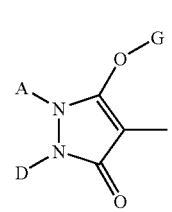

wherein

A represents hydrogen or in each case optionally halogen-substituted $C_1$–$C_{12}$-alkyl, $C_3$–$C_8$-alkenyl, $C_1$–$C_{10}$-alkoxy-$C_1$–$C_8$-alkyl, poly-$C_1$–$C_8$-alkoxy-$C_1$–$C_8$-alkyl, $C_1$–$C_{10}$-alkylthio-$C_1$–$C_6$-alkyl, optionally halogen-, $C_1$–$C_6$-alkyl- or $C_1$–$C_6$-alkoxy-substituted $C_3$–$C_8$-cycloalkyl in which optionally one or two not directly adjacent ring members are replaced by oxygen and/or sulphur or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted $C_6$- or $C_{10}$-aryl, hetaryl having 5 to 6 ring atoms or $C_6$- or $C_{10}$-aryl-$C_1$–$C_6$-alkyl, D represents hydrogen, in each case optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl, $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-halogen-oalkyl-substituted $C_3$–$C_8$-cycloalkyl in which optionally one ring member is replaced by oxygen or sulphur or in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 or 6 ring atoms, phenyl-$C_1$–$C_6$-alkyl or hetaryl-$C_1$–$C_6$-alkyl having 5 or 6 ring atoms, or A and D together represent in each case optionally substituted $C_3$–$C_6$-alkane-diyl or $C_3$–$C_6$-alkenediyl in which optionally one methylene group is replaced by oxygen or sulphur, possible substituents in each case being:

halogen, hydroxyl, mercapto or in each case optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy, or a further $C_3$–$C_6$-alkanediyl grouping, $C_3$–$C_6$-alkenediyl grouping or a butadienyl grouping which is optionally substituted by $C_1$–$C_6$-alkyl or in which optionally two adjacent substituents together with the carbon atoms to which they are attached form a further saturated or unsaturated cycle having 5 or 6 ring atoms which cycle may contain oxygen or sulphur, or which may optionally contain one of the groups below

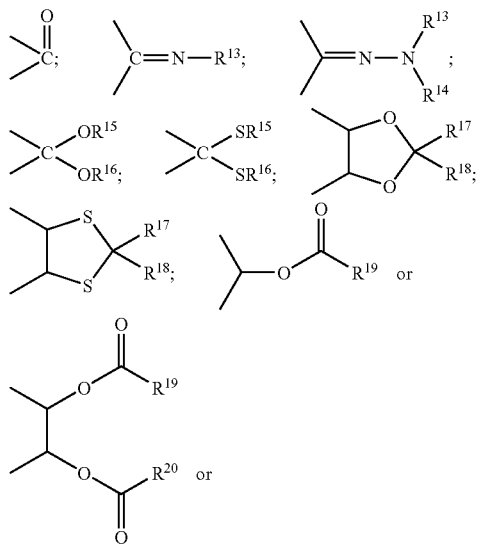

G represents hydrogen (a) or represents one of the groups

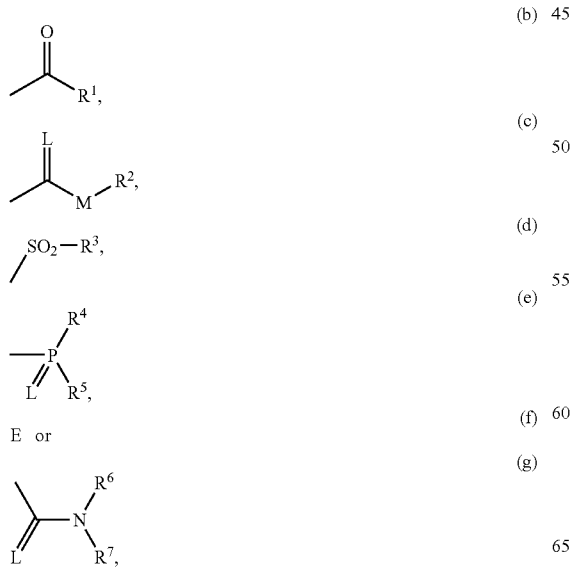

in which

E represents a metal ion or an ammonium ion,

L represents oxygen or sulphur and

M represents oxygen or sulphur, $R^1$ represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl or optionally halogen-, $C_1$–$C_6$-alkyl- or $C_1$–$C_6$-alkoxy-substituted $C_3$–$C_8$-cycloalkyl in which optionally one or more not directly adjacent ring members are replaced by oxygen and/or sulphur, represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, represents optionally halogen- or $C_1$–$C_6$-alkyl-substituted 5- or 6-membered hetaryl, represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl, $R^2$ represents in each case optionally halogen-substituted $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl or represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl, $R^3$ represents optionally halogen-substituted $C_1$–$C_8$-alkyl or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^4$ and $R^5$ independently of one another each represent in each case optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio or represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio, $R^6$ and $R^7$ independently of one another each represent hydrogen, represent in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, represent optionally halogen-, $C_1$–$C_8$-halogenoalkyl-, $C_1$–$C_8$-alkyl- or $C_1$–$C_8$-alkoxy-substituted phenyl, optionally halogen-, $C_1$–$C_8$-alkyl-, $C_1$–$C_8$-halogenoalkyl- or $C_1$–$C_8$-alkoxy-substituted benzyl or together represent an optionally $C_1$–$C_4$-alkyl-substituted $C_3$–$C_6$-alkylene radical in which optionally one carbon atom is replaced by oxygen or sulphur, $R^{13}$ represents hydrogen, represents in each case optionally halogen-substituted $C_1$–$C_8$-alkyl or $C_1$–$C_8$-alkoxy, represents optionally halogen-, $C_1$–$C_4$-alkyl- or $C_1$–$C_4$-alkoxy-substituted $C_3$–$C_8$-cycloalkyl in which optionally one methylene group is replaced by oxygen or sulphur, or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy, $R^{14}$ represents hydrogen or $C_1$–$C_8$-alkyl, or $R^{13}$ and $R^{14}$ together represent $C_4$–$C_6$-alkanediyl, $R^{15}$ and $R^{16}$ are identical or different and each represent $C_1$–$C_6$-alkyl, or $R^{15}$ and $R^{16}$ together represent a $C_2$–$C_4$-alkanedjyl radical which is optionally substituted by $C_1$–$C_6$-alkyl, $C_1$–$C_6$-halogenoalkyl or by optionally halogen-, $C_1$–$C_6$-alkyl-, $C_1$–$C_4$-halogenoalkyl-, $C_1$–$C_6$-alkoxy-, $C_1$–$C_4$-halogenoalkoxy-, nitro- or cyano-substituted phenyl, $R^{17}$ and $R^{18}$ independently of one another each represent hydrogen, represent optionally halogen-substituted $C_1$–$C_8$-alkyl or represent optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, or $R^{17}$ and $R^{18}$ together with the carbon atom to which they are attached represent a carbonyl group or represent optionally halogen-, $C_1$–$C_4$-alkyl- or $C_1$–$C_4$-alkoxy-substituted $C_5$–$C_7$-cycloalkyl in which optionally one methylene group is replaced by oxygen or sulphur and $R^{19}$ and $R^{20}$ independently of one another each represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

3. A compound of the formula (I) according to claim 1 wherein

X represents fluorine, chlorine, bromine, $C_1$–$C_4$-alkyl, $C_1$–$C_4$-alkoxy, $C_3$–$C_4$-alkenyloxy, $C_1$–$C_4$-halogenoalkyl, $C_1$–$C_4$-halogenoalkoxy, $C_3$–$C_4$-halogenoalkenyloxy, nitro or cyano, Y represents

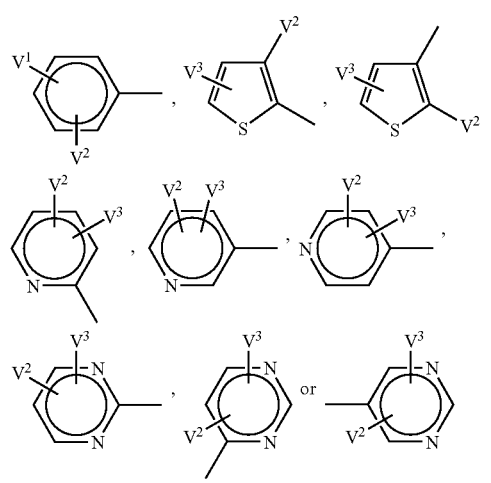

wherein $V^1$ represents hydrogen, fluorine, chlorine, bromine, $C_1$–$C_6$-alkyl, $C_1$–$C_4$-alkoxy, $C_1$–$C_2$-halogenoalkyl, $C_1$–$C_2$-halogenoalkoxy, nitro, cyano or phenyl, phenoxy, phenoxy-$C_1$–$C_2$-alkyl, phenyl-$C_1$–$C_2$-alkoxy, phenylthio-$C_1$–$C_2$-alkyl or phenyl-$C_1$–$C_2$-alkylthio, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, $V^2$ and $V^3$ independently of one another represents hydrogen, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy, Z represents hydrogen, fluorine, chlorine, bromine, $C_1$–$C_4$-alkyl, $C_1$–$C_4$-halogenoalkyl, $C_1$–$C_4$-alkoxy or $C_1$–$C_4$-halogenoalkoxy, CKE represents

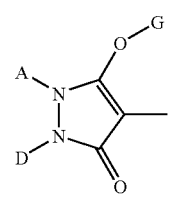

(4)

wherein

A represents hydrogen, in each case optionally fluorine- or chlorine-substituted $C_1$–$C_{10}$-alkyl, $C_1$–$C_8$-alkoxy-$C_1$–$C_6$-alkyl, optionally fluorine-, chlorine-, $C_1$–$C_4$-alkyl- or $C_1$–$C_4$-alkoxy-substituted $C_3$–$C_7$-cycloalkyl in which optionally one ring member is replaced by oxygen or sulphur or in each case optionally fluorine-, chlorine-, bromine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, furanyl, pyridyl, im idazolyl, triazolyl, pyrazolyl, pyrimidyl, thiazolyl, thienyl or phenyl-$C_1$–$C_4$-alkyl, D represents hydrogen, represents in each case optionally substituted $C_1$–$C_{10}$-alkyl, or substituted $C_3$–$C_7$-cycloalkyl in which optionally one methylene group is replaced by oxygen or sulphur.

A and D together represent optionally substituted $C_3$–$C_5$-alkanediyl in which one methylene group may be replaced by a carbonyl group, oxygen or sulphur, possible substituents being hydroxyl, $C_1$–$C_6$-alkyl or $C_1$–$C_4$-alkoxy, G represents hydrogen (a) or represents one of the groups (b)

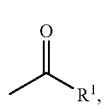

(c)

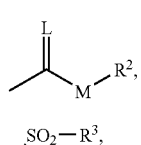

(d)

(e)

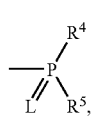

(f)

E or (g)

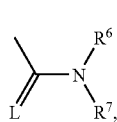

in which

E represents a metal ion or an ammonium ion,

L represents oxygen or sulphur and

M represents oxygen or sulphur, $R^1$ represents in each case optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, poly-$C_1$–$C_6$-alkoxy-$C_1$–$C_6$-alkyl or optionally fluorine-, chlorine-, $C_1$–$C_5$-alkyl- or $C_1$–$C_5$-alkoxy-substituted $C_3$–$C_7$-cycloalkyl in which optionally one or two not directly adjacent ring members are replaced by oxygen and/or sulphur, represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, represents in each case optionally fluorine-, chlorine-, bromine- or $C_1$–$C_4$-alkyl-substituted pyrazolyl, thiazolyl, pyridyl, pyrimidyl, furanyl or thienyl, represents optionally fluorine-, chlorine-, bromine- or $C_1$–$C_4$-alkyl-substituted phenoxy-$C_1$–$C_3$-alkyl or represents in each case optionally fluorine-, chlorine-, bromine-, amino- or $C_1$–$C_4$-alkyl-substituted pyridyloxy-$C_1$–$C_3$-alkyl, pyrimidyloxy-$C_1$–$C_3$-alkyl or thiazolyloxy-$C_1$–$C_3$-alkyl, $R^2$ represents in each case optionally fluorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents optionally fluorine-, chlorine-, $C_1$–$C_4$-alkyl- or $C_1$–$C_4$-alkoxy-substituted $C_3$–$C_7$-cycloalkyl or represents in each case optionally fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl, $R^3$ represents optionally fluorine-substituted $C_1$–$C_6$-alkyl or represents in each case optionally fluorine-, chlorine-, bromine-, $C_1$–$C_4$-alkyl-, $C_1$–$C_4$-alkoxy-, $C_1$–$C_3$-halogenoalkyl-, $C_1$–$C_3$-halogenoalkoxy-, cyano- or nitro-substituted phenyl or benzyl, $R^4$ and $R^5$ independently of one another each represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio, $C_3$–$C_6$-cycloalkylthio or represent in each case optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio, and $R^6$ and $R^7$ independently of one another each represent hydrogen, $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, represent optionally fluorine-, chlorine-, bromine-, $C_1$–$C_3$-halogenoalkyl-, $C_1$–$C_4$-alkyl- or $C_1$–$C_4$-alkoxy-substituted phenyl, represent optionally fluorine-, chlorine-, bromine-, $C_1$–$C_4$-alkyl-, $C_1$–$C_3$-halogenoalkyl- or $C_1$–$C_4$-alkoxy-substituted benzyl, or together represent an optionally methyl- or ethyl-substituted $C_4$–$C_5$-alkylene radical in which optionally one methylene group is replaced by oxygen or sulphur.

4. A compound of the formula (I) according to claim 1 wherein

X represents fluorine, chlorine, methyl, ethyl, propyl, iso-propyl, methoxy, ethoxy, propoxy, iso-propoxy, trifluoromethyl, difluoromethoxy, trifluoromethoxy, nitro or cyano, Y represents

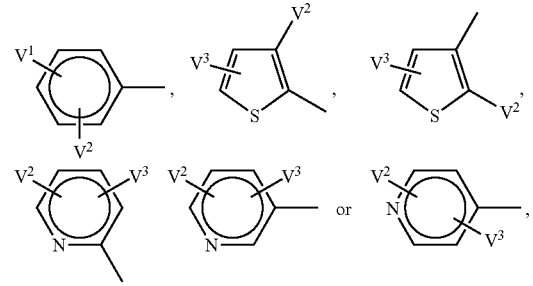

wherein $V^1$ represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, nitro, cyano or phenyl, $V^2$ and $V^3$ independently of one another each represents hydrogen, fluorine, chlorine, methyl, ethyl, n-propyl, iso-propyl, methoxy, ethoxy, trifluoromethyl or trifluoromethoxy, Z represents hydrogen, fluorine, chlorine, methyl, ethyl, n-propyl, methoxy, ethoxy or n-propoxy, CKE represents (4)

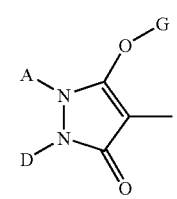

wherein

A represents hydrogen, in each case optionally fluorine-substituted $C_1$–$C_8$-alkyl or $C_1$–$C_6$-alkoxy-$C_1$–$C_4$-alkyl, optionally fluorine-, methyl-, ethyl- or methoxy-substituted $C_3$–$C_6$-cycloalkyl in which optionally one ring member is replaced by oxygen or sulphur or represents in each case optionally fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl or benzyl, D represents hydrogen, represents in each case optionally fluorine- or chlorine-substituted $C_1$–$C_8$-alkyl, $C_3$–$C_4$-alkenyl, $C_1$–$C_6$-alkoxy-$C_2$–$C_4$-alkyl, $C_1$–$C_4$-alkylthio-$C_2$–$C_4$-alkyl or $C_3$–$C_6$-cycloalkyl in which optionally one methylene group is replaced by oxygen or sulphur or (but not in the case of the compounds of the formulae (I-1) and (I-4)) represents in each case optionally fluorine-, chlorine-, methyl-, ethyl-, n-propyl-, iso-propyl-, methoxy-, ethoxy-, trifluoromethyl- or trifluoromethoxy-substituted phenyl, furanyl, pyridyl, thienyl or benzyl, or A and D together represent optionally substituted $C_3$–$C_4$-alkanediyl in which optionally one carbon atom is replaced by sulphur and which is optionally substituted by hydroxyl, methyl, ethyl, methoxy or ethoxy, G represents hydrogen (a) or represents one of the groups

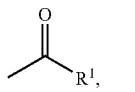
(b)

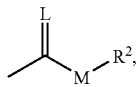
(c)

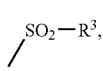
(d)

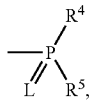
(e)

E or
(f)

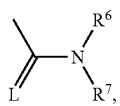
(g)

in which

E represents a metal ion or an ammonium ion,

L represents oxygen or sulphur and

M represents oxygen or sulphur, $R^1$ represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or optionally fluorine-, chlorine-, methyl-, ethyl-, n-propyl-, i-propyl-, n-butyl-, i-butyl-, tert-butyl-, methoxy-, ethoxy-, n-propoxy- or iso-propoxy-substituted $C_3$–$C_6$-cycloalkyl in which optionally one or two not directly adjacent ring members are replaced by oxygen and/or sulphur, represents optionally fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl, represents optionally fluorine-, chlorine-, bromine-, methyl-, ethyl-, n-propyl-, i-propyl-, methoxy-, ethoxy-, trifluoromethyl- or trifluoro-methoxy-substituted benzyl, represents in each case optionally fluorine-, chlorine-, bromine-, methyl- or ethyl-substituted furanyl, thienyl, pyridyl, pyrimidyl, thiazolyl or pyrazolyl, represents optionally fluorine-, chlorine-, methyl- or ethyl-substituted phenoxy-$C_1$–$C_2$-alkyl or represents in each case optionally fluorine-, chlorine-, amino-, methyl- or ethyl-substituted pyridyloxy-$C_1$–$C_2$-alkyl, pyrimidyloxy-$C_1$–$C_2$-alkyl or thiazolyloxy-$C_1$–$C_2$-alkyl, $R^2$ represents in each case optionally fluorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, represents optionally fluorine-, chlorine-, methyl-, ethyl-, n-propyl-, isopropyl- or methoxy-substituted $C_3$–$C_6$-cycloalkyl, or represents in each case optionally fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl, $R^3$ represents in each case optionally fluorine-substituted methyl, ethyl, n-propyl, isopropyl or in each case optionally fluorine-, chlorine-, bromine-, methyl-, tert-butyl-, methoxy-, trifluoromethyl-, trifluoromethoxy-, cyano- or nitro-substituted phenyl or benzyl, $R^4$ and $R^5$ independently of one another each represent $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio or represent in each case optionally fluorine-, chlorine-, bromine-, nitro-, cyano-, $C_1$–$C_2$-alkoxy-, $C_1$–$C_2$-fluoroalkoxy-, $C_1$–$C_2$-alkylthio-, $C_1$–$C_2$-fluoroalkylthio- or $C_1$–$C_3$-alkyl-substituted phenyl, phenoxy or phenylthio, and $R^6$ and $R^7$ independently of one another each represent hydrogen, represent $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, represent optionally fluorine-, chlorine-, bromine-, trifluoromethyl-, methyl- or methoxy-substituted phenyl, represent optionally fluorine-, chlorine-, bromine-, methyl-, trifluoromethyl- or methoxy-substituted benzyl, or together represent a $C_5$–$C_6$-alkylene radical in which optionally one methylene group is replaced by oxygen or sulphur.

5. A process for preparing a compound of the formula (I) according to claim 1, comprising (D) when said compound of the formula (I) is a compound of the formula (I-4-a)

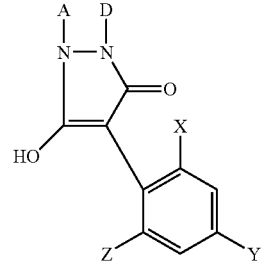
(I-4-a)

in which

A, D, X, Y and Z are each as defined in claim 1, reacting (Dα) halogenocarbonyl ketenes of the formula (V)

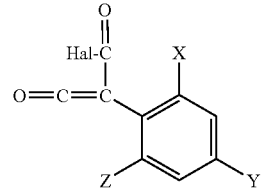
(V)

in which

X, Y and Z are each as defined above and

Hal represents halogen, or by (Cβ) reacting a malonic acid derivative of the formula (VI)

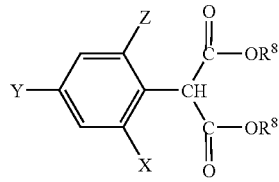
(VI)

in which

R⁸ represents alkyl,

X,Y and Z are each as defined above, with a hydrazine of the formula (VII)

A-NH—NH-D    (VII)

in which

A and D are each as defined above, optionally in the presence of a diluent and optionally in the presence of a base, or (I) when said compound of the formula (I) is a compound of the formula (I-4-a) defined above, reacting a compound of the formula (I-4'-a), (I-4'-a):

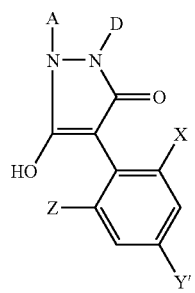

in which

A, D, X and Z are each as defined above and

Y' represents chlorine, bromine or iodine with a boronic acid of the formula (XII)

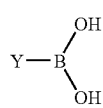
(XII)

in which

Y is as defined above, in the presence of a solvent, a base and a catalyst, or (J) when said compound of the formula (I) is a compound of the formula (I-4-b)

(I-4-b):

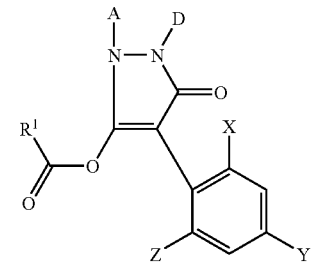

in which A, D, R¹, X, Y and Z are each as defined in claim 1, (Jα) reacting a compound of the formula (I-4-a) above in which A, D, X Y and Z are each as defined above with an acyl halide of the formula (XIII).

(XIII)

in which

R¹ is as defined above and

Hal represents halogen or (Jβ) reacting a compound of the formula (I-4-a) above in which A, D, X Y and Z are each as defined above with a carboxylic anhydride of the formula (XIV)

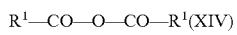
R¹—CO—O—CO—R¹(XIV)

in which

R¹ is as defined above, optionally in the presence of a diluent and optionally in the presence of an acid binder, or (K) when said compound of the formula (I) is a compound of the formula (I-4-c)

(I-4-c):

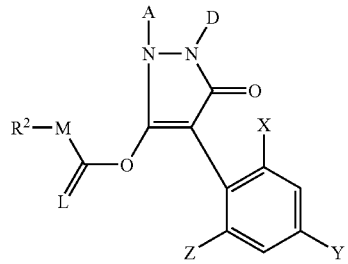

in which A, D, R², M, X, Y and Z are each as defined in claim 1 and L represents oxygen, reacting a compound of the formula (I-4-a) above in which A, D, X Y and Z are each as defined above with a chloroformic ester or a chloroformic thioester of the formula (XV)

R²-M-CO—Cl    (XV)

in which
R² and M are each as defined above,
optionally in the presence of a diluent and optionally in the presence of an acid binder, or
(L) when the compound of the formula (I) is a compound of the formula (I-4-c) defined above in which A, D, R², M, X, Y and Z are each as defined above and L represents sulphur,
reacting a compound of the formula (I-4-a) defined above in which A, D, X, Y and Z are each as defined above with a chloromonothioformic ester or a chlorodithioformic ester of the formula (XVI)

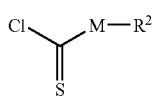
(XVI)

in which
M and R² are each as defined above,
optionally in the presence of a diluent and optionally in the presence of an acid binder, or
(M) when the compound of the formula (I) is a compound of the formula (I-4-d)

(I-4-d):

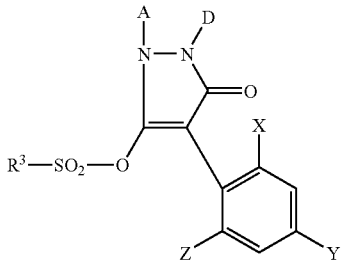

in which A, D, R³, X, Y and Z are each as defined in claim 1, reacting a compound of the formula (I-4-a) defined above in which A, D, X, Y and Z are each as defined above with a suiphonyl chloride of the formula (XVII)

 (XVII)

in which
R³ is as defined above,
optionally in the presence of a diluent and optionally in the presence of an acid binder, or
(N) when the compound of the formula (I) is a compound of the formula (I-4-e)

(I-4-e):

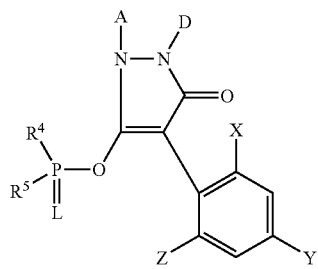

in which A, D, L, R⁴, R⁵, X, Y and Z are each as defined in claim 1,
reacting a compound of the formula (I-4-a) defined above in which A, D, X, Y and Z are each as defined above with a phosphorus compound of the formula

(XVIII)

in which
L, R⁴ and R⁵ are each as defined above and
Hal represents halogen,
optionally in the presence of a diluent and optionally in the presence of an acid binder, or
(O) when the compound of the formula (I) is a compound of the formula (I-4-f)

(I-4-f):

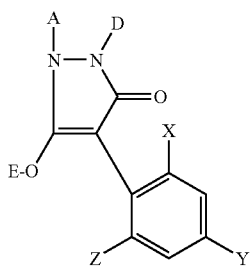

in which A, D, E, X, Y and Z are each as defined in claim 1, reacting a compound of the formula (I-4-a) defined above in which A, D, X, Y and Z are each as defined above with a with metal compound or amine of the formulae (XIX) or (XX)

 (XIX)

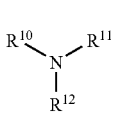 (XX)

in which
Me represents a mono- or divalent metal,
t represents the number 1 or 2 and
R¹⁰, R¹¹, R¹² independently of one another each represent hydrogen or alkyl,
optionally in the presence of a diluent, or
(P) when the compound of the formula (I) is a compound of the formula (I-4-g)

(I-4-g):

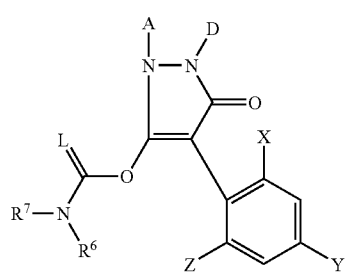

wherein A, D, L, $R^6$, $R^7$, X, Y and Z are each as defined in claim 1, (Pα) reacting a compound of the formula (I-4-a) defined above in which A, D, X, Y and Z are each as defined above with an isocyanate or an isothiocyanate of the formula (XXI)

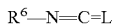　　　　　　　　　　　　　　(XXI)

in which
$R^6$ and L are each as defined above,
optionally in the presence of a diluent and optionally in the presence of a catalyst, or (Pβ) reacting a compound of the formula (I-4-a) defined above in which A, D, X, Y and Z are each as defined above with a carbamoyl chlorides or thiocarbamoyl chloride of the formula (XXII)

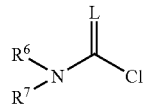　　　　　　　　　　　　　(XXII)

in which

L, $R^6$ and $R^7$ are each as defined above, optionally in the presence of a diluent and optionally in the presence of an acid binder.

6. A pesticide and/or herbicide, comprising at least one compound of the formula (I) according to claim 1.

7. A method for controlling pests comprising the step of applying an effective amount of a compound of the formula (I) according to claim 1 to a member selected from the group consisting of said pests, a habitat for said pests, and combinations thereof.

8. A method for preparing a pesticide and/or a herbicide, comprising the step of mixing a compound of the formula (I) according to claim 1 with a member selected from the group consisting of an extender, a surfactant and combinations thereof.

* * * * *